(12) United States Patent
Fujio et al.

(10) Patent No.: US 7,459,465 B2
(45) Date of Patent: Dec. 2, 2008

(54) ISOQUINOLINE COMPOUND AND PHARMACEUTICAL USE THEREOF

(75) Inventors: Masakazu Fujio, Tokyo (JP); Hiroyuki Satoh, Tokyo (JP); Shinya Inoue, Tokyo (JP); Toshifumi Matsumoto, Tokyo (JP); Yasuhiro Egi, Tokyo (JP)

(73) Assignee: Mitsubishi Tanabe Pharma Corporation, Osaka (JP)

(*) Notice: Subject to any disclaimer, the term of this patent is extended or adjusted under 35 U.S.C. 154(b) by 0 days.

(21) Appl. No.: 11/688,103

(22) Filed: Mar. 19, 2007

(65) Prior Publication Data

US 2007/0161620 A1    Jul. 12, 2007

Related U.S. Application Data

(63) Continuation of application No. 10/836,377, filed on Apr. 30, 2004, now Pat. No. 7,220,759, which is a continuation-in-part of application No. PCT/JP03/12608, filed on Oct. 1, 2003.

(30) Foreign Application Priority Data

| Oct. 1, 2002 | (JP) | ............................. 2002-288833 |
| Nov. 22, 2002 | (JP) | ............................. 2002-340175 |
| Apr. 14, 2003 | (JP) | ............................. 2003-109160 |

(51) Int. Cl.
C07D 403/02    (2006.01)
A61K 31/47    (2006.01)

(52) U.S. Cl. ..................................... 514/309; 546/141
(58) Field of Classification Search ................ 546/141; 514/309
See application file for complete search history.

(56) References Cited

U.S. PATENT DOCUMENTS

| 4,113,731 | A | 9/1978 | Winters et al. |
| 4,808,595 | A | 2/1989 | Hoffman, Jr. |
| 7,220,759 | B2* | 5/2007 | Fujio et al. .................. 514/309 |
| 2004/0176361 | A1 | 9/2004 | Fujio et al. |

FOREIGN PATENT DOCUMENTS

| CA | 2 371 174 A1 | 11/2000 |
| CA | 2 371 645 A1 | 11/2000 |
| CA | 2 372 704 A1 | 11/2000 |
| DE | 2 121 031 A | 11/1972 |
| EP | 0 355 750 A1 | 2/1990 |
| EP | 1 142 881 A1 | 10/2001 |
| EP | 1 148 053 A1 | 10/2001 |
| EP | 1 396 488 A1 | 3/2004 |
| GB | 1062357 | 3/1967 |
| GB | 1174272 | 12/1969 |
| JP | 46-12454 B | 3/1971 |
| JP | 52-156875 | 12/1977 |
| JP | 54-84597 A | 7/1979 |
| JP | 64-42472 A | 2/1989 |
| JP | 02-124874 A | 5/1990 |
| WO | WO 99/08680 A1 | 2/1999 |
| WO | WO 99/11624 A1 | 3/1999 |
| WO | WO 99/11628 A1 | 3/1999 |
| WO | WO 99/11645 A1 | 3/1999 |
| WO | WO 99/11649 A2 | 3/1999 |
| WO | WO 99/59973 A1 | 11/1999 |
| WO | WO 00/42025 A1 | 7/2000 |
| WO | WO 00/44726 A1 | 8/2000 |
| WO | WO 00/64878 A1 | 11/2000 |
| WO | WO 00/67734 A2 | 11/2000 |
| WO | WO 00/68206 A1 | 11/2000 |
| WO | WO 01/79184 A1 | 10/2001 |
| WO | WO 02/44157 A2 | 6/2002 |
| WO | WO 02/48117 A1 | 6/2002 |
| WO | WO 02/090334 A1 | 11/2002 |
| WO | WO 02/94790 A1 | 11/2002 |
| WO | WO 03/063874 A1 | 8/2003 |
| WO | WO 2004/048339 A1 | 6/2004 |

OTHER PUBLICATIONS

Nunami et al., Journal of Organic Chemistry, 1979, vol. 44, No. 11, pp. 1887-1888.*
Eliasson et al., Nature Medicine, 3(10): 1089-1095 (1997).
Kimoto et al., Yakugaku Zasshi, 91(12): 1279-1285 (1971).
Ohta et al., Chem. Pharm. Bull., 41(6): 1188-1190 (1993).
Tomisawa et al., Chem. Pharm Bull, 19(11): 2414-2417 (1971).

* cited by examiner

Primary Examiner—Zinna N Davis
(74) Attorney, Agent, or Firm—Leydig, Voit & Mayer, Ltd.

(57) ABSTRACT

The present invention relates to an isoquinoline compound represented by the following formula (I), an optically active form thereof, a pharmaceutically acceptable salt thereof, a water adduct thereof, a hydrate thereof and a solvate thereof, as well as an agent for the prophylaxis and/or treatment of a disease caused by hyperreactivity of poly(ADP-ribose)polymerase, containing the compound, and a poly(ADP-ribose) polymerase inhibitor containing the compound. In addition, this compound is useful as an agent for the prophylaxis and/or treatment of cerebral infarction, particularly as an agent for the prophylaxis and/or treatment of acute cerebral infarction. Furthermore, this compound is useful as a prophylactic and/or therapeutic agent that improves neurological symptoms associated with cerebral infarction, particularly acute cerebral infarction.

(I)

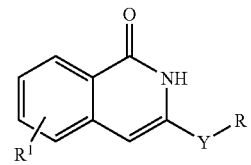

wherein the symbols are the same as defined in the description.

36 Claims, No Drawings

ISOQUINOLINE COMPOUND AND PHARMACEUTICAL USE THEREOF

CROSS REFERENCE TO RELATED APPLICATIONS

This application is a continuation of co-pending U.S. patent application Ser. No. 10/836,377, filed Apr. 30, 2004, which is a continuation-in-part of International Patent Application No. PCT/JP2003/012608, filed Oct. 1, 2003.

TECHNICAL FIELD OF THE INVENTION

The present invention relates to a novel isoquinoline compound and a pharmaceutical agent containing same as an active ingredient.

BACKGROUND ART

Poly(ADP-ribose)polymerase, hereinafter sometimes to be abbreviated as "PARP", is an intranuclear enzyme that utilizes nicotinamide nucleotide (NAD) as a substrate, cleaves the bond between nicotinamide and ribose, transfers ADP-ribose residue into a protein, and causes addition polymerization of plural ADP-ribose residues. This enzyme is attractive as an apoptosis-related enzyme, which is considered to be activated by recognizing the nick of DNA damaged by a free radical, such as nitrogen monoxide, active oxygen and the like, which is produced in the lesion during ischemia, and have a primary role to aid DNA repair.

It is considered in recent years that the activation of PARP decreases intracellular NAD, a large amount of ATP is consumed to compensate fox the decrease, as a result of which intracellular energy is depleted, and the cell is driven to death. In an experiment using a PARP knockout mouse, it has been clarified that a cultured nerve cells show resistance to disorders due to excitatory amino acids, such as nitrogen monoxide, NMDA (N-methyl-D-aspartate) and the like, and that it shows a tremendous protective effect by inhibiting cerebral infarction caused by cerebral ischemia by not less than 80% (Eliasson MJL. et al., Nature Med., 3, 1089-95 (1997)).

However, none of the reported PARP inhibitors to date has subjected to a clinical trial as a therapeutic agent for cerebral infarction. As the reported PARP inhibitors to date, for example, 5-substituted-3,4-dihydro-2H-isoquinoline derivatives (JP-A-H2-124874), 1,11b-dihydrobenzopyrano[4.3.2-de]isoquinolin-3-one derivatives (WO99/11645), 3,4-dihydro-5-[4-(1-piperidinyl)-butoxy]-1(2H)-isoquinoline (each of WO99/08680 and WO99/11649), pyrimidine derivatives (WO00/42025), benzimidazole derivatives (each of WO00/64878 and WO00/68206), phthalazine derivatives (each of WO00/67734 and WO00/44726), quinazolinone derivatives (each of WO02/48117 and WO02/44157) and the like are known, but the PARP inhibitory activity thereof is not very strong.

Moreover, JP-B-S46-12454 discloses isoquinoline derivatives having an analgesic action and a hypoglycemic action, U.S. Pat. Nos. 1,174,272 and 1,062,357 respectively disclose quinazoline derivatives having a hypotensive action, GB Patent Nos. 1174272 and 1062357 and DE Patent No. 2121031 respectively disclose quinazoline derivatives having a hypotensive action, U.S. Pat. No. 4,808,595 discloses furopyridine derivatives having an intraocular pressure lowering action, and JP-A-S64-42472 discloses quinazoline derivatives having a cerebral dysfunction improving action, but none of these takes note of the PARP inhibitory action.

SUMMARY OF THE INVENTION

An object of the present invention is to provide a compound having a PARP inhibitory action and useful as a therapeutic agent fox cerebral infarction, particularly a therapeutic agent for acute cerebral infarction, and a compound useful as an intermediate.

The present inventors have conducted intensive studies and found that an isoquinoline compound represented by the following formula (I), an optically active form thereof, a pharmaceutically acceptable salt thereof, a hydrate thereof and a water adduct thereof have potent PARP inhibitory action, which resulted in the completion of the present invention.

Accordingly, the present invention provides the following.

1. An isoquinoline compound represented by the following formula (I):

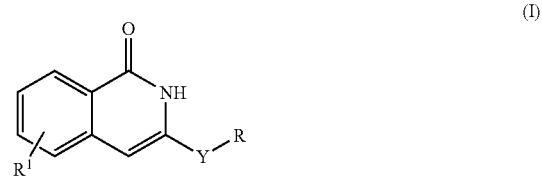

(I)

wherein
$R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;
Y is absent or an alkylene chain having 1 to 8 carbon atoms wherein an optional carbon atom may have a hydroxyl group; and
R is represented by the following formula (II):

(II)

wherein
X is CH or a nitrogen atom, provided that when Y is absent in the formula (I), then X should be CH;
W is CH or a nitrogen atom, provided that when X is CH, then W should be a nitrogen atom;
s is an integer of 1 to 5:
t is an integer of 1 to 5;
when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, $R^2$ is a hydrogen atom, alkyl, a hydroxyl group or hydroxyalkyl and Eel is a hydroxyl group, hydroxyalkyl or alkoxyalkyl; and
when $R^3$ is hydroxyalkyl, $R^2$ and $R^2$, are the same or different and each is a hydrogen atom, a hydroxyl group, alkyl, hydroxyalkyl, alkoxycarbonyl, diakylaminoalkyl or dialkylcarbamoyl, or $R^2$ and $R^2$, are taken together to form ketone, 2. The isoquinoline compound of the above-mentioned 1, which is represented by the formula (I), wherein
$R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;
Y is absent or an alkylene chain having 1 to 8 carbon atoms wherein an optional carbon atom may have a hydroxyl group; and
R is represented by the formula (II),
wherein, in the formula (II),
X is CH or a nitrogen atom, provided that when Y is absent in the formula (I), then X should be CH;
W is CH or a nitrogen atom, provided that when X is CH, then W should be a nitrogen atom;
s is an integer of 1 to 5;
t is an integer of 1 to 5;
when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, $R^2$ and $R^2$, are the same or different and each is a hydroxyl group or hydroxyalkyl; and
when $R^3$ is hydroxyalkyl, $R^2$ and $R^2$, are the same or different and each is a hydrogen atom, a hydroxyl group, alkyl, hydroxyalkyl, alkoxycarbonyl, dialkylaminoalkyl or dialkylcarbamoyl, or $R^2$ and $R^2$, are taken together to form ketone, an optically active form thereof, a pharmaceutically acceptable salt thereof, a water adduct thereof, a hydrate thereof and a solvate thereof.

3. The isoquinoline compound of the above-mentioned 1, which is represented by the formula (I), wherein
$R^1$ is a hydrogen atom or alkyl;
Y is absent or an alkylene chain having 1 to 5 carbon atoms wherein an optional carbon atom may have a hydroxyl group; and
R is represented by the formula (II),
wherein, in the formula (II),
X is CH or a nitrogen atom, provided that when Y is absent in the formula (I), then X should be CH;
W is CH or a nitrogen atom, provided that when X is CH, then W should be a nitrogen atom;
s is a integer of 1 to 5;
t is an integer of 1 to 5;
when $R^3$ is a hydrogen atom or alkyl, $R^2$ is a hydrogen atom, alkyl, a hydroxyl group or hydroxyalkyl and $R^2$, is a hydroxyl group, hydroxyalkyl or alkoxyalkyl; and
when $R^3$ is hydroxyalkyl, $R^2$ and $R^2$, are the same or different and each is a hydrogen atom, a hydroxyl group, alkyl or hydroxyalkyl, an optically active form thereof, a pharmaceutically acceptable salt thereof, a water adduct thereof, a hydrate thereof or a solvate thereof.

4. The isoquinoline compound of the above-mentioned 1, which is represented by the formula (I), wherein
$R^1$ is a hydrogen atom or alkyl;
Y is absent or an alkylene chain having 1 to 5 carbon atoms wherein an optional carbon atom may have a hydroxyl group; and R is represented by the formula (II),
wherein, in the formula (II),
X is CH or a nitrogen atom, provided that when Y is absent in the formula (I), then X should be CH;
W is CH or a nitrogen atom, provided that when x is CH, then W should be a nitrogen atom;
s is an integer of 1 to 5;
t is an integer of 1 to 5;
when $R^3$ is a hydrogen atom or alkyl, $R^2$ and $R^2$, are the same or different and each is a hydroxyl group or hydroxyalkyl; and
when $R^3$ is hydroxyalkyl, $R^2$ and $R^2$, are the same or different and each is a hydrogen atom, a hydroxyl group, alkyl or hydroxyalkyl, an optically active form thereof, a pharmaceutically acceptable salt thereof, a water adduct thereof, a hydrate thereof or a solvate thereof.

5. The isoquinoline compound of the above-mentioned 1, which is represented by the formula (I), wherein
$R^1$ is a hydrogen atom or methyl;
Y is absent, methylene, ethylene, propylene or 2-hydroxypropylene; and
R is represented by the formula (II),
wherein, in the formula (II),
X is CH or a nitrogen atom, provided that when Y is absent in the formula (I), then X should be CH;
W is CH or a nitrogen atom, provided that when X is CH, then W should be a nitrogen atom;
s is an integer of 1 to 3;
t is an integer of 1 to 4;
when $R^3$ is a hydrogen atom or methyl, $R^2$ is a hydrogen atom, methyl, ethyl, a hydroxyl group, hydroxymethyl or 2-hydroxyethyl and $R^2$, is a hydroxyl group, hydroxymethyl, 2-hydroxyethyl, methoxymethyl, ethoxymethyl, propoxymethyl or isopropoxymethyl; and
when $R^3$ is 2-hydroxyethyl, 3-hydroxypropyl, 4-hydroxybutyl or 2-hydroxypropyl, $R^2$ and $R^2$, are the same or different and each is a hydrogen atom, hydroxyl group, methyl, hydroxymethyl or 2-hydroxyethyl, an optically active form thereof, a pharmaceutically acceptable salt thereof, a water adduct thereof, a hydrate thereof or a solvate thereof 6. The isoquinoline compound of the above-mentioned 1, which is represented by the formula (I), wherein
$R^1$ is a hydrogen atom or methyl;
Y is absent, methylene, ethylene, propylene or 2-hydroxypropylene; and
R is represented by the formula (II),
wherein, in the formula (IX),
X is CH or a nitrogen atom, provided that when Y is absent in the formula (I), then X should be CH;
W is CH or a nitrogen atom, provided that when X is CH, then W should be a nitrogen atom;
s is an integer of 1 to 3;
t is an integer of 1 to 4;
when $R^3$ is a hydrogen atom or methyl, $R^2$ and $R^2$, are the same or different and each is a hydroxyl group, hydroxymethyl or 2-hydroxyethyl; and
when $R^3$ is 2-hydroxyethyl, 3-hydroxypropyl, 4-hydroxybutyl or 2-hydroxypropyl, $R^2$ and $R^2$, are the same or different and each is a hydrogen atom, hydroxyl group, methyl, hydroxymethyl or 2-hydroxyethyl, an optically active form thereof, a pharmaceutically acceptable salt thereof, a water adduct thereof, a hydrate thereof or a solvate thereof.

7. The isoquinoline compound of the above-mentioned 1, which is selected from
(1a) (R)-3-[2-(3-hydroxypyrrolidin-1-yl)ethyl]-5-methyl-2H-isoquinolin-1-one,
(2a) 3-[1-(2-hydronyethyl)piperidin-4-yl]-5-methyl-2H-isoquinolin-1-one,
(3a) 3-[3-(3-hydroxypyrrolidin-1-yl)propyl]-2H-isoquinolin-1-one,
(4a) 3-[3-(3-hydroxypyrrolidin-1-yl)propyl]-5-methyl-2H-isoquinolin-1-one,
(5a) 3-[2-(3-hydroxypyrrolidin-1-yl)ethyl]-5-methyl-2H-isoquinolin-1-one,
(6a) 3-[2-(3-hydroxypyrrolidin-1-yl)ethyl]-2H-isoquinolin-1-one,
(7a) 3-[2-(2-hydroxymethylpiperidin-1-yl)ethyl]-5-methyl-2H-isoquinolin-1-one,
(8a) 3-[2-(2-hydroxymethyl)piperidin-1-yl)ethyl]-2H-isoquinolin-1-one,
(9a) 3-[1-(2-hydroxyethyl)piperidin-4-yl]-2H-isoquinolin-1-one,
(10a) 3-[1-(3-hydroxypropyl)piperidin-4-yl]-2H-isoquinolin-1-one,
(11a) 3-[(1-(4-hydroxybutyl)piperidin-4-yl]-2H-isoquinolin-1-one,
(14a) (S)-3-[2-(2-hydroxymethylpyrrolidin-1-yl)ethyl]-5-methyl-2H-isoquinolin-1-one,
(15a) (S)-3-[2-(2-hydroxymethylpyrrolidin-1-yl)ethyl]-2H-isoquinolin-1-one,
(16a) (S)-3-[3-(2-hydroxymethylpyrrolidin-1-yl)propyl]-5-methyl-2H-isoquinolin-1-one,
(17a) (S)-3-[3-(2-hydroxymethylpyrrolidin-1-yl)propyl]-2H-isoquinolin-1-one,
(18a) (R)-3-[3-(2-hydroxymethylpyrrolidin-1-yl)propyl]-2H-isoquinolin-1-one,
(19a) 3-[2-(4-hydroxypiperidin-1-yl)ethyl]-2H-isoquinolin-1-one,
(20a) (R)-3-[2-(2-hydroxymethylpyrrolidin-1-yl)ethyl]-2H-isoquinolin-1-one,
(21a) 3-(1-methyl-2-hydroxymethylpiperidin-4-yl)-2H-isoquinolin-1-one,
(22a) 3-[1-(3-hydroxy-2,2-dimethylpropyl)piperidin-4-yl]-2H-isoquinolin-1-one,
(23a) 5-methyl-3-[1-(3-hydroxypropyl)piperidin-4-yl]-2H-isoquinolin-1-one,
(24a) 3-[1-(2-hydroxypropyl)piperidin-4-yl]-2H-isoquinolin-1-one,
(25a) 3-[2-(4-hydroxypiperidin-1-yl)ethyl]-5-methyl-2H-isoquinolin-1-one,
(26a) (R)-3-[3-(2-hydroxymethylpyrrolidin-1-yl)propyl]-5-methyl-2H-isoquinolin-1-one,
(27a) 3-[2-(3-hydroxypiperidin-1-yl)ethyl]-2H-isoquinolin-1-one,
(28a) 3-[1-(2-hydroxyethyl)pyrrolidin-3-yl]-5-methyl-2H-isoquinolin-1-one,
(29a) 3-[1-(2-hydroxyethyl)pyrrolidin-3-yl]-2H-isoquinolin-1-one,
(30a) 5-methyl-3-[1-(2-hydroxypropyl)piperidin-4-yl]-2H-isoquinolin-1-one,
(31a) 5-methyl-3-[1-(4-hydroxybutyl)piperidin-4-yl]-2H-isoquinolin-1-one,
(32a) 3-[2-(3-hydroxypiperidin-1-yl)ethyl]-5-methyl-2H-isoquinolin-1-one,
(33a) 3-[1-(3-hydroxypropyl)pyrrolidin-3-yl]-5-methyl-2H-isoquinolin-1-one,
(34a) (S)-3-[2-(3-hydroxypyrrolidin-1-yl)ethyl]-5-methyl-2H-isoquinolin-1-one,
(35a) (R)-3-[2-(3-hydroxypiperidin-1-yl)ethyl]-5-methyl-2H-isoquinolin-1-one,
(36a) (R)-3-[2-(2-hydroxymethylpyrrolidin-1-yl)ethyl]-5-methyl-2H-isoquinolin-1-one,
(37a) (−)-3-[1-(2-hydroxylethyl)pyrrolidin-3-yl]-5-methyl-2H-isoquinolin-1-one, and
(38a) (+)-3-[1-(2-hydroxylethyl)pyrrolidin-3-yl]-5-methyl-2H-isoquinolin-1-one, an optically active form thereof, a pharmaceutically acceptable salt thereof, a hydrate thereof or a water adduct thereof.

8. The isoquinoline compound of the above-mentioned 1, which is selected from
(1b) 3-[2-(3,5-dimethyl-2-hydroxymethylpyrrolidin-1-yl)ethyl]-5-methyl-2H-isoquinolin-1-one,
(10b) 3-{2-[(2R,4s)-4-hydroxy-2-hydroxymethylpyrrolidin-1-yl]ethyl)-5-methyl-2H-isoquinolin-1-one,
(11b) 3-(2-[(2R,4R)-4-hydroxy-2-hydroxymethylpyrrolidin-1-yl]ethyl}-5-methyl-2H-isoquinolin-1-one,
(16b) (R)-5-fluoro-3-[2-(2-hydroxymethylpyrrolidin-1-yl)ethyl]-2H-isoquinolin-1-one,
(17b) (R)-5-chloro-3-[2-(2-hydroxymethylpyrrolidin-1-yl)ethyl]-2H-isoquinolin-1-one,
(18b) (R)-5-fluoro-3-[2-(3-hydroxypyrrolidin-1-yl)ethyl]-2H-isoquinolin-1-one,
(19b) (R)-5-chloro-3-[2-(3-hydroxypyrrolidin-1-yl)ethyl]-2H-isoquinolin-1-one,
(20b) (R)-5-methyl-3-[2-(2-methoxmethylpyrrolidin-1-yl)ethyl]-2H-isoquinolin-1-one hydrochloride,
(21b)-(R)-5-chloro-3-[2-(2-methoxymethylpyrrolidin-1-yl)ethyl]-2H-isoquinolin-1-one hydrochloride,
(22b) (R)-S-fluoro-3-[2-(2-methoxymethylpyrrolidin-1-yl)ethyl]-2H-isoquinolin-1-one hydrochloride,
(23b) (R)-3-[2-(2-ethoxymethylpyrrolidin-1-yl)ethyl]-5-methyl-2H-isoquinolin-1-one hydrochloride,
(24b) (R)-5-chloro-3-[2-(2-ethoxymethylpyrrolidin-1-yl)ethyl]-2H-isoquinolin-1-one hydrochloride, and
(25b) (R)-3-[2-(2 ethoxymethylpyrrolidin-1-yl)ethyl]-5-fluoro-2H-isoquinolin-1-one hydrochloride, an optically active form thereof, a pharmaceutically acceptable salt thereof, a hydrate thereof or a water adduct thereof.

9. The isoquinoline compound of the above-mentioned 1, which is represented by the formula (I), wherein
$R^1$ is a hydrogen atom or methyl;
Y is absent; and
R is represented by the formula (II),
  wherein, in the formula (II),
  X is CH;
  W is a nitrogen atom;
  s is an integer of 1 or 2;
  t is an integer of 2,
  when $R^3$ is methyl, $R^2$ is a hydrogen atom, methyl, ethyl, a hydroxyl group or hydroxymethyl and $R^2$, is a hydroxyl group, hydroxymethyl, methoxymethyl, ethoxymethyl, propoxymethyl or isopropoxymethyl; and
  when $R^3$ is hydroxyethyl, $R^2$ and $R^2$, are the same or different and each is a hydrogen atom, a hydroxyl group or hydroxymethyl, an optically active form thereof, a pharmaceutically acceptable salt thereof, a water adduct thereof, a hydrate thereof or a solvate thereof.

10. The isoquinoline compound of the above-mentioned 1, which is represented by the formula (I), wherein
$R^1$ is a hydrogen atom or methyl;
Y is absent; and
R is represented by the formula (II)
  wherein, in the formula (II),
  X is CH;
  W is a nitrogen atom;
  s is an integer of 1 or 2;
  t is an integer of 2;
  when $R^3$ is methyl, $R^2$ and $R^2$, are the same or different and each is a hydroxyl group or hydroxymethyl; and
  when $R^3$ is hydroxyethyl, $R^2$ and $R^2$, are the same or different and each is a hydrogen atom, a hydroxyl group or hydroxymethyl, an optically active form thereof, a pharmaceutically acceptable salt thereof, a water adduct thereof, a hydrate thereof or a solvate thereof.

11. The isoquinoline compound of the above-mentioned 1, which is selected from
(2a) 3-[1-(2-hydroxyethyl)piperidin-4-yl]-5-methyl-2H-isoquinolin-1-one
(9a) 3-[1-(2-hydroxyethyl)piperidin-4-yl]-2H-isoquinolin-1-one
(10a) 3-[1-(3-hydroxypropyl)piperidin-4-yl]-2H-isoquinolin-1-one
(11a) 3-[1-(4-hydroxybutyl)piperidin-4-yl]-2H-isoquinolin-1-one
(21a) 3-(1-methyl-2-hydroxymethylpiperidin-4-yl)-2H-isoquinolin-1-one
(22a) 3-[1-(3-hydroxy-2,2-dimethylpropyl)piperidin-4-yl]-2H-isoquinolin-1-one
(23a) 5-methyl-3-[1-(3-hydroxypropyl)piperidin-4-yl]-2H-isoquinolin-1-one
(24a) 3-[1-(2-hydroxypropyl)piperidin-4-yl]-2H-isoquinolin-1-one
(28a) 3-[1-(2-hydroxyethyl)pyrrolidin-3-yl]-5-methyl-2H-isoquinolin-1-one
(29a) 3-[1-(2-hydxoxyethyl)pyrrolidin-3-yl]-2H-isoquinolin-1-one
(30a) 5-methyl-3-[1-(2-hydroxypropyl)piperidin-4-yl]-2H-isoquinolin-1-one
(31a) 5-methyl-3-[1-(4-hydroxybutyl)piperidin-4-yl]-2H-isoquinolin-1-one
(33a) 3-[1-(3-hydroxypropyl)pyrrolidin-3-yl]-5-methyl-2H-isoquinolin-1-one
(37a) (−)-3-[1-(2-hydroxylethyl)pyrrolidin-3-yl]-5-methyl-2R-isoquinolin-1-one and
(38a) (+)-3-[1-(2-hydroxylethyl)pyrrolidin-3-yl]-5-methyl-2H-isoquinolin-1-one, an optically active form thereof, a pharmaceutically acceptable salt thereof, a water adduct thereof, a hydrate thereof or a solvate thereof.

12. The isoquinoline compound of the above-mentioned 1, which is represented by the formula (I), wherein
$R^1$ is a hydrogen atom or methyl;
Y is ethylene or propylene; and
R is represented by the formula (II),
  wherein, in the formula (II),
  X is a nitrogen atom;
  W is CH;
  s is an integer of 1 to 3;
  t is an integer of 1 to 4;
    $R^2$ is a hydrogen atom, alkyl, a hydroxyl group or hydroxymethyl and $R^2$, is a hydroxyl group, hydroxymethyl, methoxymethyl, ethoxymethyl, propoxymethyl or isopropoxymethyl; and
    $R^3$ is a hydrogen atom, an optically active form thereof, a pharmaceutically acceptable salt thereof, a water adduct thereof, a hydrate thereof or a solvate thereof.

13. The isoquinoline compound of the above-mentioned 1, which is selected from
(1a) (R)-3-[2-(3-hydroxypyrrolidin-1-yl)ethyl]-5-methyl-2H-isoquinolin-1-one,
(3a) 3-[3-(3-hydroxypyrrolidin-1-yl)propyl]-2H-isoquinolin-1-one,
(4a) 3-[3-(3-hydroxypyrrolidin-1-yl)propyl]-5-methyl-2H-isoquinolin-1-one,
(5a) 3-[2-(3-hydroxypyrrolidin-1-yl)ethyl]-5-methyl-2H-isoquinolin-1-one,
(6a) 3-[2-(3-hydroxypyrrolidin-1-yl)ethyl]-2H-isoquinolin-1-one,
(7a) 3-[2-(2-hydroxymethylpiperidin-1-yl)ethyl]-5-methyl-2H-isoquinolin-1-one,
(8a) 3-[2-(2-hydroxymethylpiperidin-1-yl)ethyl]-2H-isoquinolin-1-one,
(14a) (S)-3-[2-(2-hydroxymethylpyrrolidin-1-yl)ethyl]-5-methyl-2H-isoquinolin-1-one,
(15a) (S)-3-[2-(2-hydroxymethylpyrrolidin-1-yl)ethyl]-2H-isoquinolin-1-one,
(16a) (S)-3-[3-(2-hydroxymethylpyrrolidin-1-yl)propyl]-S-methyl-2H-isoquinolin-1-one,
(17a) (S)-3-[3-(2-hydroxymethylpyrrolidin-1-yl) propyl]-2H-isoquinolin-1-one,
(18a) (R)-3-[3-(2-hydroxymethylpyrrolidin-1-yl)propyl]-2H-isoquinolin-1-one,
(19a) 3-[2-(4-hydroxypiperidin-1-yl)ethyl]-2H-isoquinolin-1-one,
(20a) (R)-3-[2-(2-hydroxymethylpyrrolidin-1-yl)ethyl]-2H-isoquinolin-1-one,
(25a) 3-[2-(4-hydroxypiperidin-1-yl)ethyl]-5-methyl-2H-isoquinolin-1-one,
(26a) (R)-3-[3-(2-hydroxymethylpyrrolidin-1-yl)propyl]-5-methyl-2H-isoquinolin-1-one,
(27a) 3-[2-(3-hydroxypiperidin-1-yl)ethyl]-2H-isoquinolin-1-one,
(32a) 3-[2-(3-hydroxypiperidin-1-yl)ethyl]-5-methyl-2H-isoquinolin-1-one,
(34a) (S)-3-[2-(3-hydroxypyrrolidin-1-yl)ethyl]-5-methyl-2H-isoquinolin-1-one,
(35a) (R)-3-[2-(3-hydroxypiperidin-1-yl)ethyl]-5-methyl-2H-isoquinolin-1-one, and
(36a) (R)-3-[2-(2-hydroxymethylpyrrolidin-1-yl)ethyl]-5-methyl-2H-isoquinolin-1-one, an optically active form thereof, a pharmaceutically acceptable salt thereof, a water adduct thereof, a hydrate thereof or a solvate thereof.

14. The isoquinoline compound of the above-mentioned 1, which is selected from
(10b) 3-{2-[(2R,4S)-4-hydroxy-2-hydroxymethylpyrrolidin-1-yl]ethyl}-5-methyl-2H-isoquinolin-1-one,
(11b) 3-{2-[(2R,4R-4-hydroxy-2-hydroxymethylpyrrolidin-1-yl]ethyl}-5-methyl-2H-isoquinolin-1-one,
(16b) (R)-5-fluoro-3-[2-(2-hydroxymethylpyrrolidin-1-yl)ethyl]-2H-isoquinolin-1-one,
(17b) (R)-5-chloro-3-[2-(2-hydroxymethylpyrrolidin-1-yl)ethyl]-2H-isoquinolin-1-one,
(18b) (R)-5-fluoro-3-[2-(3-hydroxypyrrolidin-1-yl)ethyl]-2H-isoquinolin-1-one,
(19b) (B)-5-chloro-3-[2-(3-hydroxypyrrolidin-1-yl)ethyl]-2H-isoquinolin-1-one,
(20b) (R)-5-methyl-3-[2-(2-methoxymethylpyrrolidin 1-yl) ethyl]-2-isoquinolin-1-one hydrochloride, (21b) (R)-5-chloro-3-[2-(2-methoxymethylpyrrolidin-1-yl) ethyl]-2H-isoquinolin-1-one hydrochloride,
(22b) (R)-5-fluoro-3-[2-(2-methoxymethylpyrrolidin-1-yl1)ethyl]-2H-isoquinolin-1-one hydrochloride,
(23b) (R)-3-[2-(2-ethoxymethylpyrrolidin-1-yl)ethyl]-5-methyl-2H-isoquinolin-1-one hydrochloride,
(24b) (R)-5-chloro-3-[2-(2-ethoxymethylpyrrolidin-1-yl) ethyl]-2H-isoquinolin-1-one hydrochloride, and
(25b) (R)-3-[2-(2-ethoxymethylpyrrolidin-1-yl)ethyl]-5-fluoro-2H-isoquinolin-1-one hydrochloride, an optically active form thereof, a pharmaceutically acceptable salt thereof, a water adduct thereof, a hydrate thereof or a solvate thereof.

15. The isoquinoline compound of the above-mentioned 1, which is represented by the formula (I), wherein
$R^1$ is a hydrogen atom or methyl;
Y is absent or ethylene;
R is represented by the formula (II),
  wherein, in the formula (II),
    when Y is present in the formula (I), X is a nitrogen atom; when Y is absent in the formula (I), X is CH;
    W is CH or a nitrogen atom, provided that when X is CH, then W should be a nitrogen atom;
    s is an integer of 1 or 2;
    t is an integer of 1 to 3;
    when $R^3$ is a hydrogen atom, $R^1$ is a hydrogen atom, a hydroxyl group or hydroxymethyl and $R^2$, is a hydroxyl group, hydroxymethyl, methoxymethyl, ethoxymethyl, propoxymethyl or isopropoxyethyl; and
    when $R^3$ is hydroxyethyl, $R^1$ and $R^2$, are each a hydrogen atom, a hydroxyl group or hydroxymethyl, an optically active form thereof, a pharmaceutically acceptable salt thereof, a water adduct thereof, a hydrate thereof or a solvate thereof.

16. The isoquinoline compound of the above-mentioned 1, which is represented by the formula (I), wherein
$R^1$ is a hydrogen atom or methyl;
Y is absent or ethylene;
R is represented by the formula (II),
  wherein, in the formula (II)
    when Y is present in the formula (I), X is a nitrogen atom; when Y is absent in the formula (I) X is CH;
    W is CH or a nitrogen atom, provided that when X is CH, then W should be a nitrogen atom;
    s is an integer of 1 or 2;
    t is an integer of 1 to 3;
    when $R^3$ is a hydrogen atom, $R^2$ and $R^2$, are each a hydroxyl group or hydroxymethyl; and
    when $R^3$ is hydroxyethyl, $R^2$ and $R^2$, are each a hydrogen atom, a hydroxyl group or hydroxymethyl, an optically active form thereof, a pharmaceutically acceptable salt thereof, a water adduct thereof, a hydrate thereof or a solvate thereof.

17. The isoquinoline compound of the above-mentioned 1, which is selected from
(1a) (R)-3-[2-(3-hydroxypyrrolidin-1-yl)ethyl]-5-methyl-2H-isoquinolin-1-one,
(2a) 3-[1-(2-hydroxyethyl)piperidin-4-yl]-5-methyl-2H-isoquinolin-1-one,
(5a) 3-[2-(3-hydroxypyrrolidin-1-yl)ethyl]-5-methyl-2H-isoquinolin-1-one,
(28a) 3-[1-(2-hydroxyethyl)pyrrolidin-3-yl]-5-methyl-2H-isoquinolin-1-one,
(34a) (S)-3-[2-(3-hydroxypyrrolidin-1-yl)ethyl]-5-methyl-2H-isoquinolin-1-one,
(36a) (R)-3-[2-(2-hydroxymethylpyrrolidin-1-yl)ethyl]-5-methyl-2H-isoquinolin-1-one,
(37a) (−)-3-[1-(2-hydroxyethyl)pyrrolidin-3-yl]-5-methyl-2H-isoquinolin-1-one, and
(38a) (+)-3-[1-(2-hydroxyethyl)pyrrolidin-3-yl]-5-methyl-2H-isoquinolin-1-one, an optically active form thereof, a pharmaceutically acceptable salt thereof, a water adduct thereof, a hydrate thereof or a solvate thereof.

18. The isoquinoline compound of the above-mentioned 1, which is represented by the formula (I), wherein,
$R^2$ is methyl;
Y is absent; and
R is represented by the formula (II),
  wherein
    x is CH;
    W is a nitrogen atom;
    S is 1 or 2;
    t is an integer of 2;
    $R^2$ and $R^2$, are the same or different and each is a hydrogen atom, a hydroxyl group or hydroxyalkyl; and
    $R^3$ is hydroxethyl, an optically active form thereof, a pharmaceutically acceptable salt thereof, a water adduct thereof, a hydrate thereof or a solvate thereof.

19. The isoquinoline compound of the above-mentioned 1, which is
(2a) 3-[1-(2-Hydroxyethyl)piperidin-4-yl]-5-methyl-2H-isoquinolin-1-one, an optically active form thereof, a pharmaceutically acceptable salt thereof, a water adduct thereof, a hydrate thereof or a solvate thereof.

20. The isoquinoline compound of the above-mentioned 1, which is
(28a) 3-[1-(2-Hydroxyethyl)pyrrolidin-3-yl]-5-methyl-2H-isoquinolin-1-one, an optically active form thereof, a pharmaceutically acceptable salt thereof, a water adduct thereof, a hydrate thereof or a solvate thereof.

21. The isoquinoline compound of the above-mentioned 1, which is
(37a) (+)-3-[1-(2-Hydroxyethyl)pyrrolidin-3-yl]-5-methyl-2H-isoquinolin-1-one, a pharmaceutically acceptable salt thereof, a water adduct thereof, a hydrate thereof or a solvate thereof.

22. The isoquinoline compound of the above-mentioned 1, which is
(38a) (−)-3-[1-(2-Hydroxyethyl)pyrrolidin-3-yl]-5-methyl-2H-isoquinolin-1-one, a pharmaceutically acceptable salt thereof, a water adduct thereof, a hydrate thereof or a solvate thereof.

23. The isoquinoline compound of the above-mentioned 1, which is represented by the formula (I), wherein
$R^1$ is methyl;
Y is ethylene;
R is represented by the formula (II),
  wherein, in the formula (II),
    X is a nitrogen atom,
    W is CH;
    S is 1;
    t is an integer of 2 or 3;

$R^2$ is a hydrogen atom, a hydroxyl group or hydroxymethyl and $R^2$, is a hydroxyl group, hydroxymethyl, methoxymethyl, ethoxymethyl, propoxymethyl or isopropoxymethyl; and
$R^3$ is a hydrogen atom,
an optically active form thereof, a pharmaceutically acceptable salt thereof, a water adduct thereof, a hydrate thereof or a solvate thereof.

24. An isoquinoline compound represented by the formula (I'):

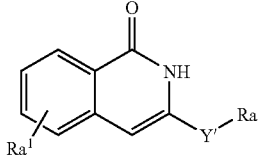

wherein
$Ra^1$ is a hydrogen atom or methyl;
Y' is ethylene, propylene or 2-hydroxypropylene; and
Ra is represented by the formula (II'):

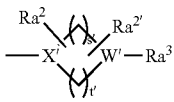

wherein, in the formula (II'),
X' is a nitrogen atom;
W' is CH;
s' is an integer of 1 to 3;
t' is an integer of 1 to 4;
$Ra^2$ and $Ra^2$, are the same or different and each is a hydrogen atom, a hydroxyl group, alkyl or hydroxymethyl; and
$Ra^3$ is a hydrogen atom,
provided that when $Ra^2$ is a hydrogen atom or alkyl,
$Ra^2$, is a hydroxyl group or hydroxymethyl,
an optically active form thereof, a pharmaceutically acceptable salt thereof, a water adduct thereof, a hydrate thereof or a solvate thereof.

25. The isoquinoline compound of the above-mentioned 24, which is represented by the formula (I'), wherein
$Ra^1$ is methyl;
Y' is ethylene;
Ra is represented by the formula (II'),
wherein, in the formula (II'),
X' is a nitrogen atom;
W' is CH;
s' is 1;
t' is an integer of 2 or 3;
$Ra^2$ and $Ra^2$, are the same or different and each is a hydrogen atom, a hydroxyl group or hydroxymethyl; and
$Ra^3$ is a hydrogen atom, provided that when $Ra^2$ is a hydrogen atom, then $Ra^2$, should be
a hydroxyl group or hydroxymethyl,
an optically active form thereof, a pharmaceutically acceptable salt thereof, a water adduct thereof, a hydrate thereof or a solvate thereof.

26. The isoquinoline compound of the above-mentioned 1, which is
(1a) (R)-3-[2-(3-Hydroxypyrrolidin-1-yl)ethyl]-5-methyl-2H-isoquinolin-1-one, a pharmaceutically acceptable salt thereof, a water adduct thereof, a hydrate thereof or a solvate thereof.

27. The isoquinoline compound of the above-mentioned 1, which is
(5a) 3-[2-(3-Hydroxypyrrolidin-1-yl)ethyl]-5-methyl-2H-isoquinolin-1-one, a pharmaceutically acceptable salt thereof, a water adduct thereof, a hydrate thereof or a solvate thereof.

28. The isoquinoline compound of the above-mentioned 1, which is
(34a) (S)-3-[2-(3-Hydroxypyrrolidin-1-yl)ethyl]-5-methyl-2H-isoquinolin-1-one, a pharmaceutically acceptable salt thereof, a water adduct thereof, a hydrate thereof or a solvate thereof.

29. The isoquinoline compound of the above-mentioned 1, which is
(36a) (R)-3-[2-(2-Hydroxymethylpyrrolidin-1-yl)ethyl]-5-methyl-2H-isoquinolin-1-one, a pharmaceutically acceptable salt thereof, a water adduct thereof, a hydrate thereof or a solvate thereof.

30. An isoquinoline compound, which is selected from
(12a) 3-[2-hydroxy-3-(pyrrolidin-1-yl)propyl]-2H-isoquinolin-1-one, and
(13a) 3-[2-hydroxy-3-(pyrrolidin-1-yl)propyl]-5-methyl-2H-isoquinolin-1-one,
an optically active form thereof, a pharmaceutically acceptable salt thereof, a hydrate thereof or a water adduct thereof.

31. An agent for the prophylaxis and/or treatment of a disease caused by hyperactivity of poly(ADP-ribose)polymerase, which comprises the isoquinoline compound of any of the above-mentioned 1, 24 and 30, an optically active form thereof, a pharmaceutically acceptable salt thereof, a water adduct thereof, a hydrate thereof or a solvate thereof.

32. The agent of the above-mentioned 31, which is used for the prophylaxis and/or treatment of cerebral infarction.

33. The agent of the above-mentioned 31, which is used for the prophylaxis and/or treatment of acute cerebral infarction.

34. The agent of the above-mentioned 31, which improves neurological symptoms associated with cerebral infarction.

35. An agent for the prophylaxis and/or treatment of cerebral infarction, which comprises the isoquinoline compound of any of the above-mentioned 1, 24 and 30, an optically active form thereof, a pharmaceutically acceptable salt thereof, a water adduct thereof, a hydrate thereof or a solvate thereof.

36. The agent of the above-mentioned 35, which is used for the prophylaxis and/or treatment of acute cerebral infarction.

37. The agent of the above-mentioned 35, which improves neurological symptoms associated with cerebral infarction.

38. A poly(ADP-ribose)polymerase inhibitor comprising the isoquinoline compound any of the above-mentioned 1, 24 and 30, an optically active form thereof, a pharmaceutically acceptable salt thereof, a water adduct thereof, a hydrate thereof or a solvate thereof.

39. A compound selected from the following:
(R)-3-(3-hydroxypyrrolidin-1-yl)-N-methyl-N-methoxypropanamide (R)-N,N-diethyl-2-[4-(3-hydroxypyrrolidin-1-yl)-2-oxobutyl]-3-methylbenzamide, (R)-3-[2-(3-hydroxypyrrolidin-1-yl)ethyl]-5-methylisocoumarin (R)-3-(2-hydroxymethylpyrrolidin-1-yl)-N-methyl-N-methoxypropanamide, (R)-N,N-diethyl-2-[4-(2-hydroxymethylpyrrolidin-1-yl)-2-oxobutyl]-3-methylbenzamide, (R)-3-[2-(2-hydroxymethylpyrrolidin-1-yl)ethyl]-5-methylisocoumarin and (R)-3-[2-(2-hydroxymethylpyrrolidin-1-yl)ethyl]-5-methylisocoumarin hydrochloride.

40. A method for producing a compound of the following formula (15):

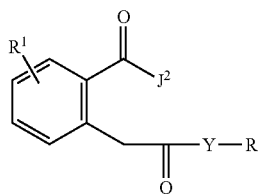

(15)

wherein $R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;

$J^2$ is dialkylamino;

Y is absent or an alkylene chain having 1 to 8 carbon atoms wherein an optional carbon atom may have a hydroxyl group; and R is represented by the following formula (II):

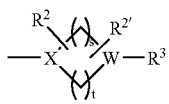

(II)

X is CH or a nitrogen atom, provided that when Y is absent in the formula (I), X is CH;

W is CH or a nitrogen atom; provided that when X is CH, then W should be a nitrogen atom;

s is an integer of 1 to 5;

t is an integer of 1 to 5;

when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, $R^2$ is a hydrogen atom, alkyl, a hydroxyl group or hydroxyalkyl and $R^2$, is a hydroxyl group, hydroxyalkyl or, alkoxyalkyl; and when $R^3$ is hydroxyalkyl, $R^2$ and $R^2$, are the same or different and each is a hydrogen atom, a hydroxyl group, alkyl, hydroxyalkyl, alkoxycarbonyl, dialkylaminoalkyl or dialkylcarbamoyl, or $R^2$ and $R^2$, are taken together to form ketone, which comprises reacting a compound of the following formula (11'):

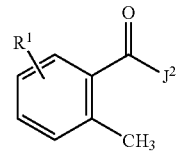

(11')

wherein $R^1$ and $J^2$ are as defined above, with a compound of the following formula (14):

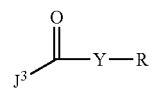

(14)

wherein Y and R are as defined above and $J^3$ is N-alkyl-N-alkoxyamino.

41. The method of the above-mentioned 40, wherein $R^2$ and $R^2$, are the same or different and each is a hydroxyl group or hydroxyalkyl, when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino.

42. A method for producing a compound of the following formula (16):

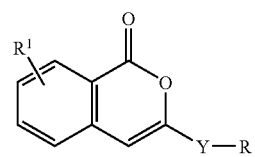

(16)

wherein $R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, Sulfamoyl, N-alkylsulfamoyl, N,N-dialkylsulfamoyl or alkoxyalkyloxy;

Y is absent or an alkylene chain having 1 to 8 carbon atoms wherein an optional carbon atom may have a hydroxyl group; and R is represented by the following formula (II):

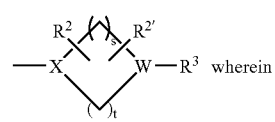

(II) wherein

X is CH or a nitrogen atom, provided that when Y is absent in the formula (I), X is CH;

W is CH or a nitrogen atom, provided that when X is CH, then W should be a nitrogen atom;

s is an integer of 1 to 5;

t is an integer of 1 to 5;

when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, $R^2$ is a hydrogen atom, alkyl, a hydroxyl group or hydroxyalkyl and $R^2$, is a hydroxyl group, hydroxyalkyl or alkoxyalkyl; and when $R^3$ is hydroxyalkyl, $R^2$ and $R^2$, are the same or different and each is a hydrogen atom, a hydroxyl group, alkyl, hydroxyalkyl, alkoxycarbonyl, dialkylaminoalkyl or dialkylcarbamoyl, or $R^2$ and $R^2$, are taken together to form ketone, which comprises using a compound of the following formula (15):

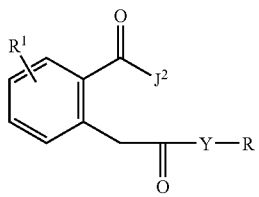

(15)

wherein $J^2$ is dialkylamino, and Rb, Y and R are as defined above

43. The method of the above-mentioned 42, wherein $R^2$ and $R^2$, are the same or different and each is a hydroxyl group or hydroxyalkyl, when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino.

44. A method for producing a compound of the following formula (I):

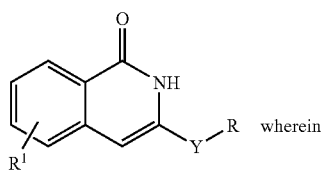

(I)

$R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;

Y is absent or an alkylene chain having 1 to 8 carbon atoms wherein an optional carbon atom may have a hydroxyl group; and R is represented by the following formula (II):

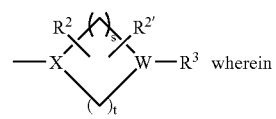

(II)

X is CH or a nitrogen atom, provided that when Y is absent in the formula (I), then X should be CH;

W is CH or a nitrogen atom, provided that when X is CH, then W should be a nitrogen atom;

s is an integer of 1 to 5;

t is an integer of 1 to 5;

when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, $R^2$ is a hydrogen atom, alkyl, a hydroxyl group or hydroxyalkyl and re, is a hydroxyl group, hydroxyalkyl or alkoxyalkyl; and when $R^3$ is hydroxyalkyl, $R^2$ and $R^2$, are the same or different and each is a hydrogen atom, a hydroxyl group, alkyl, hydroxyalkyl, alkoxycarbonyl, dialkylaminoalkyl or dialkylcarbamoyl, or $R^2$ and $R^2$, are taken together to form ketone, which comprises using a compound of the following formula (16):

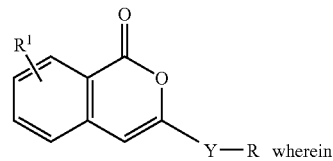

(16)

$R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;

Y is absent or an alkylene chain having 1 to 8 carbon atoms wherein an optional carbon atom may have a hydroxyl group; and R is represented by the following formula (II):

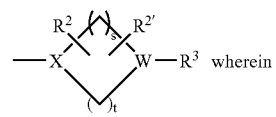

(II)

X is CH or a nitrogen atom, provided that when Y is absent in the formula (I), then X should be CH;

W is CH or a nitrogen atom, provided that when X is CH, then W should be a nitrogen atom;

s as an integer of 1 to 5;

t is an integer of 1 to 5, when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, $R^2$ is a hydrogen atom, alkyl, a hydroxyl group or hydroxyalkyl and $R^2$, is a hydroxyl group, hydroxyalkyl or alkoxyalkyl; and when $R^3$ is hydroxyalkyl, $R^2$ and $R^2$, are the same or different and each is a hydrogen atom, a hydroxyl group, alkyl, hydroxyalkyl, alkoxycarbonyl, dialkylaminoalkyl or dialkylcarbamoyl, or $R^2$ and $R^2$, are taken together to form ketone.

45. The method of the above-mentioned 44, wherein $R^2$ and $R^2$, are the same or different and each is a hydroxyl group or hydroxyalkyl, when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino.

46. A method for producing the isoquinoline compound of the above-mentioned 1, an optically active form thereof, a pharmaceutically acceptable salt thereof, a water adduct thereof, a hydrate thereof and a solvate thereof, which comprises the steps of any of the above-mentioned 40, 42 and 44.

47. A method for producing the isoquinoline compound of the above-mentioned 2, an optically active form thereof, a pharmaceutically acceptable salt thereof, a water adduct thereof, a hydrate thereof and a solvate thereof, which comprises the steps of any of the above-mentioned 41, 43, and 45.

48. A method for producing the isoquinoline compound of the above-mentioned 1, an optically active form thereof, a pharmaceutically acceptable salt thereof, a water adduct thereof, a hydrate thereof or a solvate thereof, which comprises the steps of the above-mentioned 40, 42 and 44.

49. A method for producing the isoquinoline compound of the above-mentioned 2, an optically active form thereof, a pharmaceutically acceptable salt thereof, a water adduct thereof, a hydrate thereof or a solvate thereof, which comprises the steps of the above-mentioned 41, 43 and 45.

DESCRIPTION OF THE PREFERRED EMBODIMENT

The present invention is explained in detail in the following.

The compound of the formula (I) and (I') may be in the form of a tautomer shown by the following formula (III) and (III'). The present invention encompasses both tautomers.

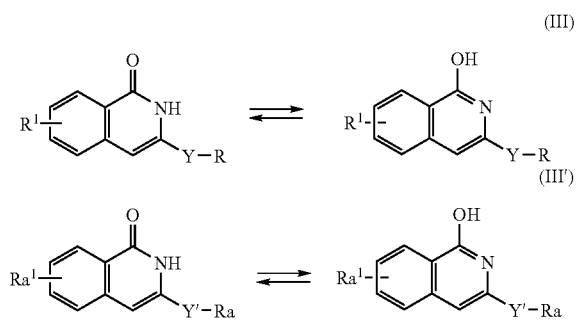

Specific examples of each group in the above-mentioned formula (I) and (I') are as follows.

Specific examples of the substituent for $R^1$ are as follows, which substituent is on any carbon atom in the ring.
halogen atom: fluorine atom, chlorine atom, bromine atom and iodine atom, with preference given to fluorine atom, chlorine atom and bromine atom.
alkyl: linear or branched chain alkyl having 1 to 4 carbon atoms, such as methyl, ethyl, propyl, isopropyl, butyl, isobutyl, tert-butyl and the like, with preference given to methyl.
alkoxy: alkoxyl consisting of alkyl (as defined above) and oxygen atom, such as methoxy, ethoxy, propoxy, isopropoxy, butoxy, tert-butoxy and the like, with preference given to methoxy.
haloalkyl: alkyl (as defined above) substituted by one or more halogen atoms (as defined above), such as fluoromethyl, difluoromethyl, trifluoromethyl, 2-fluoroethyl, 2,2-difluoroethyl, 2,2,2-trifluoroethyl and the like, with preference given to trifluoromethyl.
dialkylamino: dialkylamino wherein the alkyl moieties are the same or different and each independently alkyl (as defined above) and the alkyl moieties may form a ring. For example, dimethylamino, diethylamino, N-methyl-N-ethylamino, pyrrolidin-1-yl, piperidin-1-yl and the like can be mentioned, with preference given to dimethylamino.
acyl: acyl having 1 to 4 carbon atoms in total, which consists of alkyl (as defined above) and carbonyl, such as formyl, acetyl, propionyl, 2-methylpropionyl, butyryl and the like.
alkoxycarbonyl: ester consists of alkoxy (as defined above) and carbonyl, such as methoxycarbonyl, ethoxycarbonyl, propoxycarbonyl, isopropoxycarbonyl, butoxycarbonyl, tert-butoxycarbonyl and the like.
N-alkylcarbamoyl: N-alkylcarbamoyl consisting of monoalkylamino having 1 to 4 carbon atoms and carbonyl, such as N-methylcarbamoyl, N-ethylcarbamoyl, N-propylcarbamoyl, N-butylcarbamoyl and the like.
N,N-dialkylcarbamoyl: N,N-dialkylcarbamoyl consisting of dialkylamino (as defined above) and carbonyl, such as N,N-dimethylcarbamoyl, N,N-diethylcarbamoyl, N,N-dipropylcarbamoyl, N,N-dibutylcarbamoyl and the like.
acylamino: acylamino consisting of acyl (as defined above) and amino, such as formylamino, acetylamino, propionylamino, butyrylamino and the like.
diacylamino: diacyl amino consisting of two acyls (as defined above) and amino, wherein the acyl moieties are independent and may be the same or different, such as N,N-diacetylamino, N,N-dipropionylamino, N,N-dibutyrylamino and the like.
alkylthio: alkylthio consisting of alkyl (as defined above) and sulfur atom, such as methylthio, ethylthio, propylthio, butylthio and the like, with preference given to methylthio.
alkoxycarbonylamino; alkoxycarbonylamino consisting of alkoxycarbonyl (as defined above) and amino, such as methoxycarbonylamino, ethoxycarbonylamino, propoxycarbonylamino, butoxycarbonylamino and the like.
N-alkylsulfamoyl: N-alkylsulfamoyl consisting of monoalkylamino (as defined above) and sulfon, such as N-methylsulfamoyl, N-ethylsulfamoyl, N-propylsulfamoyl, N-butylsulfamoyl and the like.
N,N-dialkylsulfamoyl: N,N-dialkylsulfamoyl consisting of dialkylamino (as defined above) and sulfon, such as N,N-dimethylsulfamoyl N,N-diethylsulfamoyl, N,N-dipropylsulfamoyl, N,N-dibutylsulfamoyl and the like.
alkoxyalkyloxy: alkoxyalkyloxy consisting of alkoxy (as defined above), alkyl (as defined above) and oxygen, wherein alkoxy and alkyl are as defined above, such as methoxymethyloxy, ethoxymethyloxy and the like, with preference given to methoxymethyloxy.

As the substitution site for $R^1$, substitution at the 5-position or 7-position of isoquinoline ring is preferable, particularly the 5-position is preferable.

Y is absent or an alkylene chain having 1 to 8 carbon atoms wherein an optional carbon atom may have a hydroxyl group. For example, (1) —CH(OH) CH$_2$
(2) —CH$_2$CH(OH)CH$_2$—,
(3) —CH$_2$CH$_2$CH(OH)CH$_2$—,
(4) —CH$_2$CH$_2$CH$_2$CH(OH)CH$_2$—,
(5) —CH$_2$CH$_2$CH$_2$CH$_2$CH(OH) CH$_2$—,
(6) —CH$_2$CH$_2$CH$_2$CH$_2$CH$_2$CH(OH)CH$_2$—,
(7) —CH$_2$CH$_2$CH$_2$CH$_2$CH$_2$CH$_2$(OH)CH$_2$—,
(8) —CH$_2$CH(CH$_2$OH)CH$_2$—,
(9) —CH$_2$CH(CH$_2$CH$_2$OH)CH$_2$—, and the like can be mentioned, with preference given to (2). As the linear alkylene chain, ethylene and propylene are preferable.

Specific examples of the substituent for $R^2$, $R^{2'}$, $Ra^2$ and $Ra^{2'}$ are as follows, which substituent is on any carbon atom in the ring.

alkyl: as defined for alkyl for $R^1$.
hydroxyalkyl: hydroxyalkyl consisting of alkyl (as defined for alkyl for $R^1$) and hydroxyl group, with preference given to hydroxymethyl.
alkoxycarbonyl: alkoxycarbonyl consisting of alkoxy (as defined for alkoxy for R) and carbonyl, such as methoxycarbonyl, ethoxycarbonyl, propoxycarbonyl, isopropoxycarbonyl, butoxycarbonyl, tert-butoxycarbonyl and the like, with preference given to ethoxycarbonyl.
dialkylaminoalkyl: dialkylaminoalkyl consisting of dialkylamino (as defined for dialkylamino for $R^1$) and alkyl (as defined for alkyl for $R^1$) with preference given to dimethylaminomethyl.
dialkylcarbamoyl: dialkylcarbamoyl consisting of dialkylamino (as defined for dialkylamino for $R^1$) and carbonyl, with preference given to dimethylcarbamoyl.

Specific examples of the substituent for $R^3$ are as follows.

alkyl: as defined for alkyl for $R^1$, with preference given to methyl, ethyl, propyl and isobutyl, particularly preferably methyl.
hydroxyalkyl: as defined for hydroxyalkyl for $R^2$, such as hydroxymethyl, hydroxyethyl, hydroxypropyl, 2-hydroxy-2-methylpropyl, 4-hydroxybutyl and the like, with preference given to hydroxymethyl, hydroxyethyl, hydroxypropyl, hydxoxybutyl, 2-hydroxypropyl and 2,2-dimethyl-3-hydroxypropyl, particularly preferably hydroxymethyl and hydroxyethyl.
monoalkylamino: as defined for monoalkylamino for $R^1$, with preference given to methylamino.
dialkylamino: as defined for dialkylamino for $R^1$, with preference given to dimethylamino.
alkoxycarbonyl: as defined for alkoxycarbonyl for $R^1$, with preference given to ethoxycarbonyl.
alkylsulfonyl: alkylsulfonyl consisting of alkyl (as defined for alkyl for $R^1$) and sulfonyl, such as methanesulfonyl, ethanesulfonyl and the like.
acyl: as defined for acyl for $R^1$.
acylamino optionally having a substituent: as defined for acylamino for $R^1$, a group consisting of acyl having 1 to 4 carbon atoms and amino group, which is selected from formylamino, acetylamino, propionylamino, 2-methylpropionylamino and butyrylamino. As the substituent, halogen atom (particularly fluorine atom) can be preferably mentioned. For example, trifluoroacetylamino can be mentioned. benzoylamino optionally having a substituent: as the substituent, those similar to the substituents for $R^1$ can be mentioned.

arylalkyl: arylalkyl consisting of aryl and alkyl (as defined for acylamino for $R^1$), such as benzyl, phenethyl and the like, with preference given to benzyl.
alkylsulfonylamino: alkylsulfonylamino consisting of alkylsulfonyl (as defined above) and amino, such as methanesulfonylamino, ethanesulfonylamino and the like, with preference given to methanesulfonylamino.

As the compound of the formula (I) and a pharmaceutically acceptable salt thereof, acid addition salts thereof with inorganic acids or organic acids can be mentioned.

The compound of the formula (I) and a pharmaceutically acceptable salt thereof may be in a form of a water adduct, a hydrate or a solvate thereof, and these water adduct, hydrate and solvate are also encompassed in the present invention. When the compound of the formula (I) has an asymmetric atom, at least two optical isomers are present. These optical isomers and mixtures thereof (including racemate) are encompassed in the present invention.

The compounds encompassed in the formula (I) of the present invention can be synthesized according to the following methods. In the following reaction schemes, each symbol is as defined above unless particularly indicated Synthesis Method 1

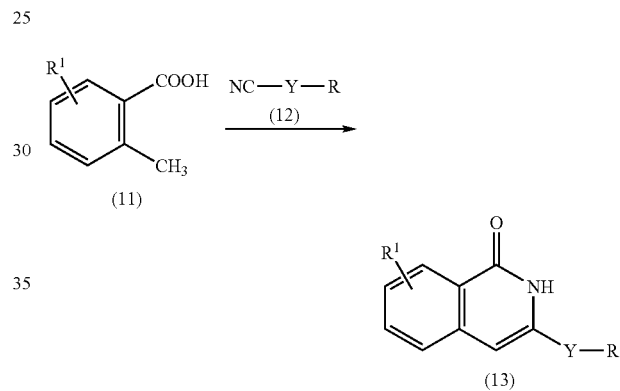

A compound of the formula (11) obtained by a known method is reacted with a compound of the formula (12) obtained by a known method, in the presence of a suitable base generally used in synthetic organic chemistry, such as n-butyllithium, lithium diisopropylamide, lithium diethylamide, lithium bistrimethylsilylamide and the like, in a suitable solvent that does not inhibit the progress of the reaction, such as diethyl ether, diisopropyl ether, tetrahydrofuran, 1,4-dioxane, an optionally mixed solvent thereof and the like, at −78° C. to the reflux temperature of the solvent, preferably at −78° C. to room temperature, for 0.1 (6 min) to 48 hr, preferably 1 hr to 24 hr to give a compound of the formula (13).

Synthesis Method 2

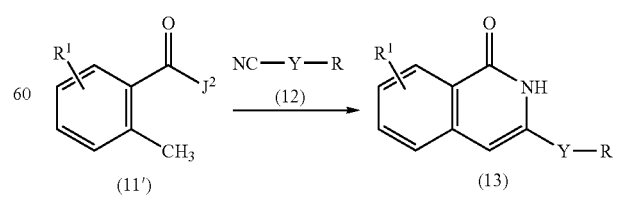

A compound of the formula (13) can be obtained by synthesizing according to the method described in Synthesis Method 1 using a compound of the formula (11') obtained by a known method, wherein $J^2$ is amino, monoalkylamino (as defined for monoalkyl for $R^3$) or dialkylamino (as defined for dialkylamino for $R^3$) and a compound of the formula (12) obtained by a know method.

Synthesis Method 3

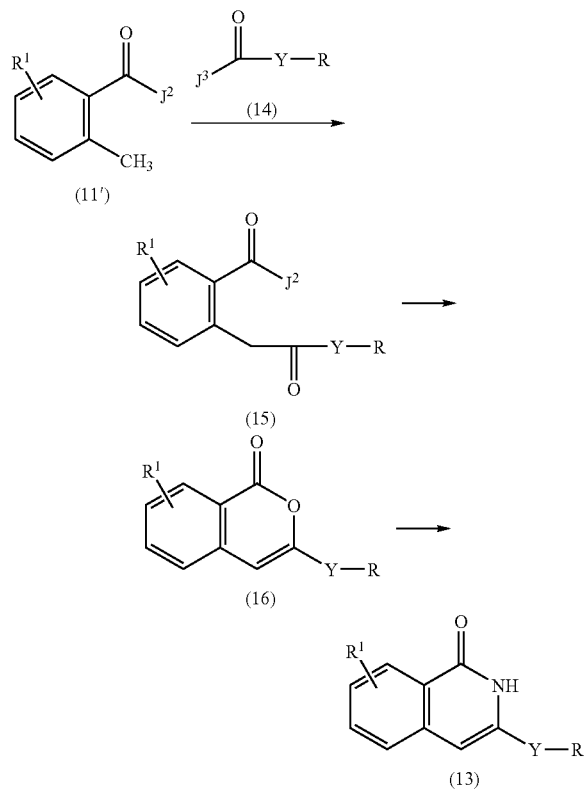

A compound of the formula (11') is reacted with a compound of the formula (14), wherein $J^3$ is N-alkyl-N-alkoxyamino or dialkylamino (as defined for dialkylamino for $R^3$), with preference given to N-methyl-N-methoxyamino in the presence of a suitable base generally used in synthetic organic chemistry, such as n-butyllithium, sec-butyllithium, tert-butyllithium, lithium diisopropylamide, lithium diethylamide, lithium bistrimethylsilylamide and the like, in a suitable solvent mentioned above that does not inhibit the progress of the reaction at −78° C. to the reflux temperature of the solvent for 0.1 (6 min) to 48 hr to give a compound of the formula (15). The compound of the formula (15) is reacted, in acetic acid, trifluoroacetic acid, methanesulfonic acid, hydrochloric acid, sulfuric acid, or an optional mixed solvent thereof, at room temperature to the reflux temperature of the solvent for 0.1 (6 min) to 48 hr to give the compound of the formula (16). The compound of the formula (16) is reacted with an ammonia source (e.g., ammonia salt generally used in synthetic organic chemistry such as ammonium acetate, ammonium carbonate, ammonium chloride, aqueous ammonia solution and the like) in a suitable solvent that does not inhibit the progress of the reaction (methanol, ethanol, n-propanol, isopropanol, n-butanol, dimethoxyethane, 2-methoxyethanol, acetic acid, aqueous ammonia solution, an optional mixed solvent thereof and the like) at room temperature to the re-flux temperature of the solvent for 0.1 (6 min) to 48 hr to give a compound of the formula (13).

The compound of the present invention thus obtained can be isolated or purified according to a conventional method.

The compound of the present invention encompassed in the formula (I) can be also synthesized using the intermediates shown in the following.

For example, (R)-3-(2-hydroxymethylpyrrolidin-1-yl)propionitrile, (R)-3-(3-hydroxypyrrolidin-1-yl)propionitrile, (S)-3-(3-hydroxypyrrolidin-1-yl)propionitrile, (R)-3-(3-hydroxypyrrolidin-1-yl)-N-methyl-N-methoxypropanamide, (R)-N,N-diethyl-2-[4-(3-hydroxypyrrolidin-1-yl)-2-oxobutyl]-3-methylbenzamide, (R)-3-[2-(3-hydroxypyrrolidin-1-yl)ethyl]-5-methylisocoumarin, (R)-3-(2-hydroxymethylpyrrolidin-1-yl)-N-methyl-N-methoxypropanamide, (R)-N,N-diethyl-2-[4-(2-hydroxymethylpyrrolidin-1-yl)-2-oxobutyl]-3-methylbenzamide, (R)-3-[2-(2-hydroxymethylpyrrolidin-1-yl)ethyl]-5-methylisocoumarin and (R)-3-[2-(2-hydroxymethylpyrrolidin-1-yl)ethyl]-5-methylisocoumarin hydrochloride are novel compounds, and are useful as intermediates for synthesizing, of the formula (I) of the present invention, (1) (R)-3-[2-(3-hydroxypyrrolidin-1-yl)ethyl]-5-methyl-2H-isoquinolin-1-one, (34a) (S)-3-[2-(3-hydroxypyrrolidin-1-yl)ethyl]-5-methyl-2H-isoquinolin-1-one and (36a) (R)-3-[2-(2-hydroxymethylpyrrolidin-1-yl)ethyl]-5-methyl-2H-isoquinolin-1-one.

In addition, (1) (R)-3-[2-(3-hydroxypyrrolidin-1-yl)ethyl]-5-methyl-2H-isoquinolin-1-one, (34a) (S)-3-[2-(3-hydroxypyrrolidin-1-yl)ethyl]-5-methyl-2H-isoquinolin-1-one and (36a) (R)-3-[2-(2-hydroxymethylpyrrolidin-1-yl)ethyl]-5-methyl-2H-isoquinolin-1-one of the formula (I) of the present invention can be synthesized by reacting (R)-3-(2-hydroxymethylpyrrolidin-1-yl) propionitrile, (R)-3-(3-hydroxypyrrolidin-1-yl)propionitrile or (S)-3-(3-hydroxypyrrolidin-1-yl)propionitrile with N,N-diethyl-2,3-dimethylbenzamide or N,N-dimethyl-2,3-dimethylbenzamide according to Synthesis Method 1.

The compound of the formula (I), an optical isomer and a pharmaceutically acceptable salt thereof, a water adduct thereof, a hydrate thereof and a solvate thereof obtained by the above-mentioned methods have a potent PARP inhibitory action, and are useful as agents for the prophylactic and/or therapeutic agents that improve cerebral infarction, particularly agents for the prophylaxis and/or treatment of acute cerebral infarction. Moreover, they are useful as prophylactic and/or therapeutic agents that improve neurological symptoms associated with cerebral infarction, particularly acute cerebral infarction. Moreover, the neurological symptoms associated with cerebral infarction, particularly acute cerebral infarction can be evaluated by scoring according to the NIH Stroke Scale (Brott T, et al.; Measurement of acute cerebral infarction: a clinical examination scale. Stroke-vol. 20, pp. 864-870 (1989)) defined by the US National Institute of Health (NIH).

When the isoquinoline compound, an optical isomer thereof, a pharmaceutically acceptable salt thereof, a water adduct thereof, a hydrate thereof or a solvate thereof according to the present invention is used as a pharmaceutical agent, the compound of the present invention can be orally or parenterally administered in the form of a pharmaceutical composition or a preparation (tablet, pill, capsule, granule, powder, syrup, emulsion, elixir, suspension, solution, injection, infusion, suppository and the like) obtained by admixing with a pharmaceutically acceptable carrier (excipient, binder, disintegrant, corrigent, flavor, emulsifier, diluent, dissolution aids and the like). The pharmaceutical composition can be formulated according to a conventional method. In the present specification, parenteral administration includes subcutaneous injection, intravenous injection, intramuscular injection, intraperitoneal injection, dripping and the like. A preparation for injection can be prepared according to a method known in this field. The suppository for rectal administration can be produced by admixing the drug with a suitable excipient and the like. As the dosage form of a solid preparation for oral administration, those mentioned above such as powder, granule, tablet, pill, capsule and the like can be mentioned. As the liquid for oral administration, emulsion, syrup, elixir, suspension, solution and the like acceptable as a pharmaceutical agent can be mentioned.

The dose is determined in consideration of age, body weight, general health condition, sex, diet, administration time, administration method, clearance rate, combination of drugs, the disease state of the patient then under treatment, and other factors. The compound of the present invention, an optical isomer thereof and a pharmaceutically acceptable salt thereof are low toxic and can be used safely. While the daily dose varies depending on the condition and body weight of patient, the kind of the compound, administration route and the like, for example, it is desirably administered parenterally (subcutaneously, intravenously, intramuscularly or rectally) at about 0.01-50 mg/individual/day, preferably 0.01-20 mg/individual/day, and orally at about 0.01-150 mg/individual/day, preferably 0.1-100 mg/individual/day.

EXAMPLES

The present invention is explained in more detail in the following by referring to Examples, which are not to be construed as limitative as long as the spirit of the invention is not deviated. The unit of J is Hz.

Starting Material Synthesis Example 1

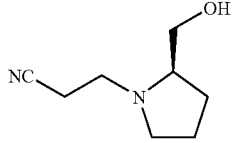

(R)-2-hydroxymethylpyrrolidine (Tokyo Kasei Kogyo Co., Ltd.) (50 g) was dissolved in methylene chloride (500 mL), and acrylonitrile (36 mL) was added dropwise to the solution with stirring at room temperature Subsequently, the mixture was stirred overnight at room temperature. After the completion of the reaction, the solvent was concentrated to give (R)-3-(2-hydroxymethylpyrrolidin-1-yl)propionitrile (76 g).

$^1$H-NMR (CDCl$_3$)δ: 1.61-1.94 (5H, m), 2.33 (1H, q, J=8 Hz), 2.53 (2H, dd, J=6 Hz, 8 Hz), 2.61-2.71 (2H, m), 3.01-3.10 (1H, m), 3.16-3.24 (1H, m), 3.37-3.46 (1H, m), 3.64 (1H, dd, J=3 Hz, 11 Hz)

Starting Material Synthesis Example 2

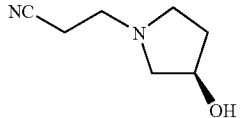

(R)-(−)-3-pyrrolidinol hydrochloride (Tokyo Kasei Kogyo Co., Ltd.) (50 g) and potassium carbonate (55.8 g) were dissolved in a mixed solvent of acetonitrile (500 mL) and water (100 mL), and acrylonitrile (29 mL) was added dropwise to the solution at room temperature. Subsequently, the mixture was stirred overnight at room temperature. After the completion of the reaction, the solvent was concentrated, and the obtained residue was dissolved in water. Potassium carbonate was added to saturation. The mixture was extracted 3 times with chloroform, and the extract was dried over potassium carbonate. The solvent was concentrated, and the obtained residue was purified by silica gel column chromatography (chloroform:methanol=10:1) to give (R)-3-(3-hydroxypyrrolidin-1-yl)propionitrile (53 g).

$^1$H-NMR(CDCl$_3$)δ: 1.68-1.81 (1H, m), 2.04-2.10 (1H, m), 2.13-2.27 (1H, m), 2.34-2.43 (1H, m), 2.51-2.63 (3H, m), 2.72-2.84 (3H, m), 2.91-2.99 (1H, m), 4.30-4.40 (1H, m)

Starting Material Synthesis Example 3

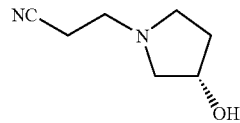

By the reaction in the same manner as in Starting Material Synthesis Example 1 using (S)-(+)-3-pyrrolidinol (12.3 g) and acrylonitrile (10.2 mL), (S)-3-(3-hydroxypyrrolidin-1-yl)propionitrile (53 g) was obtained.

$^1$H-NMR (CDCl$_3$)δ: 1.68-1.81 (1H, m), 2.04-2.10 (1H, m), 2.13-2.27 (1H, m), 2.34-2.43 (1H, m), 2.51-2.63 (3H, m), 2.72-2.84 (3H, m), 2.91-2.99 (1H, m), 4.30-4.40 (1H, m)

Stating Material Synthesis Example 4

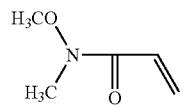

N,O-dimethylhydroxylamine hydrochloride (198.6 g), sodium bicarbonate (620.9 g), methylene chloride (1.5 L) and water (1.1 L) were added, and acryl chloride (150 mL) was added dropwise to the mixture under ice-cooling. The mixture was stirred under ice-cooling for 4 hr, and the methylene chloride layer was separated. The organic layer was dried over magnesium sulfate, and the solvent was concentrated to give N-methyl-N-methoxyacrylamide (223.79 g). This compound was used in the next step without further production.

$^1$H-NMR (CDCl$_3$)δ: 3.27 (3H, s), 3.71 (3H, s), 5.76 (1H, dd, J=2 Hz, 11 Hz), 6.43 (1H, dd, J=2 Hz, 17 Hz), 6.74 (1H, dd, J=11 Hz, 17 Hz)

Starting Material Synthesis Example 5

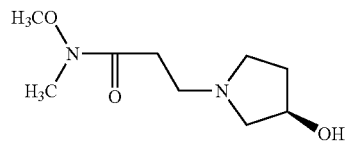

(R)-(−)-3-pyrrolidinol hydrochloride (51.8 g), potassium carbonate (69.6 g), water (125 mL) and acetonitrile (500 mL) were added, and the mixture was stirred at room temperature for 1 hr. A solution (60 mL) of N-methyl-N-methoxyacrylamide (42 g) obtained in Starting Material Synthesis Example 4 in acetonitrile was added dropwise to the mixture, and the reaction was allowed to proceed overnight at room temperature. After the completion of the reaction, acetonitrile was concentrated under reduced pressure, and potassium carbonate was added to the residual aqueous layer to achieve oversaturation. The aqueous layer was extracted with chloroform, the extract was dried over magnesium sulfate and concentrated to give (R)-3-(3-hydroxypyrrolidin-1-yl)-N-methyl-N-methoxypropanamide (76.7 g).

$^1$H-NM(CDCl$_3$)δ: 1.65-1.75 (1H, m); 2.10-2.25 (1H, m), 2.36 (1H, dd, J=8.79 Hz, 15.2 Hz), 2.60-2.70 (4H, m), 2.75-2.80 (2H, m), 2.80-2.90 (3H, m), 3.18 (3H, s), 3.48 (1H, brs), 3.70 (3H, s), 4.33-4.35 (1H, m)

Starting Material Synthesis Example 6

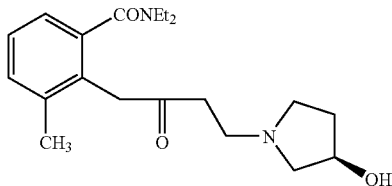

Under a nitrogen stream, diisopropylamine (63.8 mL) and tetrahydrofuran (90 mL) were added, and a solution (1.56 mol/L, 280 mL) of n-butyllithium in hexane was added dropwise to the mixture at −78° C. The mixture was stirred at 0° C. for 30 min. The reaction mixture was cooled to −78° C. and a solution (120 mL) of N,N-diethyl-2,3-dimethylbenzamide (42.5 g) in tetrahydrofuran was added dropwise to the mixture, and the mixture was stirred at −78° C. for 1 hr. Then, a solution (120 mL) of (R)-3-(3-hydroxypyrrolidin-1-yl)-N-methyl-N-methoxypropanamide (38.6 g) obtained in Starting Material Synthesis Example 5 in tetrahydrofuran was added dropwise. The temperature was gradually risen to room temperature, and the reaction was allowed to proceed overnight. After the completion of the reaction, water (200 mL) was added, and tetrahydrofuran was concentrated under reduced pressure. The reaction mixture was extracted with chloroform. The chloroform layer was dried over anhydrous magnesium sulfate and concentrated to give (R)-N,N-diethyl-2-[4-(3-hydroxypyrrolidin-1-yl)-2-oxobutyl]-3-methylbenzamide (79.4 g).

$^1$H-NMR (CDCl$_3$)δ: 1.04 (3H, t, J=7.2 Hz), 1.21 (3H, t, J=7.2 Hz), 1.65-1.80 (1H, m), 2.10-2.30 (2H, m), 2.21 (3H, s), 2.40-2.50 (1H, m), 2.60-2.80 (5H, m), 2.80-2.95 (1H, m), 3.00-3.20 (2H, m), 3.30-3.40 (1H, m), 3.40-3.70 (1H, m), 3.70-4.00 (2H, m), 4.29-4.32 (1H, m), 7.01-7.07 (1H, m), 7.16-7.20 (2H, m)

Starting Material Synthesis Example 7

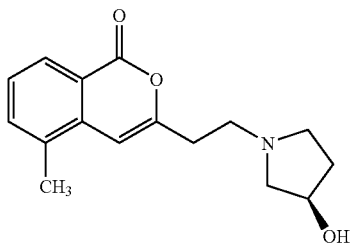

(R)-N,N-diethyl-2-[4-(3-hydroxypyrrolidin-1-yl)-2-oxobutyl]-3-methylbenzamide (124 g) obtained in Starting Material Synthesis Example 6 was dissolved in 25% (v/v) aqueous sulfuric acid solution (600 mL), and the solution was heated under reflux for 12 hr. After completion of the reaction, the reaction mixture was washed with chloroform, and the aqueous layer was alkalified with potassium carbonate. Chloroform was added and insoluble materials were removed by celite filtration. The aqueous layer was extracted with chloroform. The extract was dried over anhydrous magnesium sulfate and concentrated, and the precipitated crystals were washed with diethyl ether-ethyl acetate and collected by filtration by suction to give (R)-3-[2-(3-hydroxypyrrolidin-1-yl)ethyl]-5-methylisocoumarin (55.6 g).

$^1$H-NMR (CDCl$_3$)δ: 1.65-1.80 (1H, m), 2.10-2.25 (1H, m), 2.30-2.40 (1H, m), 2.46 (3H, s), 2.56-2.61 (1H, m), 2.74-2.78 (1H, m), 2.85-2.96 (3H, m), 4.32-4.36 (1H, m), 6.43 (1H, s), 7.34 (3H, t, J=7.5 Hz), 7.51 (1H, d, J=7.5 Hz), 8.12 (1H, d, J=7.5 Hz)

Starting Material Synthesis Example 8

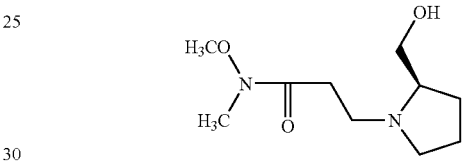

D-prolinol (30 g) and tetrahydrofuran (300 mL) were added, and N-methyl-N-methoxyacrylamide (28.7 g) was added to the mixture with stirring at room temperature. After the completion of the reaction, the reaction mixture was concentrated to quantitatively give (R)-3-(2-hydroxymethylpyrrolidin-1-yl)-N-methyl-N-methoxypropanamide as an oil.

$^1$-NMR (CDCl$_3$)δ: 1.62-1.89 (4H, m), 2.22-2.30 (1H, m), 2.48-2.80 (4H, m), 3.16-3.48 (6H, m), 3.18 (3H, s), 3.65-3.71 (1H, m), 3.70 (3H, s)

Starting Material Synthesis Example 9

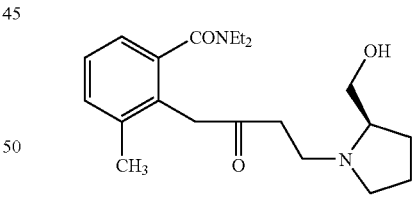

Diisopropylamine (104 mL) and tetrahydrofuran (500 mL) were added, and a solution (457 mL, 1.56 mol/L) of n-butyllithium in hexane was added dropwise to the mixture with stirring at −78° C. under a nitrogen stream. After the completion of the dropwise-addition, the mixture was stirred at 0° C. for 30 min, and cooled to −78° C. again. A solution of N,N-diethyl-2,3-dimethylbenzamide (67.0 g) in tetrahydrofuran (150 mL) was added dropwise to the reaction mixture, After the completion of the dropwise addition, the mixture was further stirred at −78° C. for 1 hr. A solution of (R)-3-(2-hydroxymethylpyrrolidin-1-yl)-N-methyl-N-methoxypropanamide (64 g) obtained in starting Material Synthesis Example 8 in tetrahydrofuran (150 mL) was added dropwise. After the completion of the dropwise addition, the mixture was further stirred at −78° C. for 1 hr. The mixture was gradually heated to room temperature. After the completion of the reaction, ice and water were added to the reaction mixture, and the organic layer was separated. The organic layer was concentrated, combined with the aqueous layer mentioned above, and the combined layer was extracted twice with chloroform. The organic layer was concentrated to give (R)-N,N-diethyl-2-[4-(2-hydroxymethylpyrrolidin-1-yl)-2-oxobutyl]-3-methylbenzamide as an oil. This compound was used in the next reaction without further purification.

$^1$H-NMR (CDCl$_3$)δ: 1.04 (3H, t, J=7 Hz), 1.21 (3H, t, J=7 Hz), 1.62-1.94 (4H, m), 2.12-2.22 (1H, m), 2.21 (3H, s), 2.36-2.44 (1H, m), 2.52-2.63 (2H, m), 2.68-2.82 (1H, m), 2.97-3.24 (5H, m), 3.32-3.40 (2H, m), 3.62-3.90 (4H, m), 7.03-7.08 (1H, m), 7.16-7.20 (2H, m)

Starting Material Synthesis Example 10

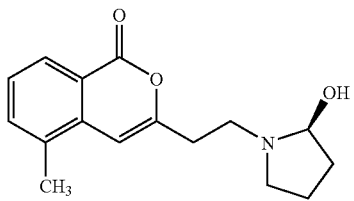

The entire amount of (R)-N,N-diethyl-2-[4-(2-hydroxymethylpyrrolidin-1-yl)-2-oxobutyl]-3-methylbenzamide obtained in Starting Material Synthesis Example 9 was dissolved in conc. hydrochloric acid (250 mL) and water (250 mL), and the solution was heated under reflux for 10 hr. After the completion of the reaction, the reaction mixture was cooled to room temperature and washed with toluene (200 ma). An aqueous solution of potassium carbonate (300 g) was added to the aqueous layer to basify the layer, and the layer was extracted twice with chloroform and the extract was dried over magnesium sulfate. The solvent was concentrated and acetone was added to the obtained residue. The mixture was further concentrated to give (R)-3-[2-(2-hydroxymethylpyrrolidin-1-yl)ethyl]-5-methylisocoumarin (67 g).

$^1$H-NMR (CDCl$_3$)δ: 1.66-1.92 (4H, m), 2.32-2.42 (1H, m), 2.46 (3H, s), 2.65-2.70 (4H, m), 3.12-3.28 (2H, m), 3.38 (1H, dd, J=4 Hz, 11 Hz), 3.64 (1H, dd, J=4 Hz, 11 Hz), 6.43 (1H, s), 7.34 (1H, t, J=8 Hz), 7.51 (1H, d, J=8 Hz), 8.12 (1H, d, J=8 Hz)

Using a known method, (R)-3-[2-(2-hydroxymethylpyrrolidin-1-yl)ethyl]-5-methylisocoumarin was converted to a hydrochloride to give (R)-3-[2-(2-hydroxymethylpyrrolidin-1-yl)ethyl]-5-methylisocoumarin hydrochloride. $^1$H-NMR (DMSO-d$_6$)δ: 1.70-2.18 (4H, m), 2.47 (3H, s), 3.08-3.22 (3H, m), 3.60-3.85 (5H, m), 5.51 (1H, brs), 6.82 (1H, s), 7.47 (1H, t, J=8 Hz), 7:69 (1H, d, J=7 Hz), 7.99 (1H, d, J=8 Hz), 10.31 (1H, brs).

Example 1a

Diisopropylamine (122 mL) was dissolved in tetrahydrofuran (400 mL), and n-butyllithiun (1.56 mol/L) (534 mL) was added dropwise to the solution under ice-cooling. The mixture was stirred under ice-cooling for 30 min, and then cooled to −78° C. A solution (150 mL) of N,N-diethyl-2,3-dimethylbenzamide (85.4 g) in tetrahydrofuran was added dropwise to the reaction mixture and the mixture was stirred at −78° C. for 0.5 hr. The reaction mixture was cooled to −78° C. and a solution (150 mL) of (R)-1-(2-cyanoethyl)-3-hydroxypyrrolidine (53 g) in tetrahydrofuran was added dropwise to the mixture. The reaction mixture was allowed to warm to room temperature. After the completion of the reaction, water was added to the reaction mixture and the organic layer was separated and concentrated. The residue was dissolved in chloroform and the solution was washed with saturated brine and dried over magnesium sulfate. The organic layer was extracted with 1N hydrochloric acid, and the layer was basified. The aqueous layer was extracted with chloroform and the extract was dried over magnesium sulfate. The solvent was concentrated and the obtained residue was purified by silica gel column chromatography to give (R)-3-[2-(3-hydroxypyrrolidin-1-yl)ethyl]-5-methyl-2H-isoquinolin-1-one (23.6 g).

$^1$H-NMR (CDCl$_3$)δ: 1.83-1.95 (1H, m), 2.21-2.32 (1H, m), 2.48 (3H, s), 2.49-2.55 (1H, m), 2.72-2.79 (3H, m), 2.81-2.92 (3H, m), 2.96-3.05 (1H, m), 4.42-4.49 (1H, m), 6.33 (1H, s), 7.29 (1H, t, J=8 Hz), 7.43 (1H, d, J=7 Hz), 8.22 (1H, d, J=8 Hz), 11.40 (1H, brs). MS (EI) 272 (M+)

Using a known method, (R)-3-[2-(3-hydroxypyrrolidin-1-yl)ethyl]-5-methyl-2H-isoquinolin-1-one was converted to a hydrochloride to give (R)-3-[2-(3-hydroxypyrrolidin-1-yl) ethyl]-5-methyl-2H-isoquinolin-1-one hydrochloride.

$^1$H-NMR (DMSO-d$_6$)δ: 1.83-2.00 (1.5H, m), 2.15-2.30 (0.5H, m), 2.43 (3H, m), 2.96-3.10 (2.5H, m), 3.14-3.66 (5.5H, m), 4.37-4.50 (1H, m), 5.55 (1H, brs), 6.52 (0.5H, s), 6.54 (0.5H, s), 7.34 (1H, t, J=8 Hz), 7.53 (1H, d, J=7 Hz), 8.02 (1H, d, J=8 Hz), 10.70 (0.5H, brs), 11.27 (0.5H, brs), 11.43 (0.5H, brs), 11.46 (0.5H, brs). MS (EI) 272 (M+). [α]$_D$=−3.52° (α=1.15, MeOH)

A different synthesis method of (R)-3-[2-(3-hydroxypyrrolidin-1-yl)ethyl]-5-methyl-2H-isoquinolin-1-one is shown in the following.

Ammonium carbonate (65.3 g) was gradually added to acetic acid (165 mL). After bubbling, (R)-3-[2-(3-hydroxypyrrolidin-1-yl)ethyl]-5-methylisocoumarin (54.3 g) was added to the mixture, and the mixture was heated under reflux for 1 hr. After the completion of the reaction, the reaction mixture was cooled to room temperature and added to aqueous sodium hydroxide (115 g) solution (300 mL) (with heat generation and ammonia odor). The mixture was stirred at room temperature for 30 min. After the completion of the reaction, the mixture was extracted with chloroform, the extract was dried over magnesium sulfate, and concentrated. Ethyl acetate was added to the obtained residue and the suspension was washed. Collection by filtration gave (R)-3-[2-(3-hydroxypyrrolidin-1-yl)ethyl]-5-methyl-2H-isoquinolin-1-one (45.1 g).

Example 2a

5-Methyl-3-(piperidin-4-yl)-2H-isoquinolin-1-one (1.0 g, sodium bicarbonate (0.52 g) and 2-bromoethanol (0.67 g) were dissolved in acetonitrile (20 mL) and the solution was heated under reflux. After the completion of the reaction, the reaction mixture was concentrated and water was added to the obtained residue. The mixture was extracted with chloroform, and the extract was dried over magnesium sulfate. The solvent was concentrated and the obtained residue was purified by silica gel column chromatography to give 3-[1-(2-hydroxyethyl)piperidin-4-yl]-5-methyl-2H-isoquinolin-1-one (0.4 g).

$^1$H-NMR (CDCl$_3$)δ: 1.80-1.95 (2H, m), 1.96-2.10 (2H, m), 2.24-2.33 (2H, m), 2.53 (3H, s), 2.56-2.65 (3H, m), 3.05-3.15

(2H, m), 3.67 (2H, t, J=5 Hz), 6.44 (1H, s), 7.34 (1H, t, J=7 Hz), 7.48 (1H, d, J=7 Hz), 8.24 (1H, d, J=7 Hz), 10.72 (1H, brs). MS (EI) 286 (M+)

Example 3a

By the reaction in the same manner as in Example 1a, using N,N-diethyl-2-methylbenzamide (3.45 g) and 4-(3-hydroxypyrrolidin-1-yl)butyronitrile (1.5 g), 3-[3-(3-hydroxypyrrolidin-1-yl)propyl]-2H-isoquinolin-1-one (536.3 mg) was obtained.

$^1$H-NMR (CDCl$_3$)δ: 1.78-1.95 (2H, m), 2.03-2.20 (2H, m), 2.31-2.49 (2H, m), 2.62-2.90 (4H, m), 3.09-3.30 (2H, m), 4.35-4.49 (1H, m), 5.83 (1H, brs), 6.32 (1H, s), 7.35-7.45 (2H, m), 7.56-7.62 (1H, m), 8.34 (1H, d, J=8 Hz), 14.41 (1H, brs) MS (EI) 272 (M+)

Example 4a

By the reaction in the same manner as in Example 1a, using N,N-dimethyl-2,3-dimethylbenzamide (2.00 g) and 4-(3-hydroxypyrrolidin-1-yl)butyronitrile (0.8 g), 3-[3-(3-hydroxypyrrolidin-1-yl)propyl]-5-methyl-2H-isoquinolin-1-one (157.5 mg) was obtained.

$^1$H-NMR (CDCl$_3$)δ: 1.88-2.00 (2H, m), 2.08-2.19 (2H, m), 2.36-2.42 (2H, m), 2.50 (3H, s), 2.62-2.98 (4H, m), 3.16-3.30 (2H, m), 4.39-4.48 (1H, m), 5.86 (1H, brs), 6.43 (1H, s), 7.27-7.32 (1H, m), 7.44 (1H, b, J=7 Hz), 8.22 (1H, b, J=8 Hz), 14.45 (1H, brs) Ms (EI) 286 (M+)

Example 5a

By the reaction in the same manner as in Example 1a, using N,N-dimethyl-2,3-dimethylbenzamide (4.10 g) and 3-(3-hydroxypyrrolidin-1-yl)propionitrile (1.5 g), 3-[2-(3-hydroxypyrrolidin-1-yl)ethyl]-5-methyl-2H-isoquinolin-1-one (157.5 mg) was obtained.

$^1$H-NMR (CDCl$_3$)δ: 1.88-1.99 (1H, m), 2.22-2.38 (1H, m), 2.48-2.57 (4H, m), 2.71-2.95 (6H, m), 3.01-3.10 (1H, m), 3.51 (1H, brs), 4.42-4.51 (1H, m), 6.34 (1H, s), 7.27-7.31 (1H, m), 7.43 (1H, b, J=7 Hz), 8.22 (1H, b, J=8 Hz), 11.42 (1H, brs). MS (EI) 272 (M+)

Example 6a

By the reaction in the same manner as in Example 1a, using N,N-diethyl-2,3-dimethylbenzamide (4.347 g) and 3-(3-hydroxypyrrolidin-1-yl)propionitrile (1.6 g), 3-[2-(3-hydroxypyrrolidin-1-yl)ethyl]-2H-isoquinolin-1-one (397.6 mg) was obtained.

$^1$H-NMR (CDCl$_3$)δ: 1.84-1.97 (1H, m), 2.21-2.37 (1H, m), 2.43-2.55 (1H, m), 2.70-2.82 (3H, m), 2.82-2.95 (3H, m), 3.00-3.11 (1H, m), 4.44-4.50 (1H, m), 6.25 (1H, s), 7.38-7.45 (1H, m), 7.57-7.62 (1H, t, J=7 Hz), 8.34 (1H, d, J=8 Hz), 11.41 (1H, brs) MS (EI) 258 (M+)

Example 7a

By the reaction in the same manner as in Example 1a, using N,N-dimethyl-2,3-dimethylbenzamide (3.17 g) and 3-(2-hydroxymethylpiperidin-1-yl)propionitrile (1.51 g), 3-[2-(2-hydroxymethylpiperidin-1-yl)ethyl]-5-methyl-2H-isoquinolin-1-one (268 mg) was obtained.

$^1$H-NMR (300 MHz, CDCl$_3$)δ: 11.5 (brs, 1H), 8.24 (d, J=8.1, 1H), 7.49 (d, J=8.1, 1H), 7.30 (t, J=8.1, 1H), 6.39 (s, 1H), 3.65-3.80 (m, 2H), 3.30 (brs, 1H), 3.10-3.30 (m, 1H), 3.00-3.10 (m, 1H), 2.85-3.00 (m, 1H), 2.70-2.85 (m, 2H), 2.50 (s, 3H), 2.35-2.60 (m, 2H), 1.30-1.75 (m, 9H). MS (EI) 300 (M+)

Example 8a

By the reaction in the same manner as in Example 1a, using N,N-diethyl-2-methylbenzamide (3.42 g) and 3-(2-hydroxymethylpiperidin-1-yl)propionitrile (1.51 g), 3-[2-(2-hydroxymethylpiperidin-1-yl)ethyl]-2H-isoquinolin-1-one (392 mg) was obtained.

$^1$H-NMR (300 MHz, CDCl$_3$)δ: 11.5 (brs, 1H), 8.36 (d, J=7.8, 1H), 7.60 (t, J=7.8, 1H), 7.39-7.46 (m, 2H), 6.29 (s, 1H), 3.65-3.85 (m, 2H), 3.30 (brs, 1H), 3.10-3.30 (m, 1H), 3.00-3.10 (m, 1H), 2.85-3.00 (m, 1H), 2.70-2.80 (m, 2H), 2.45-2.60 (m, 1H), 2.30-2.45 (m, 1H), 1.30-1.75 (m, 6H). MS (EI) 286 (M+)

Example 9a

By the reaction in the same manner as in Example 2a, using 3-(piperidin-4-yl)-2H-isoquinolin-1-one hydrochloride (1.1 g) and 2-bromoethanol (1.0 g) as starting materials, 3-[1-(2-hydroxyethyl)piperidin-4-yl]-2H-isoquinolin-1-one (0.39 g) was obtained.

$^1$H-NMR (CDCl$_3$)δ: 1.71-1.91 (2H, m), 2.00-2.10 (2H, m), 2.22-2.33 (2H, m), 2.50-2.65 (3H, m), 3.04-3.13 (2H, m), 3.62-3.67 (2H, m), 6.34 (1H, s), 7.42-7.52 (2H, m), 7.61-7.67 (1H, m), 8.34-8.38 (1H, m), 10.69 (1H, brs). MS (EI) 272 (M+)

Example 10a

By the reaction in the same manner as in Example 2a, using 3-(piperidin-4-yl)-2H-isoquinolin-1-one hydrochloride (500 mg) and 3-bromo-1-propanol (315 mg), 3-[1-(3-hydroxypropyl)piperidin-4-yl]-2H-isoquinolin-1-one (136 mg) was obtained.

$^1$H-NMR (270 MHz, DMSO-d$_6$)δ: 1.79-1.91 (4H, m), 2.12-2.17 (2H, m), 2.69-3.02 (5H, m), 3.44-3.52 (5H, m), 6.37 (1H, s), 7.42-7.47 (1H, m), 7.66-7.71 (2H, m), 8.13 (1H, d, J=7.8 Hz), 11.31 (1H, brS). MS (ET) 286 (M+)

Example 11a

By the reaction in the same manner as in Example 21a, using 3-(piperidin-4-yl)-2H-isoquinolin-1-one hydrochloride (500 mg) and 4-bromo-1-butanol (434 mg), 3-[1-(4-hydroxybutyl)piperidin-4-yl]-2H-isoquinolin-1-one (50 mg) was obtained.

$^1$H-NMR (270 MHz, DMSO-d$_6$)δ: 1.44-1.47 (4H, m), 1.57-1.63 (2H, m), 1.88-1.97 (4H, m), 2.27-2.41 (3H, m), 2.95-2.99 (2H, m), 3.40-3.42 (2H, m), 4.55-4.65 (1H, m), 6.36 (1H, s), 7.38-7.43 (1H, m), 7.57-7.65 (2H, m), 8.12 (1H, d, J=7.8 Hz), 11.20 (1H, brS). MS (EI) 300 (M+)

Example 12a

By the reaction in the same manner as in Example 1a, using N,N-diethyl-2-methylbenzamide (1.91 g) and 3-hydroxy-4-(pyrrolidin-1-yl)butyronitrile (1.54 g), 3-[2-hydroxy-3-(pyrrolidin-1-yl)propyl]-2H-isoquinolin-1-one (0.089 g) was obtained.

$^1$H-NMR (CDCl$_3$)δ: 1.75-1.84 (4H, m), 2.32-2.84 (8H, m), 4.00-4.06 (1H, m), 6.26 (1H, s), 7.39-7.46 (2H, m), 7.61 (1H, t, J=8 Hz), 8.36 (1H, d, J=8 Hz), 9.85 (1H, brs). MS (EI) 272 (M+)

Example 13a

By the reaction in the same manner as in Example 1a, using N,N-dimethyl-2,3-dimethylbenzamide (2.65 g) and 3-hydroxy-4-(pyrrolidin-1-yl)butyronitrile (2.31 g), 3-[2-hydroxy-3-(pyrrolidin-1-yl)propyl]-5-methyl-2H-isoquinolin-1-one (0.066 g) was obtained.

$^1$H-NMR (CDCl$_3$)δ: 1.75-1.84 (4H, m), 2.32-2.90 (8H, m), 2.39 (3H, s), 4.06-4.11 (1H, m), 6.36 (1H, s), 7.28 (1H, t, J=8 Hz), 7.42 (1H, d, J=8 Hz), 8.19 (1H, d, J=8 Hz), 10.00 (1H, brs). MS (EI) 286 (M+)

Example 14a

By the reaction in the same manner as in Example 1a, using N,N-dimethyl-2,3-dimethylbenzamide (4.60 g) and (S)-3-(2-hydroxymethyl)pyrrolidin-1-yl)propionitrile (2.01 g), (S)-3-[2-(2-hydroxymethylpyrrolidin-1-yl)ethyl]-5-methyl-2H-isoquinolin-1-one (351 mg) was obtained.

$^1$H-NMR (300 MHz, CDCl$_3$)δ: 12.4 (brs, 1H), 8.23 (d, J=8.1, 1H), 7.45 (d, J=8.1, 1H), 7.31 (t, J=8.1, 1H), 6.39 (s, 1H), 4.10 (brs, 1H), 3.76 (d, J=14.1, 1H), 3.56 (d, J=14.1, 1H), 3.35-3.50 (m, 1H), 3.10-3.25 (m, 1H), 2.85-2.95 (m, 2H), 2.70-2.80 (m, 1H), 2.60-2.70 (m, 1H), 2.50 (s, 3H), 2.40-2.45 (m, 1H), 1.80-2.00 (m, 4H). MS (EI) 286 (M+)

Example 15a

By the reaction in the same manner as in Example 1a, using N,N-diethyl-2-methylbenzamide (4.96 g) and (S)-3-(2-hydroxymethyl)pyrrolidin-1-yl)propionitrile (2.00 g), (S)-3-[2-(2-hydroxymethylpyrrolidin-1-yl)ethyl]-2H-isoquinolin-1-one (515 mg) was obtained.

$^1$H-NMR (300 MHz, CDCl$_3$)δ: 12.4 (brs, 1H), 8.35 (d, J=7.8, 1H), 7.59-7.64 (m, 1H), 7.35-7.50 (m, 2H), 6.28 (s, 1H), 4.06 (brs, 1H), 3.76 (d, J=14.1, 1H), 3.55 (d, J=14.1, 1H), 3.35-3.45 (m, 1H), 3.10-3.25 (m, 1H), 2.80-3.00 (m, 2H), 2.65-2.80 (m, 1H), 2.55-2.65 (m, 1H), 2.35-2.45 (m, 1H), 1.70-2.00 (m, 4H). MS (EI) 272 (M+)

Example 16a

By the reaction in the same manner as in Example 1a, using N,N-dimethyl-2,3-dimethylbenzamide (4.84 g) and (S)-4-(2-hydroxymethyl)pyrrolidin-1-yl)butyronitrile (2.30 g), (S)-3-[3-(2-hydroxymethylpyrrolidin-1-yl)propyl]-5-methyl-2H-isoquinolin-1-one (363 mg) was obtained.

1H-NM (300 MHz, CDCl$_3$) δ: 12.1 (brs, 1H), 8.23 (d, J=8.1, 1H), 7.46 (d, J=8.1, 1H), 7.28-7.34 (m, 1H), 6.44 (s, 1H), 5.16 (brs, 1H), 3.80 (d, J=14.1, 1H), 3.60 (d, J=14.1, 1H), 3.20-3.30 (m, 1H), 2.80-3.00 (m, 2H), 2.60-2.80 (m, 2H), 2.51 (s, 3H), 2.40-2.45 (m, 1H), 2.20-2.35 (m, 1H), 1.70-2.05 (m, 6H). MS (EI) 300 (M+)

Example 17a

By the reaction in the same manner as in Example 1a, using N,N-diethyl-2-methylbenzamide (5.23 g) and (S)-4-(2-hydroxymethyl)pyrrolidin-1-yl)butyronitrile (2.30 g), (S)-3-[3-(2-hydroxymethylpyrrolidin-1-yl)propyl]-2H-isoquinolin-1-one (331 mg) was obtained.

$^1$H-NMR (300 MHz, CDCl$_3$)δ: 12.2 (brs, 1H), 8.34 (d, J=8.1, 1H), 7.59-7.64 (m, 1H), 7.39-7.48 (m, 2H), 6.34 (s, 1H), 5.05 (brs, 1H), 3.80 (d, J=14.1, 1H), 3.60 (d, J=14.1, 1H), 3.15-3.20 (m, 1H), 2.70-2.85 (m, 2H), 2.60-2.70 (m, 2H), 2.40-2.55 (m, 1H), 2.20-2.35 (m, 1H), 1.70-2.10 (m, 6H)

Example 18a

By the reaction in the same manner as in Example 1a, using N,N-diethyl-2,3-dimethylbenzamide (5.0136 g) and (R)-4-(2-hydroxymethylpyrrolidin-1-yl)butyronitrile (2.2 g), (R)-3-[3-(2-hydroxymethylpyrrolidin-1-yl)propyl]-2H-isoquinolin-1-one (627.3 mg) was obtained. 1N aqueous HCl solution (2.4 ml) was added thereto in an acetone solvent, and the precipitated crystals were collected by filtration to give (R)-3-[3-(2-hydroxymethylpyrrolidin-1-yl)propyl]-2-isoquinolin-1-one hydrochloride (555.3 mg).

$^1$H-NMR (CD$_3$OD)δ: 1.83-2.25 (7H, m), 2.68-2.73 (2H, m), 3.08-3.22 (2H, m), 3.43-3.70 (4H, m), 3.85-3.90 (1H, m), 6.54 (1H, s), 7.45-7.50 (1H, m), 7.59 (1H, d, J=8 Hz), 7.70 (1H, t, J=8 Hz), 8.24 (1H, d, J=8 Hz). MS (EI) 286 (M+)

Example 19a

By the reaction in the same manner as in Example 1a, using N,N-diethyl-2,3-dimethylbenzamide (5.6017 g) and 3-(4-hydroxypiperidin-1-yl)propionitrile (2.26 g), 3-[2-(4-hydroxypiperidin-1-yl)ethyl]-2H-isoquinolin-1-one (327.5 mg) was obtained.

$^1$H-NMR (CDCl$_3$)δ: 1.63-1.76 (2H, m), 1.84-2.02 (2H, m), 2.22-2.39 (2H, m), 2.62-2.99 (6H, m), 3.61-3.80 (2H, m), 6.25 (1H, s), 7.36-7.46 (2H, m), 7.57-7.62 (1H, m), 8.30 (1H, d, J=8 Hz), 11.37 (1H, brs). MS (EI) 272 (M+)

Example 20a

By the reaction in the same manner as in Example 1a, using N,N-diethyl-2,3-dimethylbenzamide (4.975 g) and (R)-3-(2-hydroxymethylpyrrolidin-1-yl)propionitrile (2.0 g), (R)-3-[2-(2-hydroxymethylpyrrolidin-1-yl)ethyl]-2H-isoquinolin-1-one (408.4 mg) was obtained $^1$H-NMR (CDCl$_3$)δ: 1.75-2.00 (3H, m), 2.36-2.48 (1H, m), 2.59-2.78 (2H, m), 2.83-2.96 (2H, m), 3.11-3.23 (1H, m), 3.35-4.45 (1H, m), 3.50-3.62 (1H, m), 3.71-3.81 (1H, m), 4.02 (1H, brs); 6.29 (1H, s), 7.39-7.50 (2H, m), 7.58-7.64 (1H, m), 8.35 (1H, d, J=8 Hz), 12.41 (1H, brs). MS (EI) 272 (M+)

Example 21a

To 2-N-t-butoxycarbonyl-4-oxopipecolinic acid (7.96 g) was added dropwise ethyl chloroformate (3.45 ml), in the presence of triethylamine, in tetrahydrofuran under ice-cooling to give a mixed acid anhydride. The precipitated salt was filtered and the filtrate was ice-cooled again. Ethanol (15 ml) was added and the mixture was stirred at room temperature. The reaction mixture was concentrated and ethyl acetate was added. The mixture was washed with 0.5N hydrochloric acid, saturated aqueous sodium hydrogen carbonate and saturated brine, and dried over anhydrous magnesium sulfate. The drying agent was filtered off, and the solvent was concentrated to give ethyl 2-N-t-butoxycarbonyl-4-oxopipecolate (6.39 g).

The obtained ethyl 2-N-t-butoxycarbonyl-4-oxopipecolate (6.39 g) was dissolved in 1,3-dimethyl-2-imidazolidinone and ethanol. Tosylmethyl isocyanide (5.30 g) was added and the mixture was cooled to −78° C. Potassium t-butoxide (6.09 g) was carefully added not to raise the temperature of the reaction mixture, and the mixture was stirred at room temperature. The reaction mixture was concentrated, 10% aqueous citric acid solution was added and the mixture was extracted with chloroform. The chloroform layer was washed with saturated brine and dried over anhydrous magnesium sulfate. The drying agent was filtered off and the solvent was concentrated. The residue was purified by column chromatography (n-hexane:ethyl acetate=4:1) to give ethyl 2-N-t-butoxycarbonyl-4-cyanopipecolate (1.21 g).

The obtained ethyl 2-N-t-butoxycarbonyl-4-cyanopipecolate (1.21 g) was dissolved in tetrahydrofuran and the solution was water-cooled. Lithium borohydride (279 mg) was added and the mixture was stirred at room temperature for 21 hr. Water was added to the reaction mixture and the mixture was extracted with ethyl acetate, the extract was washed with saturated brine, and dried over anhydrous magnesium sulfate. The drying agent was filtered off and the solvent was concentrated to give (N-t-butoxycarbonyl-2-hydroxymethyl-4-cyano)piperidine (961 mg).

By the reaction in the same manner as in Example 1a, using (N-t-butoxycarbonyl-2-hydroxymethyl-4-cyano)piperidine (1.14 g) and N,N-diethyl-2-methylbenzamide (1.84 g), 3-(1-t-butoxycarbonyl-2-hydroxymethylpiperidin-4-yl)-2H-isoquinolin-1-one (616 mg) was obtained.

The obtained 3-(1-t-butoxycarbonyl-2-hydroxymethylpiperidin-4-yl)-2H-isoquinolin-1-one (616 mg) was dissolved in ethyl acetate, and 4N hydrogen chloride-ethyl acetate solution (2.0 ml) was added to the solution, and the mixture was stirred at room temperature for 6.5 hr. The reaction mixture was concentrated, and the precipitated crystals were washed with diethyl ether and dried under reduced pressure to give 3-(2-hydroxymethylpiperidin-4-yl)-2H-isoquinolin-1-one hydrochloride (433 mg).

The obtained 3-(2-hydroxymethylpiperidin-4-yl)-2H-isoquinolin-1-one hydrochloride (433 mg) was dissolved in acetonitrile and water. 35% Formalin (340 μl) and sodium triacetoxy borohydride (697 mg) were added to the solution, and the mixture was stirred at room temperature for 20 min. The reaction mixture was alkalified with 20% aqueous potassium carbonate solution and extracted with chloroform. The chloroform layer was washed with saturated aqueous sodium hydrogen carbonate and saturated brine and dried over anhydrous magnesium sulfate. The drying agent was filtered off, and the solvent was concentrated. The precipitated crystals were washed with diethyl ether and dried under reduced pressure to give 3-(1-methyl-2-hydroxymethylpiperidin-4-yl)-2H-isoquinolin-1-one (146 mg).

$^1$H-NMR (300 MHz, DMSO-d$_6$)δ: 11.1 (brs, 1H), 8.12 (d, J=7.8, 1H), 7.55-7.70 (m, 2H), 7.44 (t, J=7.8, 1H), 6.39 (s, 1H), 4.48 (brs, 1H), 3.55-3.75 (m, 2H), 2.60-2.80 (m, 3H), 2.40-2.60 (m, 1H), 2.42 (s, 3H), 1.70-2.00 (m, 4H). MS (EI) 272 (M+)

Example 22a

By the reaction in the same manner as in Example 2a, using 3-(piperidin-4-yl)-2H-isoquinolin-1-one hydrochloride (510 mg) and 3-bromo-2,2-dimethyl-1-propanol (474 mg), 3-[1-(3-hydroxy-2,2-dim ethylpropyl)piperidin-4-yl]-2H-isoquinolin-1-one (92 mg) was obtained.

$^1$H-NMR (270 MHz, DMSO-d$_6$)δ: 0.79 (6H, s), 1.54-1.63 (2H, m), 1.89-1.93 (2H, m), 2.64-2.65 (1H, m), 2.70-3.00 (2H, m), 3.13-3.20 (2H, m), 3.78-3.79 (2H, m), 4.10-4.14 (2H, m), 4.14-4.60 (1H, m), 6.38 (1H, s), 7.39-7.44 (1H, m), 7.57-7.65 (2H, m) 8.12 (1H, d, J=8.1 Hz), 11.25 (1H, brS). MS (EI) 314 (M+)

Example 23a

By the reaction in the same manner as in Example 2a, using 5-methyl-3-(piperidin-4-yl)-2H-isoquinolin-1-one hydrochloride (1 g) and 3-bromo-1-propanol (751 mg), 5-methyl-3-[1-(3-hydroxypropyl)piperidin-4-yl]-2H-isoquinolin-1-one (221 mg) vas obtained.

melting point: 197-199° C., $^1$H-NMR (270 Hz, DMSO-d$_6$) δ: 1.54-1.69 (4H, m), 1.74-1.96 (4H, m), 2.33-2.38 (2H, m), 2.47-2.50 (3H, m), 2.96-3.00 (2H, m), 3.15-3.18 (1H, m), 3.43-3.48 (2H, m), 4.48-4.49 (1H, m), 6.35 (1H, s), 7.26-7.31 (1H, m), 7.49 (1H, d, J=7.0 Hz), 7.99 (1H, d, J=7.8 Hz), 11.24 (1H, brS). MS (EI) 300 (M+)

Example 24a

By the reaction in the same manner as in Example 2a, using 3-(piperidin-4-yl)-2H-isoquinolin-1-one hydrochloride (500 mg) and 1-bromo-2-propanol (394 mg), 3-[1-(2-hydroxypropyl)piperidin-4-yl]-2H-isoquinolin-1-one (87 mg) was obtained, $^1$H-NM (270 MHz, DMSO-d$_6$)δ: 1.05 (3H, d, J=5.9 Hz), 1.61-1.70 (2H, m), 1.85-1.89 (2H, m), 2.03-2.09 (2H, m), 2.20-2.26 (2H, m), 2.40-2.50 (2H, m), 2.94-2.98 (1H, m), 3.75-3.76 (1H, m), 4.26-4.28 (1H, m), 6.36 (1H, s), 7.38-7.43 (1H, m), 7.57-7.67 (2H, m), 8.11 (1H, d, J=7.8 Hz), 11.20 (1H, brS). MS (EI) 286 (M+)

Example 25a

By the reaction in the same manner as in Example 1a, using N,N-dimethyl-2,3-dimethylbenzamide (5.6095 g) and 3-(4-hydroxypiperidin-1-yl)propionitrile (2.44 g), 3-[2-(4-hydroxypiperidin-1-yl)ethyl]-5-methyl-2H-isoquinolin-1-one (418.2 mg) was obtained.

$^1$H-NMR (CDCl$_3$)δ: 1.71-1.91 (3H, m), 2.01-2.10 (2H, m), 2.30-2.42 (2H, m), 2.49 (3H, s), 2.71-2.79 (4H, m), 2.89-2.98 (2H, m), 3.78-3.85 (1H, m), 6.33 (1H, s), 7.26-7.30 (1H, m), 7.44 (1H, b, J=7 Hz), 8.24 (1H, b, J=8 Hz), 11.38 (1H, brs) MS (EI) 286 (M+)

Example 26a

By the reaction in the same manner as in Example 1a, using N,N-dimethyl-2,3-dimethylbenzamide (5.8040 g) and (R)-4-(2-hydroxymethylpyrrolidin-1-yl)butyronitrile (2.75 g), (R)-3-[3-(2-hydroxymethylpyrrolidin-1-yl)propyl]-5-methyl-2H-isoquinolin-1-one (344.1 mg) was obtained.

melting point: 150.0-151.0° C., $^1$H-NMR (300 MHz, CDCl$_3$)δ: 1.73-2.08 (6H, m), 2.31-2.40 (2H, m), 2.49 (3H, s), 2.70-2.80 (2H, m), 2.85-2.95 (2H, m), 3.75-3.87 (1H, m), 6.34 (1H, s), 7.27-7.32 (1H, m), 7.44 (1H, b, J=7 Hz), 8.23 (1H, b, J=8 Hz), 11.43 (1H, brs)

Example 27a

By the reaction in the same manner as in Example 1a, using N,N-diethyl-2,3-dimethylbenzamide (5.2474 g) and 3-(3-hydroxypiperidin-1-yl)propionitrile (2.62 g), 3-[2-(3-hydroxypiperidin-1-yl)ethyl]-2H-isoquinolin-1-one (888.2 mg) was obtained.

melting point: 192.0-193.0° C., $^1$H-NMR (CDCl$_3$)δ: 1.42-1.53 (1H, m), 1.63-1.71 (1H, m), 1.82-1.91 (2H, m), 2.39-2.40 (2H, m), 2.61-2.76 (5H, m), 2.84-2.91 (1H, m), 3.19-3.21 (1H, m), 3.86-3.98 (1H, m), 6.23 (1H, s), 7.37-7.45 (2H, m), 8.33 (1H, d, J=8 Hz), 11.25 (1H, brs)

Example 28a

By the reaction in the same manner as in Example 2a, using 5-methyl-3-(pyrrolidin-3-yl)-2H-isoquinolin-1-one hydrochloride (200 mg) and 2-bromoethanol (270 μl), 3-[1-(2-hydroxyethyl)pyrrolidin-3-yl]-5-methyl-2H-isoquinolin-1-one (39 mg) was obtained.

$^1$H-NMR (300 MHz, CDCl$_3$)δ: 10.8 (brs, 1H), 8.19 (d, J=8.0, 1H), 7.42 (d, J=8.0, 1H), 7.28 (t, J=8.0, 1H), 6.36 (s, 1H), 3.70-3.85 (m, 2H), 3.10-3.35 (m, 2H), 3.05-3.20 (m, 1H), 2.65-2.85 (m, 2H), 2.55-2.65 (m, 1H), 2.48 (s, 3H), 2.25-2.40 (m, 2H), 1.85-2.00 (m, 1H) MS (ESI) 273 (M+1)

Example 29a

By the reaction in the same manner as in Example 2a, using 3-(pyrrolidin-3-yl)-2H-isoquinolin-1 one hydrochloride (201 mg) and 2-bromoethanol (285 μl), 3-[1-(2-hydroxyethyl)pyrrolidin-3-yl]-2H-isoquinolin-1-one (58 mg) was obtained.

$^1$H-NMR (300 MHz, CDCl$_3$)δ: 10.8 (brs, 1H), 8.32 (d, J=8.1, 1H), 7.57-7.62 (m, 1H), 7.37-7.45 (m, 2H), 6.27 (s, 1H), 3.70-3.80 (m, 2H), 3.15-3.30 (m, 2H), 3.05-3.15 (m, 1H), 2.65-2.80 (m, 2H), 2.55-2.65 (m, 1H), 2.20-2.40 (m, 2H), 1.80-2.00 (m, 1H). MS (ESI) 259 (M+1)

Example 30a

By the reaction in the same manner as in Example 2a, using 5-methyl-3-(piperidin-4-yl)-2H-isoquinolin-1-one hydrochloride (1 g) and 1-bromo-2-propanol (994 mg), 5-methyl-3-[1-(2-hydroxypropyl)piperidin-4-yl]-2H-isoquinolin-1-one (147 mg) was obtained.

$^1$H-NMR (270 MHz, DMSO-d$_6$)δ: 1.05 (3H, d, J=6.2 Hz), 1.68-1.77 (2H, m), 1.85-1.89 (2H, m), 2.04-2.09 (2H, m), 2.15-2.30 (2H, m), 2.39-2.50 (4H, m), 2.95-2.99 (2H, m), 3.77-3.78 (1H, m), 4.23-4.25 (1H, m), 6.34 (1H, s), 7.26-7.32 (1H, m), 7.49 (1H, d, J=7.0 Hz), 7.99 (1H, d, J=7.8 Hz), 11.23 (1H, brS). MS (EI) 300 (M+)

Example 31a

By the reaction in the same manner as in Example 2a, using 5-methyl-3-(piperidin-4-yl)-2H-isoquinolin-1-one hydrochloride (1 g) and 4-bromo-1-butanol (433 mg), 5-methyl-3-[1-(4-hydroxybutyl)piperidin-4-yl]-2H-isoquinolin-1-one (201 mg) was obtained.

$^1$H-NMR (270 MHz, DMSO-d$_6$)δ: 1.44-1.47 (4H, m), 1.61-1.74 (2H, m), 1.74-1.97 (4H, m), 2.26-2.39 (2H, m), 2.43-2.49 (4H, m), 2.95-2.99 (2H, m), 3.33-3.42 (2H, m), 4.37-4.54 (1H, m), 6.34 (1H, s), 7.26-7.32 (1H, m), 7.49 (1H, d, J=7.0 Hz), 7.99 (1H, d, J=8.1 Hz), 11.24 (1H, brS). MS (EI) 314 (M+)

Example 32a

By the reaction in the same manner a: in Example 1a, using N,N-dimethyl-2,3-dimethylbenzamide (5.1101 g) and 3-(3-hydroxypiperidin-1-yl)propionitrile (2.2 g), 3-[2-(3-hydroxypiperidin-1-yl)ethyl]-5-methyl-2H-isoquinolin-1-one (269.6 mg) was obtained.

melting point: 184.0-185.0° C., $^1$H-NMR (300 MHz, CDCl$_3$)δ: 1.49-1.98 (4H, m), 2.36-2.83 (12H, m), 3.90-4.01 (1H, m), 6.33 (1H, s), 7.27-7.32 (1H, m), 7.43 (1H, b, J=7 Hz), 8.22 (1H, b, J=8 Hz), 11.29 (1H, brs). MS (EI) 286 (M+)

Example 33a

By the reaction in the same manner as in Example 2a, using 5-methyl-3-(pyrrolidin-3-yl)-2H-isoquinolin-1-one hydrochloride (501 mg) and 3-bromo-1-propanol (991 μl), 3-[1-(3-hydroxypropyl)pyrrolidin-3-yl]-5-methyl-2H-isoquinolin-1-one (216 mg) was obtained.

$^1$H-NMR (300 MHz, CDCl$_3$)δ: 11.3 (brs, 1H), 8.21 (d, T=7.8, 1H), 7.45 (d, J=7.8, 1H), 7.26-7.33 (m, 1H), 6.37 (s, 1H), 4.80-4.95 (m, 2H), 3.15-3.25 (m, 2H), 3.07 (d, J=9.6, 1H), 2.80-2.90 (m, 1H), 2.60-2.75 (m, 1H), 2.50-2.60 (m, 1H), 2.50 (s, 3H), 2.20-2.40 (m, 2H), 1.75-1.95 (m, 3H). MS (EI) 286 (M+)

Example 34a

By the reaction in the same manner as in Example 1a, using N,N-diethyl-2,3-dimethylbenzamide (4.07 g) and (S)-1-(2-cyanoethyl)-3-hydroxypyrrolidine (1.6 g), (S)-3-[2-(3-hydroxypyrrolidin-1-yl)ethyl]-5-methyl-2H-isoquinolin-1-one (0.228 g) was obtained.

melting point; 176-178° C., $^1$H-NMR (CDCl$_3$)δ: 1.83-1.96 (1H, m), 2.21-2.32 (1H, m), 2.48 (3H, s), 2.49-2.55 (1H, m), 2.72-2.79 (3H, m), 2.81-2.92 (3H, m), 2.96-3.05 (1H, m), 4.42-4.49 (1H, m), 6.33 (1H, s), 7.29 (1H, t, J=8 Hz), 7.43 (1H, d, J=7 Hz), 8.22 (1H, d, J=8 HZ), 11.40 (1H, brs). MS (EI) 272 (M+)

Example 35a

By the reaction in the same manner as in Example 1a, using N,N-dimethyl-2,3-dimethylbenzamide (1.41 g) and (R)-3-(3-hydroxypiperidin-1-yl)propionitrile (1.44 g), (R)-3-[2-(3-hydroxypiperidin-1-yl)ethyl]-5-methyl-2H-isoquinolin-1-one (147 mg) was obtained.

melting point: 180.0-181.0° C., $^1$H-NMR (CDCl$_3$)δ: 1.49-1.98 (4H, m), 2.36-2.83 (12H, m), 3.90-4.01 (1H, m), 6.33 (1H, s), 7.27-7.32 (1H, m), 7.43 (1H, b, J=7 Hz), 8.22 (1H, b, J=8 Hz), 11.29 (1H, brs) MS (EI) 286 (M+)

Example 36a

By the reaction in the same manner as in Example 1a, using N,N-diethyl-2,3-dimethylbenzamide (81.4 g) and (R)-3-(2-hydroxymethylpyrrolidin-1-yl)propionitrile (55.6 g), (R)-3-[2-(2-hydroxymethylpyrrolidin-1-yl)ethyl]-5-methyl-2H-isoquinolin-1-one (12.5 g) was obtained.

$^1$H-NMR (CDCl$_3$)δ: 1.76-1.96 (4H, m), 2.39-2.44 (1H, m), 2.50 (3H, s), 2.62-2.76 (2H, m), 2.85-2.96 (2H, m), 3.11-3.22 (1H, m), 3.38-3.46 (1H, m), 3.55 (1H, dd, J=3 Hz, 11 Hz), 3.76 (1H, dd, J=3 Hz, 12 Hz), 6.39 (1H, s), 7.31 (1H, t, J=8 Hz), 7.55 (1H, d, J=8 Hz), 8.26 (1H, d, J=8 Hz), 12.43 (1H, brs). MS (EI) 286 (M+)

Using a known method, (R)-3-[2-(2-hydroxymethylpyrrolidin-1-yl)ethyl]-5-methyl-2H-isoquinolin-1-one was converted to a hydrochloride to give (R)-3-[2-(2-hydroxymethylpyrrolidin-1-yl)ethyl]-5-methyl-2H-isoquinolin-1-one hydrochloride dihydrate.

$^1$H-NMR (DMSO-d$_6$)δ: 1.69-2.14 (4H, m), 2.48 (3H, s), 2.94-3.44 (4H, m), 3.52-3.84 (5H, m), 5.48 (1H, brs), 6.55 (1H, s), 7.34 (1H, t, J=8 Hz) 7.53 (1H, d, J=7 Hz), 8.02 (1H, d, J=8 Hz), 10.29 (1H; brs), 11.47 (1H, brs). MS (EI) 286 (M+). [α]D=+24.5° (c=1.009, MeOH).

A different synthesis method of (R)-3-[2-(2-hydroxymethylpyrrolidin-1-yl)ethyl]-5-methyl-2H-isoquinolin-1-one is shown in the following.

(R)-3-[2-(2-hydroxymethylpyrrolidin-1-yl)ethyl]-5-methylisocoumarin hydrochloride (62 g) and acetic acid (186 mL) were added and ammonium carbonate (74.4 g) was gradually added to the mixture with stirring. After bubbling, the reaction mixture was heated and stirred at 130° C. for 2 hr with heating. After the completion of the reaction, the reaction mixture was cooled to room temperature and aqueous sodium hydroxide (140 g) solution (200 mL) was added. The mixture was stirred at 80° C., and after the completion of the reaction, the reaction mixture was concentrated. The methanol fraction was evaporated and the mixture was extracted twice with chloroform. The organic layer was extracted twice with 3N hydrochloric acid (300 mL and 100 mL), and potassium carbonate was added to the aqueous layer to basify the layer. The aqueous layer was extracted twice with chloroform, and the extract was dried over magnesium sulfate. The solvent was concentrated and ethyl acetate was added to the obtained residue. The mixture was further concentrated and the residue was dissolved in a small amount of ethyl acetate with heating. Diethyl ether was added to the solution and the precipitated crystals were collected by filtration to give (R)-3-[2-(2-hydroxymethylpyrrolidin-1-yl)ethyl]-5-methyl-2H-isoquinolin-1-one (41.5 g).

Example 37a

A solution (400 mL) of diisopropylamine (26.9 g) in tetrahydrofuran was cooled to −5° C. and 1.57 M n-butyllithium hexane solution (154 ml) was added dropwise to the solution. After stirring at 0° C. for 30 min, the mixture was cooled to −78° C. and a solution (50 mL) of N,N-diethyl-2,3-diethylbenzamide (45.1 g) in tetrahydrofuran was added dropwise. After stirring at −78° C. for 1 hr, a solution (50 mL) of 1-benzyl-3-cyanopyrrolidine (37.18 g) in tetrahydrofuran was added dropwise. After Completion of the dropwise addition, the reaction mixture was heated to room temperature and the mixture was stirred overnight at room temperature. The mixture was further stirred under reflux for 1 hr and the reaction mixture was concentrated to about half. Water and methylene chloride were added and the organic layer was partitioned washed with water, dried over magnesium sulfate and concentrated. The obtained residue was purified by column chromatography (ethyl acetate) to give (±)-3-(1-benzylpyrrolidin-3-yl)-5-methyl-2H-isoquinolin-1-one (66.38 g).

To the obtained (±)-3-(1-benzylpyrrolidin-3-yl)-5-methyl-2H-isoquinolin-1-one (66.38 g) was added D-tartaric acid (31.32 g) in methanol (1580 ml), and the mixture was heated under reflux and cooled to room temperature to give precipitated (±)-3-(1-benzylpyrrolidin-3-yl)-5-methyl-2H-isoquinolin-1-one D-tartrate (44.56 g).

This was further recrystallized twice from methanol to give (−)-3-(1-benzylpyrrolidin-3-yl)-5-methyl-2H-isoquinolin-1-one D-tartrate (27.06 g).

Subsequently, the crystals recovered from the mother liquor of the recrystallization was recrystallized three times from methanol to yield (11.74 g). (−)-3-(1-Benzylpyrrolidin-3-yl)-5-methyl-2H-isoquinolin-1-one D-tartrate (38.8 g) was stirred in methanol (150 ml)-methylene chloride (300 ml), 1N aqueous sodium hydroxide solution (200 ml) and water (100 ml) were added dropwise to alkalify the solution. The methylene chloride layer was partitioned and washed with water, and then dried over magnesium sulfate and concentrated to give (−)-3-(1-benzylpyrrolidin-3-yl)-5-methyl-2H-isoquinolin-1-one (27.5 g).

$[\alpha]_D^{22}$ −101.8 (C=0.998, CHCl$_3$)

To the obtained (−)-3-(1-benzylpyrrolidin-3-yl)-5-methyl-2H-isoquinolin-1-one (27.5 g) were added 50% aqueous lot palladium-carbon (6 g) and ethanol (400 ml), and the mixture was stirred under a hydrogen atmosphere at 50° C. for 6 hr. After celite filtration, the filtrate was concentrated and ethyl acetate was added to the obtained residue. The precipitated crystals were collected by filtration to give (−)-3-(pyrrolidin-3-yl)-5-methyl-2H-isoquinolin-1-one (16.8697 g).

To the obtained (−)-3-(pyrrolidin-3-yl)-5-methyl-2H-isoquinolin-1-one (3.0 g) were added bromoethanol (8.21 g), sodium hydrogen carbonate (5.6 g), methyl ethyl ketone (84 ml) and water (8.4 ml), and the mixture was stirred under reflux for 2 hr. The reaction mixture was concentrated, extracted with methylene chloride, and the extract was washed with water, dried over magnesium sulfate and concentrated. The obtained residue was purified by column chromatography (methanol/ethyl acetate; 2/5) and crystallized from ethyl acetate to give (−)-3-[1-(2-hydroxyethyl)pyrrolidin-3-yl]-5-methyl-2H-isoquinolin-1-one (1.5425 g).

melting point: 137.3-138.6° C., $[\alpha]_D^{22}$ −53.1 (C=1.005, CHCl$_3$), $^1$R-NMR (300 MHz, CDCl$_3$)δ: 1.85-2.01 (1H, m), 2.27-2.42 (2H, m), 2.49 (3H, s), 2.55-2.64 (1H, m), 2.69-2.85 (2H, m), 3.10-3.16 (1H, m), 3.20-3.31 (2H, m), 3.74-3.88 (2H, m), 6.35 (1H, s), 7.23-7.33 (1H, m), 7.43 (1H, d, J=7 Hz), 8.20 (1H, d, J=8 Hz), 10.66 (1H, brs) MS (EI) 272 (M+)

Example 38a

The mother liquor obtained by optical resolution for (−)-3-(1-benzylpyrrolidin-3-yl)-5-methyl-2H-isoquinolin-1-one D-tartrate in Example 37a was subjected to alkali treatment. Conversion to the L-tartrate by a method similar to the above-mentioned and 3 times of recrystallization from methanol gave (+)-3-(1-benzylpyrrolidin-3-yl)-5-methyl-2H-isoquinolin-1-one L-tartrate (38.99 g). Subsequently, desalting, debenzylation and hydroxyethylation in the same manner as in the above gave (+)-3-[1-(2-hydroxylethyl)pyrrolidin-3-yl)-5-methyl-2H-isoquinolin-1-one.

melting point: 137.0-138.6° C., $[\alpha]_D^{22}$ +52.7 (C=1.004, CHCl$_3$), $^1$H-NMR (300 MHz, CDCl$_3$)δ: 1.85-2.01 (1H, m), 2.27-2.42 (2H, m), 2.49 (3H, s), 2.55-2.64 (1H, m), 2.69-2.85 (2H, m), 3.10-3.16 (1H, m), 3.20-3.31 (2H, m), 3.74-3.88 (2H, m), 6.35 (1H, s), 7.23-7.33 (1H, m), 7.43 (1H, d, J=7 Hz), 8.20 (1H, d, J=8 Hz), 10.66 (1H, brs) MS (EI) 272 (M+)

The structural formula of the compound in each Example is shown in the following. The following numbers correspond to the above-mentioned Example numbers.

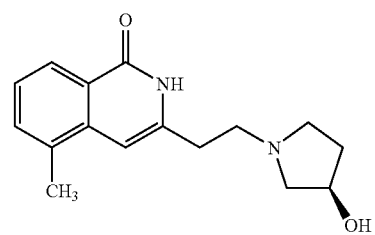

1a

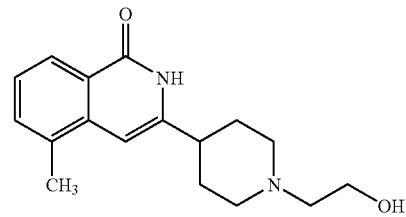

2a

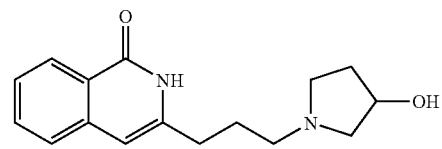

3a

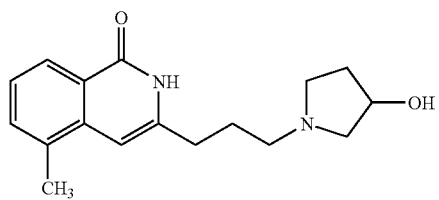
4a
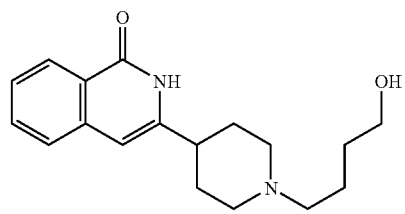
11a
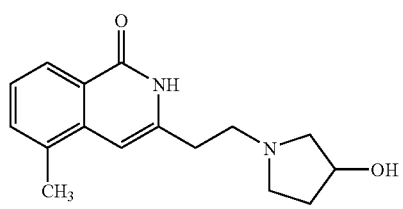
5a
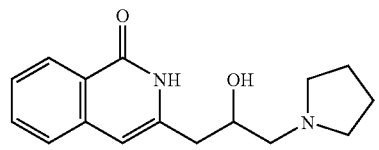
12a
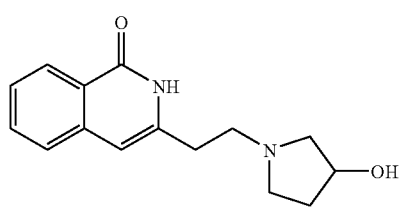
6a
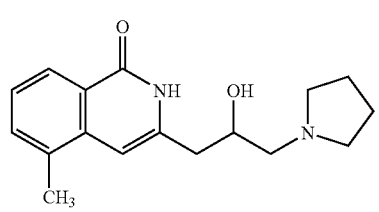
13a
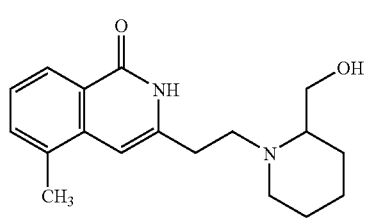
7a
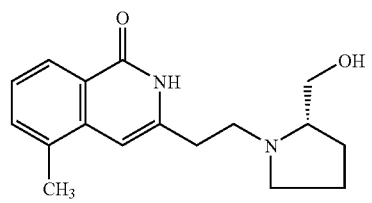
14a
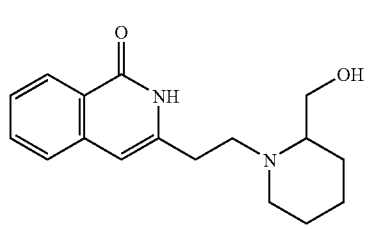
8a
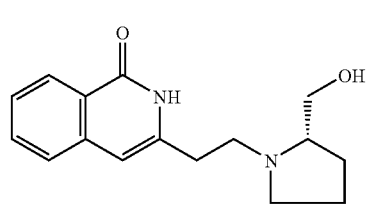
15a
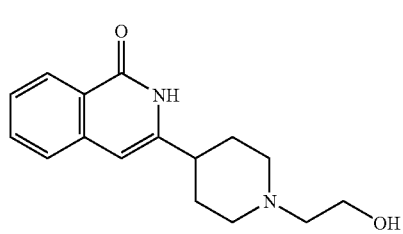
9a
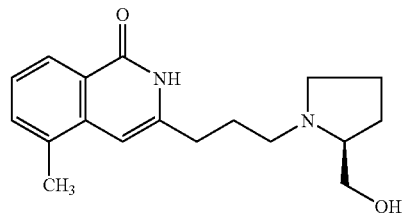
16a
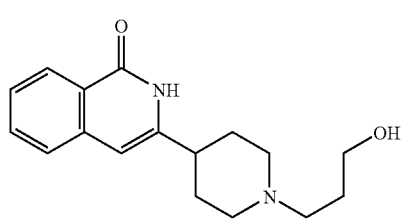
10a
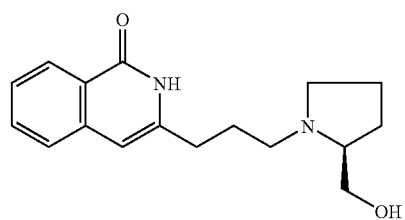
17a 18a
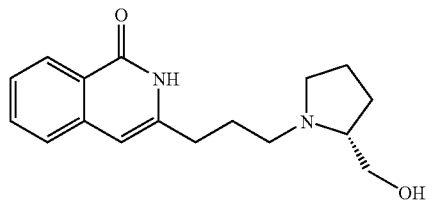
19a
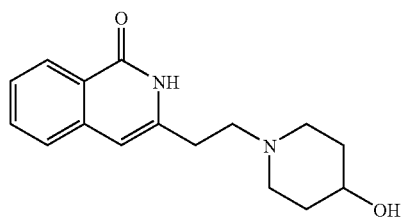
20a
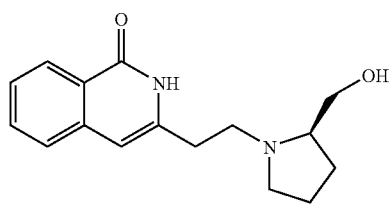
21a
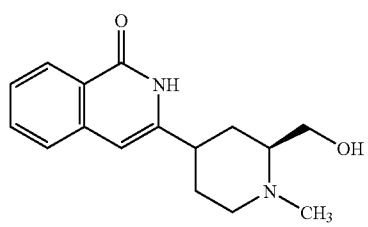
22a
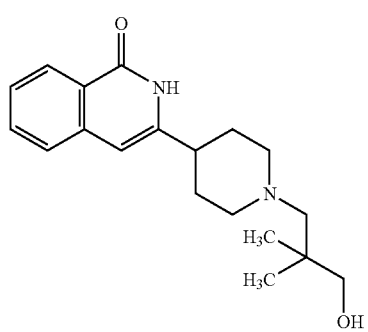
23a
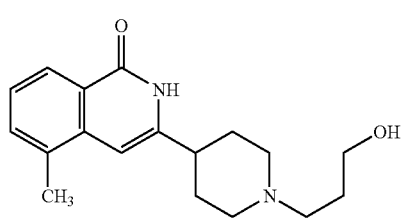
24a
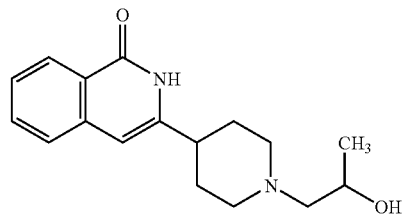
25a
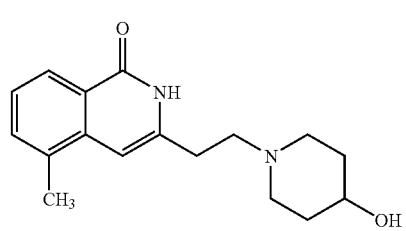
26a
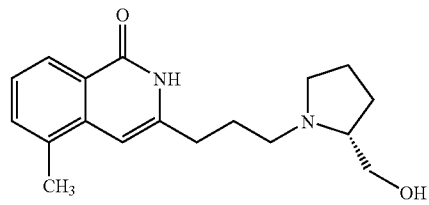
27a
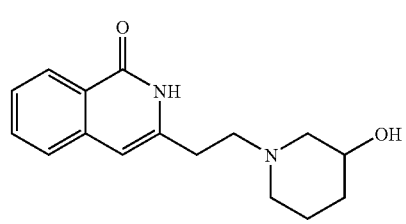
28a
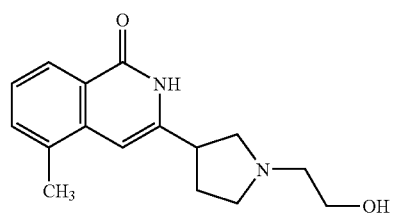
29a
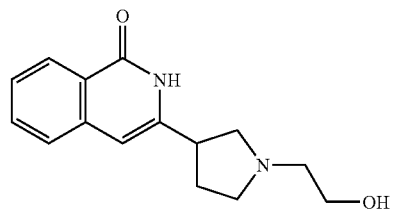

-continued

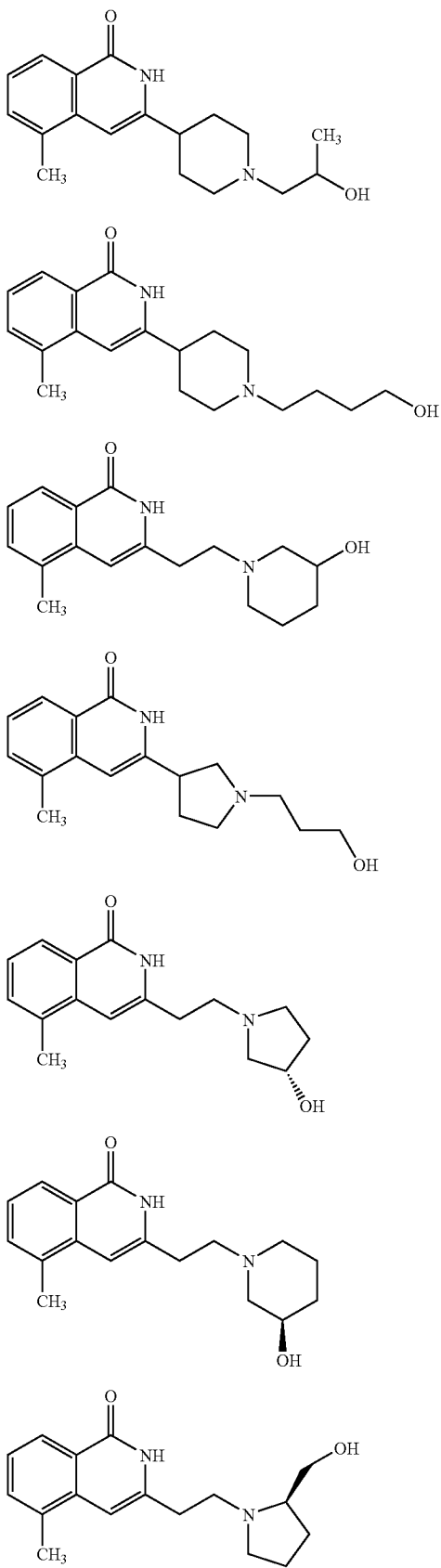

30a
31a
32a
33a
34a
35a
36a

-continued

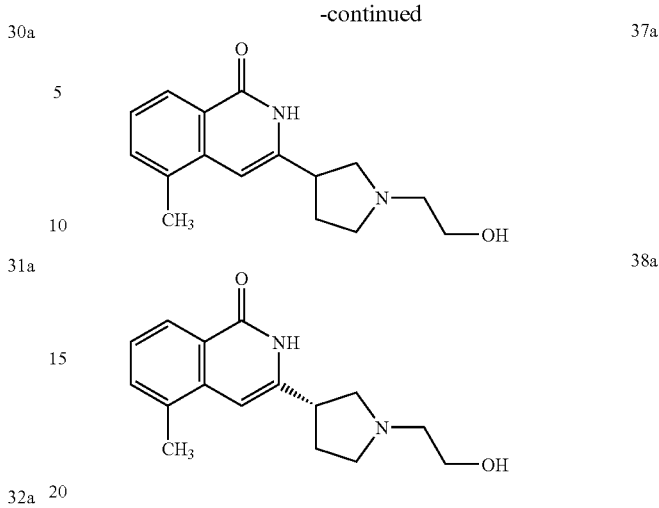

37a
38a

Example 1b (a) Ethyl 3,5-dimethylpyrrolidine-2-carboxylate hydrochloride (6.0 g) described in Tetrahedron Lett., vol. 32, No. 30, pp. 3727-3730 (1991) was dissolved in potassium carbonate (5.0 g), water (30 mL) and chloroform (50 mL), and di-tert-butyl dicarbonate (7.0 g) was added. The mixture was stirred at room temperature. After the completion of the reaction, the reaction mixture was partitioned. The organic layer was dried over magnesium sulfate and concentrated to quantitatively give ethyl 1-tert-butoxycarbonyl-3,5-dimethylpyrrolidine-2-carboxylate as an oil.

(b) The entire amount of 1-tert-butoxycarbonyl-3,5-dimethylpyrrolidine-2-carboxylate was dissolved in tetrahydrofuran (100 mL) and lithium aluminum hydride (0.93 g) was added at −78° C. The mixture was stirred with heating to room temperature and then cooled to −78° C. again. Lithium aluminum hydride (0.93 g) was added and the mixture was stirred with heating to room temperature. After the completion of the reaction, the mixture was cooled to −78° C., water (3.5 mL) was added and the mixture was heated to room temperature. Insoluble materials were filtered off and washed with ethyl acetate. The organic layers were combined and concentrated. The obtained residue was purified by silica gel column chromatography. The fraction eluted with hexane:ethyl acetate=2:1 was concentrated to quantitatively give 1-tert-butoxycarbonyl-3,5-dimethyl-2-hydroxymethylpyrrolidine as an oil.

(c) The entire amount of 1-tert-butoxycarbonyl-3,5-dimethyl-2-hydroxymethylpyrrolidine was dissolved in 4N hydrogen chloride-dioxane (30 mL) and the mixture was stirred at room temperature. After the completion of the reaction, the reaction-solvent was concentrated to quantitatively give 3,5-dimethyl-2-hydroxymethylpyrrolidine hydrochloride as an oil.

$^1$H-NMR (DMSO-d$_6$)δ: 1.03 (3H, d, J=7 Hz), 1.29 (3H, d, J=7 Hz), 1.65-1.84 (1H, m), 2.08-2.23 (1H, m), 2.98-3.10 (1H, m), 3.34-3.41 (1H, m), 3.45-3.70 (3H, m), 5.30-5.38 (1H, m), 8.55 (1H, brs), 9.72 (1H, brs).

(d) The entire amount of 3,5-dimethyl-2-hydroxymethylpyrrolidine hydrochloride was dissolved in aqueous potassium carbonate solution (50 mL) and chloroform (50 mL), and acrylonitrile (20 mL) was added. The mixture was heated under reflux for 2 hr. After the completion of the reaction, the organic layer was separated and dried over magnesium sulfate. The solvent was concentrated and the obtained residue was purified by silica gel column chromatography. The fraction eluted with chloroform:methanol=40:1 was concentrated to give 3-(3,5-dimethyl-2-hydroxymethylpyrrolidin-1-yl) propionitrile (2.3 g).

$^1$H-NMR (CDCl$_3$)δ: 1.00 (3H, d, J=7 Hz), 1.13 (3H, d, J=7 Hz), 1.59 (2H, t, J=7 Hz), 2.16 (1H, m), 2.36-2.42 (1H, m), 2.47-2.58 (3H, m), 2.90-3.02 (3H, m), 3.43-3:52 (1H, m), 3.57-3.62 (1H, m).

(e) Diisopropylamine (3.3 g) was dissolved in tetrahydrofuran (20 mL) and n-butyllithium (1.58M, hexane solution, 19 mL) was added dropwise under a nitrogen stream at −78° C. After the completion of the dropwise addition, a solution (20 mL) of N,N-diethyl-2,3-dimethylbenzamide (5.2 g) in tetrahydrofuran was added dropwise and the mixture was stirred for 1 hr. A solution (20 mL) of 3-(3,5-dimethyl-2-hydroxymethylpyrrolidin-1-yl)propionitrile (2.3 g) in tetrahydrofuran was added dropwise to the reaction mixture and the temperature of the reaction mixture was raised to room temperature. After the completion of the reaction, the reaction mixture was acidified by adding conc. hydrochloric acid. The reaction mixture was concentrated and washed with hexane. The aqueous layer was basified by adding potassium carbonate and extracted with chloroform. The organic layer was dried over magnesium sulfate. The solvent was concentrated and the obtained residue was purified by silica gel column chromatography. The fraction eluted with chloroform:methanol=30:1 was concentrated and the obtained residue was again purified by silica gel column chromatography (NH silica gel, Fuji Silysia Chemical). The fraction eluted with chloroform was concentrated and ether was added to the obtained residue. The precipitated crystals were collected by filtration to give 3-[2-(3,5-dimethyl-2-hydroxymethylpyrrolidin-1-yl)ethyl]-5-methyl-2H-isoquinolin-1-one (0.5 g).

$^1$H-NMR (CDCl$_3$)δ: 1.04 (3H, d, J=6 Hz), 1.21 (3H, d, J=6 Hz), 1.60-1.70 (2H, m), 2.30-2.48 (2H, m), 2.51 (3H, s), 2.62-2.70 (1H, m), 2.81-3.13 (4H, m), 3.58-3.65 (1H, m), 3.72-3.80 (1H, m), 4.25 (1H, brs), 6.39 (1H, s), 7.31 (1H, t, J=8 Hz), 7.46 (1H, d, J=7 Hz), 8.23 (1H, d, J=8 Hz), 12.48 (1H, brs), Example 2b In the same manner as in the method described in Tetrahedron Lett., Vol. 32, No. 30, pp. 3727-3730 (1991), ethyl 5-ethyl-3-methylpyrrolidine-2-carboxylate hydrochloride is obtained. In the same manner as in Example 1b (a) and using ethyl 5-ethyl-3-methylpyrrolidine-2-carboxylate hydrochloride, ethyl 1-tert-butoxycarbonyl-5-ethyl-3-methylpyrrolidine-2-carboxylate is obtained. In the same manner as in Example 1b (b) and using ethyl 1-tert-butoxycarbonyl-5-ethyl-3-methylpyrrolidine-2-carboxylate, 1-tert-butoxycarbonyl-5-ethyl-2-hydroxymethyl-3-methylpyrrolidine is obtained. In the same manner as in Example 1b (c) and using 1-tert-butoxycarbonyl-5-ethyl-2-hydroxyethyl-3-methylpyrrolidine, 5-ethyl-2-hydroxymethyl-3-methylpyrrolidine hydrochloride is obtained. In the same manner as in Example 1b (d) and using 5-ethyl-2-hydroxymethyl-3-methylpyrrolidine hydrochloride, 3-(5-ethyl-2-hydroxymethyl-3-methylpyrrolidin-1-yl)propionitrile is obtained. In the same manner as in Example 1b (e) and using 3-(5-ethyl-2-hydroxymethyl-3-methylpyrrolidin-1-yl)propionitrile and N,N-diethyl-2,3-dimethylbenzamide, 3-[2-(-5-ethyl-2-hydroxymethyl-3-methylpyrrolidin-1-yl)ethyl]-5-methyl-2H-isoquinolin-1-one is obtained.

Example 3b

In the same manner as in Example 1b (a) and using ethyl (2S,4R,5R)-4,5-dimethylpyrrolidine-2-carboxylate described in Tetrahedron Lett., Vol. 34, No. 3, pp. 537-540 (1993), ethyl (2S,4R,5R)-1-tert-butoxycarbonyl-4,5-dimethylpyrrolidine-2-carboxylate is obtained. In the same manner as in Example 1b (b) and using ethyl (2S,4R,5R)-1-tert-butoxycarbonyl-4,5-dimethylpyrrolidine-2-carboxylate, (2S,4R,5R)-1-tert-butoxycarbonyl-4,5-dimethyl-2-hydroxymethylpyrrolidine is obtained. In the same manner as in Example 1b (c) and using (2S,4R,5R)-1-tert-butoxycarbonyl-4,5-dimethyl-2-hydroxymethylpyrrolidine, (2S,4R,5R)-4,5-dimethyl-2-hydroxymethylpyrrolidine-hydrochloride is obtained. In the same manner as in Example 1b (d) and using (2S,4R,5R)-4,5-dimethyl-2-hydroxymethylpyrrolidine hydrochloride, 3-[(2S,4R,5R)-4,5-dimethyl-2-hydroxymethylpyrrolidin-1-yl]propionitrile is obtained. In the same manner as in Example 1b (e) and using 3-[(2S,4R,5R)-4,5-dimethyl-2-hydroxymethylpyrrolidin-1-yl]propionitrile and N,N-diethyl-2,3-dimethylbenzamide, 3-(2-[(2S,4R,5R)-4,5-dimethyl-2-hydroxymethylpyrrolidin-1-yl]ethyl)-5-methyl-2H-isoquinolin-1-one is obtained.

Example 4b

In the same manner as in the method described in Tetrahedron Lett., Vol. 34, No. 3, pp. 537-540 (1993), ethyl (2R,4S,5S)-4,5-dimethylpyrrolidine-2-carboxylate is obtained. In the same manner as in Example 3b and using ethyl (2R,4S,5S)-4,5-dimethylpyrrolidine-2-carboxylate, 3-(2-[(2R,4S,5s)-4,5-dimethyl-2-hydroxymethylpyrrolidin-1-yl]ethyl)-5-methyl-2H-isoquinolin-1-one is obtained.

Example 5b (2R,4S)-4-Methylpyrrolidine-2-carboxylic acid described in J. Chem. Soc. C, pp. 514-522 (1971) is reacted with di-tert-butyl dicarbonate to give (2R,4S)-1-tert-butoxycarbonyl-4-methylpyrrolidine-2-carboxylic acid. (2R,4S)-1-tert-Butoxycarbonyl-4-methylpyrrolidine-2-carboxylic acid is reacted with methyl iodide in the presence of potassium carbonate in acetonitrile solvent to give methyl (2R,4S)-1-tert-butoxycarbonyl-4-methylpyrrolidine-2-carboxylate. Methyl (2R,4S)-1-tert-butoxycarbonyl-4-methylpyrrolidine-2-carboxylate is reduced with lithium borohydride to give (2R,4S)-1-tert-butoxycarbonyl-2-hydroxymethyl-4-methylpyrrolidine. (2R,4S)-1-tert-Butoxycarbonyl-2-hydroxymethyl-4-methylpyrrolidine is reacted with 4N hydrogen chloride-dioxane to give (2R,4S)-2-hydroxymethyl-4-methylpyrrolidine hydrochloride. (2R,4S)-2-Hydroxymethyl-4-methylpyrrolidine hydrochloride is reacted with acrylonitrile to give 3-[(2R,4S)-2-hydroxymethyl-4-methylpyrrolidin-1-yl]propionitrile. In the same manner as in Example 1b (e) and using 3-[(2R,4S)-2-hydroxymethyl-4-methylpyrrolidin-1-yl]propionitrile and N,N-diethyl-2,3-dimethylbenzamide, 3-(2-(2R,4S)-2-hydroxymethyl-4-methylpyrrolidin-1-yl]ethyl)-5-methyl-2H-isoquinolin-1-one is obtained.

Example 6b

In the same manner as in Example 5b' and using (2S,4R)-4-methylpyrrolidine-2-carboxylic acid instead of (2R,4S)-4-methylpyrrolidine-2-carboxylic acid, 3-(2-[(2S,4R)-2-hydroxymethyl-4-methylpyrrolidin-1-yl]ethyl)-5-methyl-2H-isoquinolin-1-one is obtained.

Example 7b

In the same manner as in Example 5b and using (R)-2-methylpyrrolidine-2-carboxylic acid described in Tetrahedron Lett., Vol. 37, No. 46, pp. 8395-8398 (1996), (R)-3-[2-(2-hydroxymethyl-2-methylpyrrolidin-1-yl)ethyl]-5-methyl-2H-isoquinolin-1-one is obtained.

Example 8b

In the same manner as in Example 5b and using (2R,3S)-3-methylpyrrolidine-2-carboxylic acid described in J. Am. Chem. Soc., Vol. 88, pp. 3624-3625 (1966), 3-{2-[(2R,3S)-2-hydroxymethyl-3-methylpyrrolidin-1-yl]ethyl}-5-methyl-2H-isoquinolin-1-one is obtained.

Example 9b

In the same manner as in Example 5b and using 4,4-dimethylpyrrolidine-2-carboxylic acid described in J. Med. Chem., Vol. 20, pp. 1176-1179 (1977), 3-[2-(4,4-dimethyl-2-hydroxymethylpyrrolidin-1-yl)ethyl]-5-methyl-2H-isoquinolin-1-one is obtained.

Example 10b (a) (33,5R)-5-Hydroxymethylpyrrolidin-3-ol hydrochloride (0.4 g) described in Biochemistry, Vol. 5, pp. 1154-1155 (1966) was dissolved in aqueous potassium carbonate solution (2 mL) and acetonitrile (2 mL). Acrylonitrile (0.5 mL) was added and the mixture was stirred at room temperature for 5 hr. After the completion of the reaction, the reaction mixture was concentrated and the obtained residue was suspended in chloroform-methanol and dried by adding magnesium sulfate. Magnesium sulfate was filtered off and the solvent was concentrated to give 3-[(2R,4S)-4-hydroxy-2-hydroxymethylpyrrolidin-1-yl]propionitrile (0.47 g).

$^1$H-NMR (CDCl$_3$)δ: 1.60-1.75 (1H, m), 1.80-1.90 (1H, m), 2.05-2.12 (1H, m), 2.30-2.40 (1H, m), 2.44-2.54 (3H, m), 2.75-2.85 (1H, m), 3.04-3.16 (2H, m), 3.38-3.46 (2H, m), 3.65-3.72 (1H, m), 4.38-4.48 (1H, m).

(b) In the same manner as in Example 1b (e) and using 3-[(2R,4S)-4-hydroxy-2-hydroxymethylpyrrolidin-1-yl]propionitrile (0.47 g) ad N,N-diethyl-2,3-dimethylbenzamide (2.1 g), 3-{2-[(2R,4S)-4-hydroxy-2-hydroxymethylpyrrolidin-1-yl]ethyl}-5-methyl-2H-isoquinolin-1-one (0.14 g) was obtained.

$^1$H-NMR (CDCl$_3$)δ: 1.85-1.96 (1H, m), 2.18-2.30 (1H, m), 2.49 (3H, s), 2.65-2.75 (2H, m), 2.88-3.00 (1H, m), 3.08-3.25 (3H, m), 3.52-3.60 (2H, m), 3.78-3.86 (1H, m), 4.52-4.60 (1H, m), 6.41 (1H, 5); 7.31 (1H, t, J=8 Hz), 7.46 (1H, d, J=7 Hz), 8.20 (1H, d, J=8 Hz), 12.32 (1H, brs).

Example 11b (a) In the same manner as in Example 10b (a) and using (3R,5R)-5-hydroxyiethylpyrrolidin-3-ol hydrochloride (0.78 g) described in Collect. Czech. Chem. Commun., Vol. 61, pp. S234-S237 (1996), 3-[(2R,4R)-4-hydroxy-2-hydroxymethylpyrrolidin-1-yl)propionitrile was quantitatively obtained.

$^1$H-NMR (CDCl$_3$)δ: 1.75-1.86 (1H, m), 2.30-2.40 (1H, m), 2.47-2.57 (3H, m), 2.69-2.80 (1H, m), 2.82-2.92 (1H, m), 3.04-3.22 (2H, m), 3.45-3.51 (1H, m), 3.70-3.76 (1H, m), 4.22-4.27 (1H, m).

(b) In the same manner as in Example 1b (e) and using 3-[(2R,4R)-4-hydroxy-2-hydroxymethylpyrrolidin-1-yl]propionitrile (total amount) and N,N-diethyl-2,3-dimethylbenzamide (4.1 g), 3-(2-[(2R,4R)-4-hydroxy-2-hydroxymethylpyrrolidin-1-yl]ethyl)-5-methyl-2H-isoquinolin-1-one (0.47 g) was obtained.

$^1$H-NMR (CDCl$_3$)δ: 1.96-2.01 (1H; m), 2.32-2.43 (1H, m), 2.48-2.59 (2H, m), 2.51 (3H, s), 2.90-3.16 (4H, m), 3.46-3.58 (2H, m), 3.78-3.83 (1H, m), 4.25-4.32 (1H, m), 5.12-5.26 (1H, m), 6.43 (1H, s), 6.70 (1H, m), 7.33 (1H, t, J=8 Hz), 7.48 (1H, d, J=7 Hz), 8.21 (1H, d, J=8 Hz), 12.79 (1H, brs).

Example 12b

In the same manner as in Example 10b (a) and using (3R,5S)-5-hydroxymethylpyrrolidin-3-ol described in Collect. Czech. Chem. Commun., vol. 61, pp. S234-S237 (1996), 3-[(2S,4R)-4-hydroxy-2-hydroxymethylpyrrolidin-1-yl]propionitrile is obtained. In the same manner as in Example 1b (e) and using 3-(2S,4R)-4-hydroxy-2-hydroxymethylpyrrolidin-1-yl]propionitrile and N,N-diethyl-2,3-dimethylbenzamide, 3-(2-[(2S,4R)-4-hydroxy-2-hydroxymethylpyrrolidin-1-yl]ethyl)-5-methyl-2H-isoquinolin-1-one is obtained.

Example 13b

In the same manner as in Example 10b (a) and using (3S, 5S)-5-hydroxymethylpyrrolidin-3-ol described in Collect. Czech. Chem. Commun., vol. 61, pp, S234-S237 (1996), 3-[(2S,4S)-4-hydroxy-2-hydroxymethylpyrrolidin-1-yl]propionitrile is obtained. In the sample manner as in Example 1b (e) and using 3-[(2S,4S)-4-hydroxy-2-hydroxymethylpyrrolidin-1-yl]propionitrile and N,N-diethyl-2,3-dimethylbenzamide, 3-(2-[(2S,4S)-4-hydroxy-2-hydroxymethylpyrrolidin-1-yl]ethyl)-5-methyl-2H-isoquinolin-1-one is obtained.

Example 14b

In the same manner as in Example 10b (a) and using cis-2-hydroxymethyl-3-methylpiperidine described in J. Heterocycl. Chem., sol. 9, pp. 875-878 (1972), 3-(cis-2-hydroxymethyl-3-methylpiperidin-1-yl)propionitrile is obtained. In the same manner as in Example 1b (e) and using 3-(Cis-2-hydroxymethyl-3-methylpiperidin-1-yl)propionitrile and N,N-diethyl-2,3-dimethylbenzamide, 3-[2-(cis-2-hydroxymethyl-3-methylpiperidin-1-yl)ethyl]-5-methyl-2H-isoquinolin-1-one is obtained.

Example 15b (3R,5R)-5-Hydroxymethylpyrrolidin-3-ol and 4-bromobutyronitrile are reacted in the presence of potassium carbonate in N,N-dimethylformamide to give 4-[(2R,4R)-4-hydroxy-2-hydroxymethylpyrrolidin-1-yl]butyronitrile. In the same manner as in Example 1b (e) and using 4-[(2R,4R)-4-hydroxy-2-hydroxymethylpyrrolidin-1-yl]butyronitrile and N,N-diethyl-2,3-dimethylbenzamide, 3-{3-[(2R,4R)-4-hydroxy-2-hydroxyiethylpyrrolidin-1-yl]propyl}-5-methyl-2H-isoquinolin-1-one is obtained.

Example 16b (a) Under a nitrogen stream, tetrahydrofuran (13 mL) was added to diisopropylamine (5.48 mL) and the internal temperature was lowered to −78° C. A solution (1.58 mol/L, 23.8 mL) of n-butyllithium in n-hexane was added dropwise and the mixture was stirred at an outer temperature of 0° C. for 30 min. The lithium diisopropylamide solution was cooled to −78° C. again and a solution of N,N-diethyl-3-fluoro-2-methylbenzamide (3.41 g) in tetrahydrofuran (15 mL) was slowly added dropwise. After the completion of the dropwise addition, the mixture was stirred at −78° C. for 1 hr and a solution of (R)-3-(2-hydroxymethylpyrrolidin-1-yl)-N-methoxy-N-methylpropanamide (3.53 g) in tetrahydrofuran (15 mL) was slowly added dropwise. The mixture was allowed to warm to room temperature and stirred overnight (ca. 18 hr). After the completion of the reaction, water was added to quench the reaction. Tetrahydrofuran was removed under reduced pressure and the resulting aqueous layer was extracted with chloroform. The organic layer was washed with saturated brine, dried over anhydrous magnesium sulfate and filtered. Chloroform was evaporated under reduced pressure to give (R)-N,N-diethyl-3-fluoro-2-[4-(2-hydroxymethylpyrrolidin-1-yl)-2-oxobutyl]benzamide (5.94 g), which was subjected to the next reaction without further purification.

(b) Concentrated hydrochloric acid (35 mL) was added to (R)-N,N-diethyl-3-fluoro-2-[4-(2-hydroxymethylpyrrolidin-1-yl)-2-oxobutyl]benzamide (5.94 g) and the mixture was heated under reflux with stirring for 5 hr. After the completion of the reaction, the reaction mixture was alkalified by adding powdery potassium carbonate and extracted with chloroform. The extract was washed with saturated brine, dried over anhydrous magnesium sulfate and filtered. Chloroform was evaporated under reduced pressure to give (R)-5-fluoro-3-[2-(2-hydroxymethylpyrrolidin-1-yl)ethyl]isocoumarin (4.01 g), which was subjected to the next reaction without further purification.

(c) (R)-5-Fluoro-3-[2-(2-hydroxymethylpyrrolidin-1-yl)ethyl]isocoumarin (4.01 g) was dissolved in acetic acid (12 mL) and the mixture was heated to 70° C. Ammonium carbonate (4.90 g) was added and the mixture was heated under reflux for 1 hr. The reaction mixture was allowed to warm to room temperature and added to a solution of sodium hydroxide (8 g) in water (30 mL). The mixture was stirred at room temperature for 30 min and the reaction mixture was diluted with water, extracted with chloroform, washed with saturated brine, dried over anhydrous magnesium sulfate and filtered. Chloroform was evaporated under reduced pressure and the obtained oil was applied to silica gel column chromatography (chloroform chloroform methanol 20:1→10:1). The obtained crude crystals were washed with ethyl acetate and collected by filtration to give (R)-5-fluoro-3-[2-(2-hydroxymethylpyrrolidin-1-yl)ethyl]-2H-isoquinolin-1-one (595 mg).

$^1$H-NMR (CDCl$_3$)δ: 1.70-2.00 (4H, m), 2.35-2.45 (1H, m), 2.55-2.75 (2H, m), 2.80-3.00 (2H, m), 3.10-3.25 (1H, m), 3.30-3.40 (1H, m), 3.50-3.60 (1H, m), 3.70-3.80 (1H, m), 3.85 (1H, brs), 6.49 (1H, s), 7.26-7.38 (2H, m), 8.23 (1H, d, J=7.2 Hz), 12.6 (1H, brs). MS (ESI): 291 (m+1)

Example 17b

In the same manner as in Example 16b and using N,N-diethyl-3-chloro-2-methylbenzamide (3.35 g) and (R)-3-(2-hydroxymethylpyrrolidin-1-yl)-N-methoxy-N-methylpropanamide (3.22 g), (R)-5-chloro-3-[2-(2-hydroxymethylpyrrolidin-1-yl)ethyl]-2H-isoquinolin-1-one (645 mg) was obtained.

$^1$H-NMR (CDCl$_3$)δ: 1.70-2.00 (4H, m), 2.35-2.45 (1H, m), 2.55-2.75 (2H, m), 2.80-3.00 (2H, m), 3.10-3.25 (1H, m), 3.30-3.40 (1H, m), 3.50-3.60 (1H, m), 3.70-3.80 (1H, m), 6.65 (1H, s), 7.30-7.35 (1H, m), 7.67 (1H, d, J=8.1 Hz), 8.28 (1H, d, J=8.1 Hz), 12.7 (1H, brs). MS (ESI): 307 (M+1).

Example 18b

In the same manner as in Example 16b and using N,N-diethyl-3-fluoro-2-methylbenzamide (3.46 g) and (R)-3-(3-hydroxypyrrolidin-1-yl)-N-methoxy-N-methylpropanamide (3.36 g), (R)-5-fluoro-3-[2-(3-hydroxypyrrolidin-1-yl)ethyl]-2H-isoquinolin-1-one (1.19 g) was obtained.

$^1$H-NMR (DMSO-d$_6$)δ: 1.45-1.60 (1H, m), 1.85-2.00 (1H, m), 2.35-2.40 (1H, m), 2.40-2.55 (1H, m), 2.60-2.80 (6H, m), 4.16-4.20 (1H, m), 4.70 (1H, d, J=4.2 Hz), 6.45 (1H, s), 7.37-7.44 (1H, m), 7.49-7.55 (1H, m), 7.96 (1H, d, J=7.8 Hz), 11.5 (1H, brs). MS (ESI): 277 (M+1).

Example 19b

In the same manner as in Example 16b and using N,N-diethyl-3-chloro-2-methylbenzamide (3.43 g) and (R)-3-(3-hydroxypyrrolidin-1-yl)-N-methoxy-N-methylpropanamide (3.08 g), (R)-5-chloro-3-[2-(3-hydroxypyrrolidin-1-yl)ethyl]-2H-isoquinolin-1-one (102 mg) was obtained.

$^1$H-NMR (DMSO-d$_6$)δ: 1.45-1.60 (1H, m), 1.85-2.00 (1H, m), 2.35-2.40 (1H, m); 2.40-2.55 (1H, m), 2.60-2.80 (6H, m), 4.19 (1H, brs), 4.74 (1H, brs), 6.56 (1H, s), 7.38-7.43 (1H, m), 7.81 (1H, d, J=7.5 Hz), 8.12 (1H, d, J=7.5 Hz), 11.6 (1H, brs). MS (ESI): 293 (Ms+1)

Example 20b (a) (R)-2-Methoxymethylpyrrolidine (5 g) and N-methoxy-N-methylacrylamide (5.5 g) were dissolved in tetrahydrofuran (50 mL) and the mixture was stirred at room temperature. After the completion of the reaction, the solvent was concentrated to quantitatively give (R)-3-(2-methoxymethylpyrrolidin-1-yl)-N-methoxy-N-methylpropanamide.

$^1$H-NMR (CDCl$_3$)δ: 1.60-1.91 (4H, m), 2.24 (1H, q, J=8 Hz), 2.55-2.72 (4H, m), 3.10-3.43 (4H, m), 3.18 (3H, s), 3.35 (3H, s), 3.69 (3H, s).

(b) Diisopropylamine (3.03 g) was dissolved in tetrahydrofuran (30 mL) and a solution (1.58 mol/L, 17.7 mL) of n-butyllithium in n-hexane was added dropwise under a nitrogen stream at −78° C. Subsequently, a solution of N,N-diethyl-2,3-dimethylbenzamide (3.28 g) in tetrahydrofuran was added dropwise. After the completion of the dropwise addition, the mixture was stirred at −78° C. for 1 hr. A solution of (R)-3-(2-methoxymethylpyrrolidin-1-yl)-N-methoxy-N-methylpropanamide (3.22 g) in tetrahydrofuran was added dropwise and the mixture was stirred at −78° C. for 30 min. After the completion of the reaction, concentrated hydrochloric acid (15 mL) and water (30 mL) were added and the mixture was heated under reflux. Tetrahydrofuran and hexane were evaporated and the mixture was further heated under reflux for 6 hr. After the completion of the reaction, the reaction mixture was cooled to room temperature and basified by adding potassium carbonate. The mixture was extracted with Chloroform and dried over magnesium sulfate. The solvent was concentrated and the obtained residue was purified by silica gel column chromatography. The fraction eluted with chloroform:methanol=50:1 was concentrated to give (R)-5-methyl-3-[2-(2-methoxymethylpyrrolidin 1-yl)ethyl]isocoumarin (3.2 g).

$^1$H-NMR (CDCl$_3$)δ: 1.59-1.86 (4H, m), 2.30 (1H, q, J=8 Hz), 2.46 (3H, s), 2.63-2.81 (4H, m), 3.14-3.33 (3H, m), 3.36 (1H, s), 3.39-3.44 (1H, m), 6.45 (1H, s), 7.34 (1H, t, J=8 Hz), 7.51 (1H, d, J=7 Hz), 8.12 (1H, d, J=8 Hz).

(c) (R)-5-Methyl-3-[2-(2-methoxymethylpyrrolidin-1-yl) ethyl]isocoumarin (3.2 g) was dissolved in acetic acid (10 mL). Ammonium carbonate (7 g) was added and the mixture was heated under reflux for 1 hr. The reaction mixture was cooled to room temperature and the mixture was basified by adding aqueous sodium hydroxide solution. The mixture was extracted with chloroform and dried over magnesium sulfate. The solvent was concentrated and the obtained residue was purified by silica gel column chromatography. The fraction eluted with chloroform:methanol=50:1 was concentrated and the obtained residue was dissolved in acetone. 4N Hydrogen chloride/dioxane was added and the precipitated crystals were collected by filtration to give (R)-5-methyl-3-[2-(2-methoxymethylpyrrolidin-1-yl)ethyl]-2H-isoquinolin-1-one hydrochloride (1.5 g).

$^1$H-NMR (DMSO-$d_6$) δ: 1.67-1.78 (1H, m), 1.87-2.23 (3H, m), 2.49 (3H, s), 2.90-3.10 (2H, m), 3.15-3.28 (1H, m), 3.31-3.42 (1H, m), 3.34 (3H, s), 3.52-3.80 (5H, m), 6.54 (1H, s), 7.34 (1H, t, J=8 Hz), 7.53 (1H, d, J=7 Hz), 8.02 (1H, d, J=8 Hz), 10.49 (1H, brs), 11.46 (1H, brs).

Example 21b

In the same manner as in Example 20b and using (R)-3-(2-methoxymethylpyrrolidin-1-yl)-N-methoxy-m-methylpropanamide (3.2 g) and N,N-diethyl-3-chloro-2-methylbenzamide (3.2 g), (R)-5-chloro-3-[2-(2-methoxymethylpyrrolidin-1-yl)ethyl]-2H-isoquinolin-1-one hydrochloride (1.1 g) was obtained.

$^1$NMR (DMSO-$d_6$) δ: 1.65-2.22 (4H, m), 2.95-3.45 (4H, m), 3.34 (3H, s), 3.54-3.76 (5H, m), 6.64 (1H, s), 7.45 (1H, t, J=8 Hz), 7.85 (1H, d, J=8 Hz), 8.14 (1H, d, J=8 Hz), 10.49 (1H, brs), 11.74 (1H, brs).

Example 22b

In the same manner as in Example 20b and using (R)-3-(2-methoxymethylpyrrolidin-1-yl)-N-methoxy-N-methylpropanamide (3.2 g) and N,N-diethyl-3-fluoro-2-methylbenzamide (2.9 g), (R)-5-fluoro-3-[2-(2-methoxymethylpyrrolidin-1-yl)ethyl]-2H-isoquinolin-1-one hydrochloride (0.58 g) was obtained.

$^1$H-NMR (DMSO-$d_6$) δ: 1.65-2.20 (4H, m), 2.95-3.75 (9H, m), 3.34 (3H, s), 6.55 (1H, s), 7.43-7.60 (2H, m), 7.99 (1H, d, J=8 Hz), 10.45 (1H, brs), 11.66 (1H, brs).

Example 23b (a) Sodium hydride (60% purity, 4.6 g) was suspended in tetrahydrofuran (50 mL) and a solution (50 mL) of (R)-1-tert-butoxycarbonyl-2-hydroxymethylpyrrolidine (20 g) in tetrahydrofuran was added dropwise under ice-cooling. After the completion of the dropwise addition, the mixture was stirred with heating at 50° C. for 30-min and ice-cooled, Ethyl iodide (18.7 g) was added to the reaction mixture and the 30' mixture was stirred overnight at room temperature. After the completion of the reaction, the solvent was concentrated and water was added to the obtained residue. The mixture was extracted with chloroform and dried over magnesium sulfate. The solvent was concentrated and the obtained residue was purified by silica gel column chromatography. The fraction eluted with hexane: ethyl acetate=3:1 was concentrated to give (R)-1-tert-butoxycarbonyl-2-ethoxymethylpyrrolidine (8.1 g).

$^1$NMR (CDCl$_3$) δ: 1.18 (3H, t, J=7 Hz), 1.46 (9H, s), 1.76-1.94 (4H, m), 3.20-3.39 (3H, m), 3.45-3.62 (3H, m), 3.80-4.00 (1H, m).

(b) (R)-1-tert-Butoxycarbonyl-2-ethoxymethylpyrrolidine (8.1 g) was dissolved in 4N hydrogen chloride-dioxane (30 mL). After the completion of the reaction, the solvent was concentrated to quantitatively give (R)-2-ethoxymethylpyrrolidine hydrochloride.

$^1$H-NMR (DMSO-$d_6$) δ: 1.14 (3H, t, J=7 Hz), 1.46-1.62 (1H, m), 1.75-2.05 (3H, m), 3.04-3.18 (2H, m), 3.40-3.68 (5H, m), 8.92 (1H, brs), 9.63 (1H, brs).

(c) The entire amount of (R)-2-ethoxymethylpyrrolidine hydrochloride was dissolved in an aqueous solution (20 mL) of potassium carbonate (4.8 g) and chloroform (20 mL) was added. The mixture was stirred at room temperature. N-Methoxy-N-methylacrylamide (4.8 g) was added to the reaction mixture and the mixture was stirred overnight at room temperature. After the completion of the reaction, the reaction mixture was extracted twice with chloroform, and dried over magnesium sulfate. The solvent was concentrated to quantitatively give (R)-3-(2-ethoxymethylpyrrolidin-1-yl)-N-methoxy-N-methylpropanamide as an oil.

(d) In the same manner as in Example 20b (b) and (c) and using (R)-3-(2-ethoxymethylpyrrolidin-1-yl)-N-methoxy-N-methylpropanamide (2.44 g) and N,N-diethyl-2,3-dimethylbenzamide (2.46 g) (R)-3-[2-(2-ethoxymethylpyrrolidin-1-yl) ethyl]-5-methyl-2H-isoquinolin-1-one hydrochloride (0.78 g was obtained.

$^1$H-NMR (DMSO-$d_6$) δ: 1.15 (3H, t, J=7 Hz), 1.60-1.75 (1H, m), 1.84-2.20 (3H, m), 2.48 (3H, s), 2.90-3.08 (2H, m), 3.15-3.30 (1H, m), 3.32-3.80 (8H, m), 6.52 (1H, s), 7.34 (1H, t, J=8 Hz), 7:53 (1H, d, J=7 Hz), 8.02 (1H, d, J=8 Hz), 10.28 (1H, brs), 11.45 (1H, brs).

Example 24b

In the same manner as: in Example 20b (b) and (c) and using (R)-3-(2-ethoxymethylpyrrolidin-1-yl)-N-methoxy-N-methylpropanamide (1.22 g) and N,N-diethyl-3-chloro-2-methylbenzamide (1.13 g), (R)-5-chloro-3-[2-(2-ethoxymethylpyrrolidin-1-yl)ethyl]-2H-isoquinolin-1-one hydrochloride (0.52 g) was obtained.

$^1$H-NMR (DMSO-$d_6$) δ: 1.15 (3H, t, J=7 Hz), 1.62-1.75 (1H, m), 1.87-2.20 (3H, m), 2.98-3.26 (3H, m), 3.30-3.80 (8H, m), 6.63 (1H, s), 7.46 (1H, t, J=8 Hz) 7.85 (1H, d, J=8 Hz), 8.14 (1H, d, J=8 Hz), 10.51 (1H, brs), 11.73 (1H, brs).

Example 25b

In the same manner as in Example 20b (b) and (c) and using (R)-3-(2-ethoxymethylpyrrolidin-1-yl)-N-methoxy-N-methylpropanamide (1.22 g) and N,N-diethyl-3-fluoro-2-methylbenzamide (1.05 g), (R)-3-[2-(2-ethoxymethylpyrrolidin-1-yl)ethyl]-5-fluoro-2H-isoquinolin-1-one hydrochloride (0.38 g) was obtained.

$^1$H-NMR (DMSO-$d_6$) δ: 1.15 (3H, t, J=7 Hz), 1.60-1.75 (1H, m), 1.87-2.21 (3H, m), 3.00-3.13 (3H, m), 3.15-3.30 (1H, m), 3.32-3.80 (8H, m), 6.55 (1H, s), 7.42-7.50 (1H, m), 7.54-7.60 (1H, m), 7.99 (1H, d, J=8 Hz), 10.26 (1H, brs), 11.65 (1H, brs).

The structural formula of the compound in each Example is shown in the following. The following numbers correspond to the above-mentioned Example numbers.

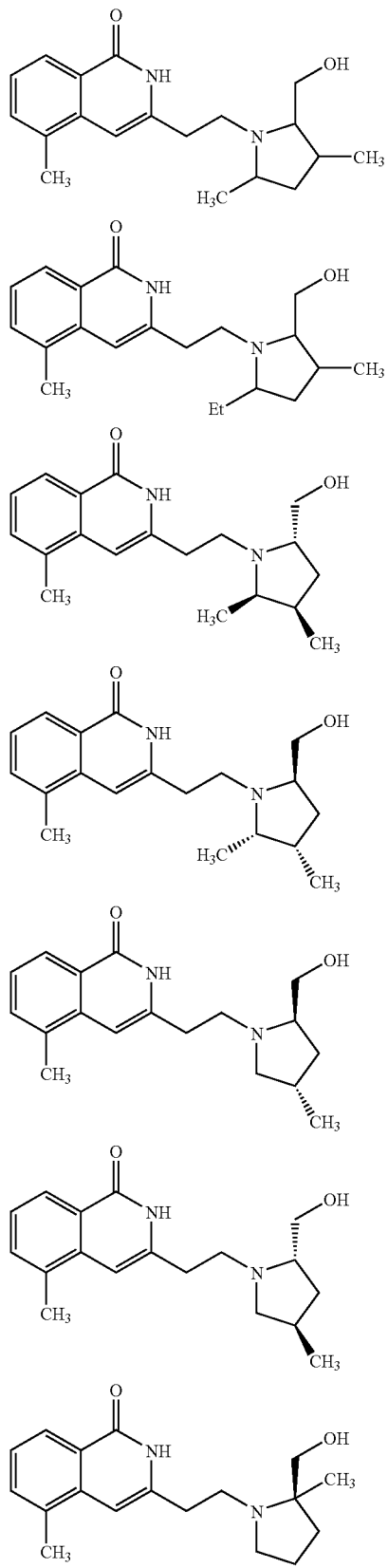
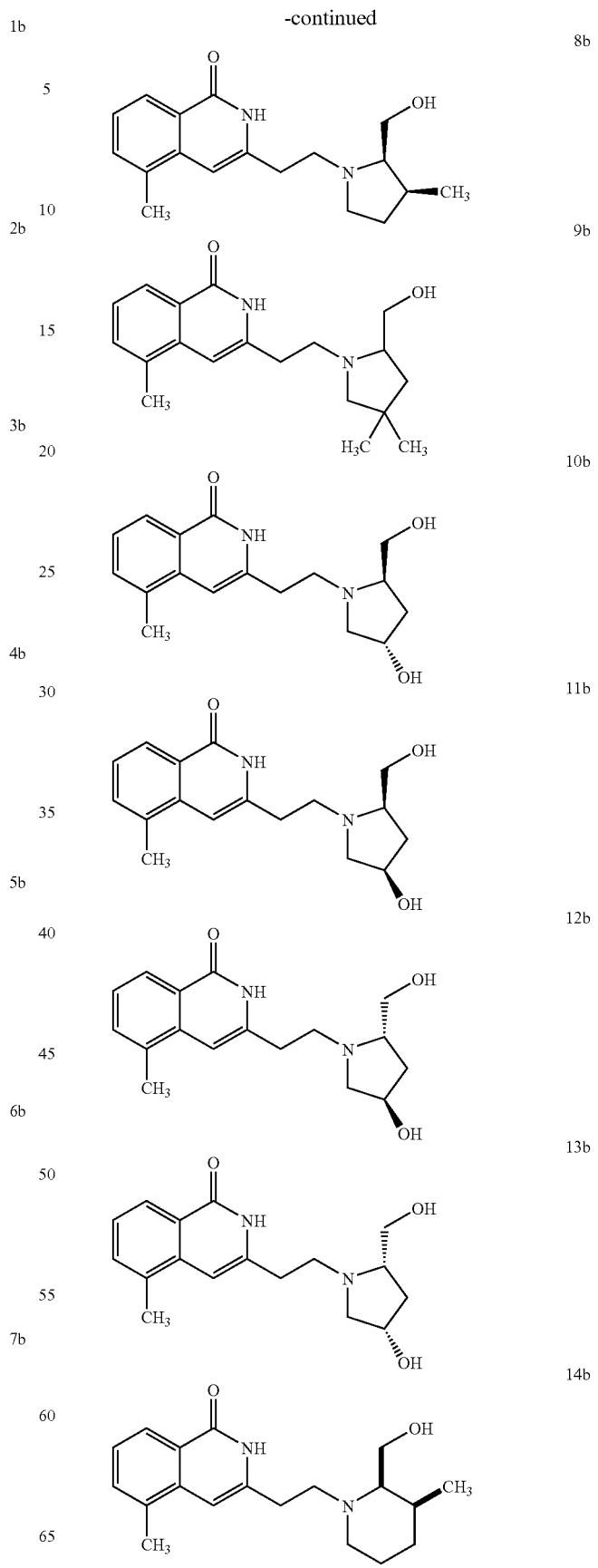

-continued

15b
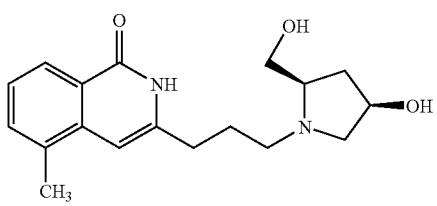

16b
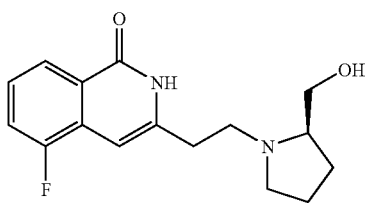

17b
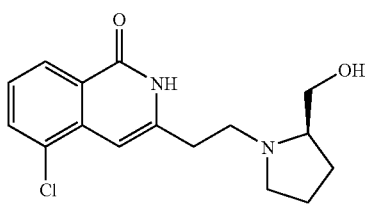

18b
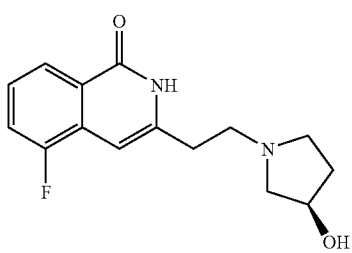

19b
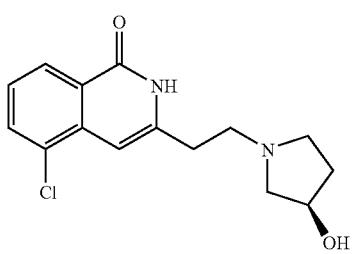

20b
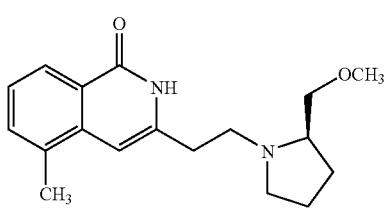

21b
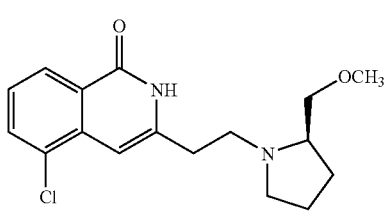

-continued

22b
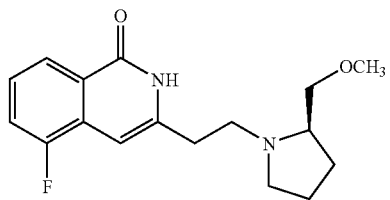

23b
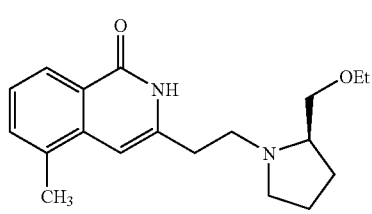

24b
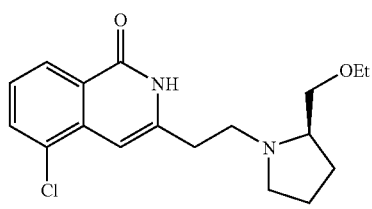

25b
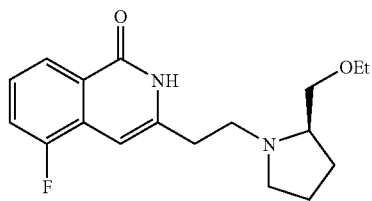

EXPERIMENTAL EXAMPLE

PARP Enzyme Activity Inhibitory Action

As an enzyme source, recombinant human PARP (4667-02X, Trevigen) was used. A poly ADP-ribosilation reaction was started by adding $^3$H-NAD (1.85 kBq, NAD [adenine-2, 8–$^3$H], Daiichi Chemicals Co., Ltd.) and activated DNA (0.02 mg/mL, 4667-03X, Trevigen) and then the enzyme source to an enzyme reaction buffer (10 mM Tris/HCl (pH 8.0), 1 mM MgCl$_2$, 28 mM KCl, 28 mM NaCl). After incubation at 25° C. for 15 min., the reaction was stopped with 20% trichloroacetic acid, and the resulting acid insoluble fraction was adsorbed to a GF/B filter. The filter was washed several times with 5% trichloroacetic acid, and the radiation dose on the filter was measured with a liquid scintillation counter.

The results are shown in Table 1. The PARP activity was determined by subtracting the radiation dose of an enzyme source non-addition sample as a blank value, and a 50% enzyme inhibitory value (IC$_{50}$ value) of each test compound was calculated with the radiation dose of a compound non-addition sample as 100%.

TABLE 1

| Test compound | PARP inhibitory activity IC$_{50}$ (nM) |
| --- | --- |
| Ex. 1a | 39 |
| Ex. 2a | 17 |
| Ex. 4a | 46 |
| Ex. 5a | 50 |
| Ex. 9a | 44 |
| Ex. 28a | 35 |

TABLE 1-continued

| Test compound | PARP inhibitory activity IC$_{50}$ (nM) |
|---|---|
| Ex. 34a | 34 |
| Ex. 36a | 29 |
| Ex. 37a | 20 |
| Ex. 38a | 29 |
| Control drug (DPQ) | 1000 |

DPQ=3,4-dihydro-5-[4-(1-piperidinyl)-butoxy]-1 (2H)-isoquinolinone (can be synthesized according to Example 32 of JP-A-H2-124874, PARP inhibitor described in each of WO99/08680 and WO99/11649)

From these results, it has become clear that the compounds shown in Examples of the present invention have superior PARP inhibitory activity as compared to DPQ.

Experimental Example 2

Determination of Stability

Each compound was dissolved in physiological saline to give solutions having a concentration of 1.0 mg/mL or 10 mg/mL. They were preserved at room temperature, under shielding or non-shielding and the residual ratio at day 7 and day 11 was measured by HPLC. The results are shown in Table 2.
column: Inertsil ODS3V (GL Science Inc.)
Mobile phase: methanol: 0.01 mol/L aqueous ammonium acetate solution
detection wavelength: 254 nm
flow rate: 1.0 mL/min

| Test compound | Concentration (mg/mL) | Residual rate (%) under shielding | | Residual rate (%) under non-shielding | |
|---|---|---|---|---|---|
| | | 7 days later | 11 days later | 7 days later | 11 days later |
| Ex. 1a | 1.0 | ≈100 | ≈100 | ≈100 | ≈100 |
| | 10 | ≈100 | ≈100 | ≈100 | ≈100 |
| Ex. 2a | 1.0 | ≈100 | ≈100 | ≈100 | ≈100 |
| | 10 | ≈100 | ≈100 | ≈100 | ≈100 |
| Ex. 36a | 1.0 | ≈100 | ≈100 | ≈100 | ≈100 |
| | 10 | ≈100 | ≈100 | ≈100 | ≈100 |

From these results, it has become clear that the compounds of the present invention are stable in aqueous solutions.

Experimental Example 3

Improving Effect on Neurological Symptoms Associated with Cerebral Infarction

Crab-eating macaque fasted in advance for 12 hr or more was anesthetized with intramuscular administration of ketamine hydrochloride (10 mg/kg) by injection and fixed on an operation table. Atropine sulfate (0.5 mg/body) was intramuscularly administered under pentobarbital anesthesia, and a small hole of about 5 mm was made with a dental drill near oval foramen and orbital fissure, and then dura matter and arachnoid were incised. Then, middle cerebral artery (MCA) near bifurcation of internal carotid artery was exposed. The MCA near bifurcation of internal carotid artery was coagulated/occluded with a bipolar coagulator to form cerebral infarction. Thereafter a solvent or an Example drug was administered in a sustained manner at 3 mg/kg/hr for 6 hr.

The neurological symptoms associated with cerebral infarction were observed 26 hours after MCA occlusion, The neurological symptoms were evaluated according to 5-point scoring tables, as shown in the following, with regard to conscious level, paralysis of limbs and attitude/behavior.

1. Conscious Level score 5: barely responsive to surrounding noise and presence of person
Score 4: responsive to surrounding noise and presence of person, but soon return to the original state
Score 3: responsive for a while to surrounding noise and presence of person
Score 2: always responsive to surrounding noise and presence of person
Score 1: always responsive to surrounding noise and presence of person and expressive
Score 0: normally respond to surrounding noise and presence of person 2. Paralysis of Limbs Score 5: never use hand and leg on paralyzed side
Score 4: sometimes use hand and leg on paralyzed side but with no strength
Score 3: use hand and leg on paralyzed side but cannot hold a feed
Score 2: often use hand and leg on paralyzed side but cannot hold a feed
Score 1: use hand and leg on paralyzed side comparatively freely and can hold and bring a feed to mouth
Score 0: normally use hand and leg on paralyzed side 3. Attitude and Behavior Score 5: sitting position.
Score 4: sometimes walk around from the sitting position.
Score 3: sometimes climb the cage,
Score 2: walk around often.
Score 1: climb the cage often.
Score 0: act normally.

TABLE 3

| Group name | n | Score |
|---|---|---|
| Solvent administration group | 4 | 14.8 ± 0.3 |
| Example drug administration group | 5 | 8.6 ± 1.9 (P < 0.05) |

From these results, it has become clear that the compounds of the present invention have an improving action on neurological symptoms associated with cerebral infarction.

INDUSTRIAL APPLICABILITY

The compound of the above-mentioned formula (I) and (I'), an optical isomer thereof, a pharmaceutically acceptable salt thereof, a hydrate thereof and a water adduct thereof are stable in aqueous solutions, have a potent PARP inhibitory action as compared to known compounds, and are useful as a therapeutic drug of cerebral infarction, particularly acute cerebral infarction. In addition, (R)-3-(3-hydroxypyrrolidin-1-yl)-N-methyl-N-methoxypropanamide, (R)-N,N-diethyl-2-[4-(3-hydroxypyrrolidin-1-yl)-2-oxobutyl]-3-methylbenzamide, (R)-3-[2-(3-hydroxypyrrolidin-1-yl)ethyl]-5-methylisocoumarin, (R)-3-(2-hydroxymethylpyrrolidin-1-yl)-N-methyl- N-methoxypropanamide, (R)-N,N-diethyl-2-[4-(2-hydroxymethylpyrrolidin-1-yl)-2-oxobutyl]-3-methylbenzamide, (R)-3-[2-(2-hydroxymethylpyrrolidin-1-yl)ethyl]-5-methylisocoumarin and (R)-3-[2-(2-hydroxymethylpyrrolidin-1-yl)ethyl]-5-methylisocoumarin hydrochloride are novel compounds and useful as intermediates for the synthesis of the compound of the formula (I).

This application is based on patent application Nos. 288833/2002, 340175/2002 and 109160/2003 filed in Japan, the contents of which are hereby incorporated by reference.

The invention claimed is:

1. An isoquinoline compound represented by the following formula (I):

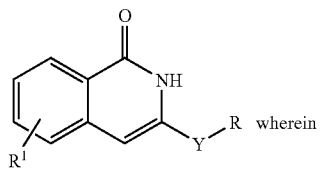

$R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;

Y is absent or an alkylene chain having 1 to 8 carbon atoms wherein an optional carbon atom may have a hydroxyl group; and R is represented by the following formula (II):

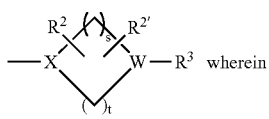

X is CH or a nitrogen atom, provided that when Y is absent in the formula (I), then X should be CH;

W is CH or a nitrogen atom, provided that when X is CH, then W should be a nitrogen atom;

s is an integer of 1 to 5;

t is an integer of 1 to 5;

when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, $R^2$ is a hydrogen atom, alkyl, a hydroxyl group or hydroxyalkyl and $R^{2'}$ is a hydroxyl group, hydroxyalkyl or alkoxyalkyl; and when $R^3$ is hydroxyalkyl, $R^2$ and $R^{2'}$ are the same or different and each is a hydrogen atom, a hydroxyl group, alkyl, hydroxyalkyl, alkoxycarbonyl, dialkylaminoalkyl or dialkylcarbamoyl, or $R^2$ and $R^{2'}$ are taken together to form ketone, an optically active form thereof, a pharmaceutically acceptable salt thereof, a water adduct thereof, a hydrate thereof and a solvate thereof.

2. The isoquinoline compound of claim 1, which is represented by the formula (I), wherein $R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;

Y is absent or an alkylene chain having 1 to 8 carbon atoms wherein an optional carbon atom may have a hydroxyl group; and R is represented by the formula (II), wherein, in the formula (II), X is CH or a nitrogen atom, provided that when Y is absent in the formula (I), then X should be CH;

W is CH or a nitrogen atom, provided that when X is CH, then W should be a nitrogen atom;

s is an integer of 1 to 5;

t is an integer of 1 to 5;

when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, $R^2$ and $R^{2'}$ are the same or different and each is a hydroxyl group or hydroxyalkyl; and when $R^3$ is hydroxyalkyl, $R^2$ and $R^{2'}$ are the same or different and each is a hydrogen atom, a hydroxyl group, alkyl, hydroxyalkyl, alkoxycarbonyl, dialkylaminoalkyl or dialkylcarbamoyl, or $R^2$ and $R^{2'}$ are taken together to form ketone, an optically active form thereof, a pharmaceutically acceptable salt thereof, a water adduct thereof, a hydrate thereof and a solvate thereof.

3. The isoquinoline compound of claim 1, which is represented by the formula (I), wherein $R^1$ is a hydrogen atom or alkyl;

Y is absent or an alkylene chain having 1 to 5 carbon atoms wherein an optional carbon atom may have a hydroxyl group; and R is represented by the formula (II), wherein, in the formula (II), X is CH or a nitrogen atom, provided that when Y is absent in the formula (I), then X should be CH;

W is CH or a nitrogen atom, provided that when X is CH, then W should be a nitrogen atom;

s is an integer of 1 to 5;

t is an integer of 1 to 5;

when $R^3$ is a hydrogen atom or alkyl, $R^2$ is a hydrogen atom, alkyl, a hydroxyl group or hydroxyalkyl and $R^{2'}$ is a hydroxyl group, hydroxyalkyl or alkoxyalkyl; and when $R^3$ is hydroxyalkyl, $R^2$ and $R^{2'}$ are the same or different and each is a hydrogen atom, a hydroxyl group, alkyl or hydroxyalkyl, an optically active form thereof a pharmaceutically acceptable salt thereof, a water adduct thereof, a hydrate thereof or a solvate thereof.

4. The isoquinoline compound of claim 1, which is represented by the formula (I), wherein $R^1$ is a hydrogen atom or alkyl;

Y is absent or an alkylene chain having 1 to 5 carbon atoms wherein an optional carbon atom may have a hydroxyl group; and R is represented by the formula (II), wherein, in the formula (II), X is CH or a nitrogen atom, provided that when Y is absent in the formula (I), then X should be CH;

W is CH or a nitrogen atom, provided that when X is CH, then W should be a nitrogen atom;

s is an integer of 1 to 5;

t is an integer of 1 to 5;

when $R^3$ is a hydrogen atom or alkyl, $R^2$ and $R^{2'}$ are the same or different and each is a hydroxyl group or hydroxyalkyl; and when $R^3$ is hydroxyalkyl, $R^2$ and $R^{2'}$ are the same or different and each is a hydrogen atom, a hydroxyl group, alkyl or hydroxyalkyl, an optically active form thereof, a pharmaceutically acceptable salt thereof, a water adduct thereof, a hydrate thereof or a solvate thereof.

5. The isoquinoline compound of claim 1, which is represented by the formula (I), wherein $R^1$ a hydrogen atom or methyl;

Y is absent, methylene, ethylene, propylene or 2-hydroxypropylene; and

R is represented by the formula (II), wherein, in the formula (II),

X is CH or a nitrogen atom, provided that when Y is absent in the formula (I), then X should be CH;

W is CH or a nitrogen atom, provided that when X is CH, then W should be a nitrogen atom;

s is an integer of 1 to 3;

t is an integer of 1 to 4;

when $R^3$ is a hydrogen atom or methyl, $R^2$ is a hydrogen atom, methyl, ethyl, a hydroxyl group, hydroxymethyl or 2-hydroxyethyl and $R^{2'}$ is a hydroxyl group, hydroxymethyl, 2-hydroxyethyl, methoxymethyl, ethoxymethyl, propoxymethyl or isopropoxymethyl; and when $R^3$ is 2-hydroxyethyl, 3-hydroxypropyl, 4-hydroxybutyl or 2-hydroxypropyl, $R^2$ and $R^{2'}$ are the same or different and each is a hydrogen atom, hydroxyl group, methyl, hydroxymethyl or 2-hydroxyethyl, an optically active form thereof, a pharmaceutically acceptable salt thereof, a water adduct thereof, a hydrate thereof or a solvate thereof.

6. The isoquinoline compound of claim 1, which is represented by the formula (I), wherein $R^1$ is a hydrogen atom or methyl;

Y is absent, methylene, ethylene, propylene or 2-hydroxypropylene; and

R is represented by the formula (II), wherein, in the formula (II),

X is CH or a nitrogen atom, provided that when Y is absent in the formula (I), then X should be CH;

W is CH or a nitrogen atom, provided that when X is CH, then W should be a nitrogen atom;

s is an integer of 1 to 3;

t is an integer of 1 to 4;

when $R^3$ is a hydrogen atom or methyl, $R^2$ and $R^{2'}$ are the same or different and each is a hydroxyl group, hydroxymethyl or 2-hydroxyethyl; and when $R^3$ is 2-hydroxyethyl, 3-hydroxypropyl, 4-hydroxybutyl or 2-hydroxypropyl, $R^2$ and $R^{2'}$ are the same or different and each is a hydrogen atom, hydroxyl group, methyl, hydroxymethyl or 2-hydroxyethyl, an optically active form thereof, a pharmaceutically acceptable salt thereof, a water adduct thereof, a hydrate thereof or a solvate thereof.

7. The isoquinoline compound of claim 1, which is selected from (1a) (R)-3-[2-(3-hydroxypyrrolidin-1-yl)ethyl]-5-methyl-2H-isoquinolin-1-one, (2a) 3-[1-(2-hydroxyethyl)piperidin-4-yl]-5-methyl-2H-isoquinolin-1-one, (3a) 3-[3-(3-hydroxypyrrolidin-1-yl)propyl]-2H-isoquinolin-1-one, (4a) 3-[3-(3-hydroxypyrrolidin-1-yl)propyl]-5-methyl-2H-isoquinolin-1-one, (5a) 3-[2-(3-hydroxypyrrolidin-1-yl)ethyl]-5-methyl-2H-isoquinolin-1-one, (6a) 3-[2-(3-hydroxypyrrolidin-1-yl)ethyl]-2H-isoquinolin-1-one, (7a) 3-[2-(2-hydroxymethylpiperidin-1-yl)ethyl]-5-methyl-2H-isoquinolin-1-one, (8a) 3-[2-(2-hydroxymethylpiperidin-1-yl)ethyl]-2H-isoquinolin-1-one, (9a) 3-[1-(2-hydroxyethyl)piperidin-4-yl]-2H-isoquinolin-1-one, (10a) 3-[1-(3-hydroxypropyl)piperidin-4-yl]-2H-isoquinolin-1-one, (11a) 3-[1-(4-hydroxybutyl)piperidin-4-yl]-2H-isoquinolin-1-one, (14a) (S)-3-[2-(2-hydroxymethylpyrrolidin-1-yl)ethyl]-5-methyl-2H-isoquinolin-1-one, (15a) (S)-3-[2-(2-hydroxymethylpyrrolidin-1-yl)ethyl]-2H-isoquinolin-1-one, (16a) (S)-3-[3-(2-hydroxymethylpyrrolidin-1-yl)propyl]-5-methyl-2H-isoquinolin-1-one, (17a) (S)-3-[3-(2-hydroxymethylpyrrolidin-1-yl)propyl]-2H-isoquinolin-1-one, (18a) (R)-3-[3-(2-hydroxymethylpyrrolidin-1-yl)propyl]-2H-isoquinolin-1-one, (19a) 3-[2-(4-hydroxypiperidin-1-yl)ethyl]-2H-isoquinolin-1-one, (20a) (R)-3-[2-(2-hydroxymethylpyrrolidin-1-yl)ethyl]-2H-isoquinolin-1-one, (21a) 3-(1-methyl-2-hydroxymethylpiperidin-4-yl)-2H-isoquinolin-1-one, (22a) 3-[1-(3-hydroxy-2,2-dimethylpropyl)piperidin-4-yl]-2H-isoquinolin-1-one, (23a) 5-methyl-3-[1-(3-hydroxypropyl)piperidin-4-yl]-2H-isoquinolin-1-one, (24a) 3-[1-(2-hydroxypropyl)piperidin-4-yl]-2H-isoquinolin-1-one, (25a) 3-[2-(4-hydroxypiperidin-1-yl)ethyl]-5-methyl-2H-isoquinolin-1-one (26a) (R)-3-[3-(2-hydroxymethylpyrrolidin-1-yl)propyl]-5-methyl-2H-isoquinolin-1-one, (27a) 3-[2-(3-hydroxypiperidin-1-yl)ethyl]-2H-isoquinolin-1-one, (28a) 3-[1-(2-hydroxyethyl)pyrrolidin-3-yl]-5-methyl-2H-isoquinolin-1-one, (29a) 3-[1-(2-hydroxyethyl)pyrrolidin-3-yl]-2H-isoquinolin-1-one, (30a) 5-methyl-3-[1-(2-hydroxypropyl)piperidin-4-yl]-2H-isoquinolin-1-one, (31a) 5-methyl-3-[1-(4-hydroxybutyl)piperidin-4-yl]-2H-isoquinolin-1-one, (32a) 3-[2-(3-hydroxypiperidin-1-yl)ethyl]-5-methyl-2H-isoquinolin-1-one, (33a) 3-[1-(3-hydroxypropyl)pyrrolidin-3-yl]-5-methyl-2H-isoquinolin-1-one, (34a) (S)-3-[2-(3-hydroxypyrrolidin-1-yl)ethyl]-5-methyl-2H-isoquinolin-1-one, (35a) (R)-3-[2-(3-hydroxypiperidin-1-yl)ethyl]-5-methyl-2H-isoquinolin-1-one, (37a) (−)-3-[1-(2-hydroxylethyl)pyrrolidin-3-yl]-5-methyl-2H-isoquinolin-1-one, and (38a) (+)-3-[1-(2-hydroxylethyl)pyrrolidin-3-yl]-5-methyl-2H-isoquinolin-1-one, an optically active form thereof, a pharmaceutically acceptable salt thereof, a hydrate thereof or a water adduct thereof.

8. The isoquinoline compound of claim 1, which is selected from
- (1b) 3-[2-(3,5-dimethyl-2-hydroxymethylpyrrolidin-1-yl)ethyl]-5-methyl-2H-isoquinolin-1-one,
- (10b) 3-{2-[(2R,4S)-4-hydroxy-2-hydroxymethylpyrrolidin-1-yl]ethyl}-5-methyl-2H-isoquinolin-1-one,
- (11b) 3-{2-[(2R,4R)-4-hydroxy-2-hydroxymethylpyrrolidin-1-yl]ethyl}-5-methyl-2H-isoquinolin-1-one,
- (16b) (R)-5-fluoro-3-[2-(2-hydroxymethylpyrrolidin-1-yl)ethyl]-2H-isoquinolin-1-one,
- (17b) (R)-5-chloro-3-[2-(2-hydroxymethylpyrrolidin-1-yl)ethyl]-2H-isoquinolin-1-one,
- (18b) (R)-5-fluoro-3-[2-(3-hydroxypyrrolidin-1-yl)ethyl]-2H-isoquinolin-1-one,
- (19b) (R)-5-chloro-3-[2-(3-hydroxypyrrolidin-1-yl)ethyl]-2H-isoquinolin-1-one,
- (20b) (R)-5-methyl-3-[2-(2-methoxymethylpyrrolidin-1-yl)ethyl]-2H-isoquinolin-1-one hydrochloride,
- (21b) (R)-5-chloro-3-[2-(2-methoxymethylpyrrolidin-1-yl)ethyl]-2H-isoquinolin-1-one hydrochloride,
- (22b) (R)-5-fluoro-3-[2-(2-methoxymethylpyrrolidin-1-yl)ethyl]-2H-isoquinolin-1-one hydrochloride,
- (23b) (R)-3-[2-(2-ethoxymethylpyrrolidin-1-yl)ethyl]-5-methyl-2H-isoquinolin-1-one hydrochloride,
- (24b) (R)-5-chloro-3-[2-(2-ethoxymethylpyrrolidin-1-yl)ethyl]-2H-isoquinolin-1-one hydrochloride, and
- (25b) (R)-3-[2-(2-ethoxymethylpyrrolidin-1-yl)ethyl]-5-fluoro-2H-isoquinolin-1-one hydrochloride, an optically active form thereof, a pharmaceutically acceptable salt thereof, a hydrate thereof or a water adduct thereof.

9. The isoquinoline compound of claim 1, which is represented by the formula (I), wherein
$R^1$ is a hydrogen atom or methyl;
Y is absent; and
R is represented by the formula (II),
wherein, in the formula (II),
X is CH;
W is a nitrogen atom;
s is an integer of 1 or 2;
t is an integer of 2;
when $R^3$ is methyl, $R^2$ is a hydrogen atom, methyl, ethyl, a hydroxyl group or hydroxymethyl and $R^{2'}$ is a hydroxyl group, hydroxymethyl, methoxymethyl, ethoxymethyl, propoxymethyl or isopropoxymethyl; and
when $R^3$ is hydroxyethyl, $R^2$ and $R^{2'}$ are the same or different and each is a hydrogen atom, a hydroxyl group or hydroxymethyl, an optically active form thereof, a pharmaceutically acceptable salt thereof, a water adduct thereof, a hydrate thereof or a solvate thereof.

10. The isoquinoline compound of claim 1, which is represented by the formula (I), wherein
$R^1$ is a hydrogen atom or methyl;
Y is absent; and
R is represented by the formula (II),
wherein, in the formula (II),
X is CH;
W is a nitrogen atom;
s is an integer of 1 or 2;
t is an integer of 2;
when $R^3$ is methyl, $R^2$ and $R^{2'}$ are the same or different and each is a hydroxyl group or hydroxymethyl; and
when $R^3$ is hydroxyethyl, $R^2$ and $R^{2'}$ are the same or different and each is a hydrogen atom, a hydroxyl group or hydroxymethyl, an optically active form thereof, a pharmaceutically acceptable salt thereof, a water adduct thereof, a hydrate thereof or a solvate thereof.

11. The isoquinoline compound of claim 1, which is selected from
- (2a) 3-[1-(2-hydroxyethyl)piperidin-4-yl]-5-methyl-2H-isoquinolin-1-one
- (9a) 3-[1-(2-hydroxyethyl)piperidin-4-yl]-2H-isoquinolin-1-one
- (10a) 3-[1-(3-hydroxypropyl)piperidin-4-yl]-2H-isoquinolin-1-one
- (11a) 3-[1-(4-hydroxybutyl)piperidin-4-yl]-2H-isoquinolin-1-one
- (21a) 3-(1-methyl-2-hydroxymethylpiperidin-4-yl)-2H-isoquinolin-1-one
- (22a) 3-[1-(3-hydroxy-2,2-dimethylpropyl)piperidin-4-yl]-2H-isoquinolin-1-one
- (23a) 5-methyl-3-[1-(3-hydroxypropyl)piperidin-4-yl]-2H-isoquinolin-1-one
- (24a) 3-[1-(2-hydroxypropyl)piperidin-4-yl]-2H-isoquinolin-1-one
- (28a) 3-[1-(2-hydroxyethyl)pyrrolidin-3-yl]-5-methyl-2H-isoquinolin-1-one
- (29a) 3-[1-(2-hydroxyethyl)pyrrolidin-3-yl]-2H-isoquinolin-1-one
- (30a) 5-methyl-3-[1-(2-hydroxypropyl)piperidin-4-yl]-2H-isoquinolin-1-one
- (31a) 5-methyl-3-[1-(4-hydroxybutyl)piperidin-4-yl]-2H-isoquinolin-1-one
- (33a) 3-[1-(3-hydroxypropyl)pyrrolidin-3-yl]-5-methyl-2H-isoquinolin-1-one
- (37a) (−)-3-[1-(2-hydroxylethyl)pyrrolidin-3-yl]-5-methyl-2H-isoquinolin-1-one and
- (38a) (+)-3-[1-(2-hydroxylethyl)pyrrolidin-3-yl]-5-methyl-2H-isoquinolin-1-one, an optically active form thereof, a pharmaceutically acceptable salt thereof, a water adduct thereof, a hydrate thereof or a solvate thereof.

12. The isoquinoline compound of claim 1, which is represented by the formula (I), wherein
$R^1$ is a hydrogen atom or methyl;
Y is ethylene or propylene; and
R is represented by the formula (II),
wherein, in the formula (II),
X is a nitrogen atom;
W is CH;
s is an integer of 1 to 3;
t is an integer of 1 to 4;
$R^2$ is a hydrogen atom, alkyl, a hydroxyl group or hydroxymethyl and $R^{2'}$ is a hydroxyl group, hydroxymethyl, methoxymethyl, ethoxymethyl, propoxymethyl or isopropoxymethyl; and
$R^3$ is a hydrogen atom, an optically active form thereof, a pharmaceutically acceptable salt thereof, a water adduct thereof, a hydrate thereof or a solvate thereof.

13. The isoquinoline compound of claim 1, which is selected from
- (1a) (R)-3-[2-(3-hydroxypyrrolidin-1-yl)ethyl]-5-methyl-2H-isoquinolin-1-one,
- (3a) 3-[3-(3-hydroxypyrrolidin-1-yl)propyl]-2H-isoquinolin-1-one, (4a) 3-[3-(3-hydroxypyrrolidin-1-yl)propyl]-5-methyl-2H-isoquinolin-1-one,
(5a) 3-[2-(3-hydroxypyrrolidin-1-yl)ethyl]-5-methyl-2H-isoquinolin-1-one,
(6a) 3-[2-(3-hydroxypyrrolidin-1-yl)ethyl]-2H-isoquinolin-1-one,
(7a) 3-[2-(2-hydroxymethylpiperidin-1-yl)ethyl]-5-methyl-2H-isoquinolin-1-one,
(8a) 3-[2-(2-hydroxymethylpiperidin-1-yl)ethyl]-2H-isoquinolin-1-one,
(14a) (S)-3-[2-(2-hydroxymethylpyrrolidin-1-yl)ethyl]-5-methyl-2H-isoquinolin-1-one,
(15a) (S)-3-[2-(2-hydroxymethylpyrrolidin-1-yl)ethyl]-2H-isoquinolin-1-one,
(16a) (S)-3-[3-(2-hydroxymethylpyrrolidin-1-yl)propyl]-5-methyl-2H-isoquinolin-1-one,
(17a) (S)-3-[3-(2-hydroxymethylpyrrolidin-1-yl)propyl]-2H-isoquinolin-1-one,
(18a) (R)-3-[3-(2-hydroxymethylpyrrolidin-1-yl)propyl]-2H-isoquinolin-1-one,
(19a) 3-[2-(4-hydroxypiperidin-1-yl)ethyl]-2H-isoquinolin-1-one,
(20a) (R)-3-[2-(2-hydroxymethylpyrrolidin-1-yl)ethyl]-2H-isoquinolin-1-one,
(25a) 3-[2-(4-hydroxypiperidin-1-yl)ethyl]-5-methyl-2H-isoquinolin-1-one
(26a) (R)-3-[3-(2-hydroxymethylpyrrolidin-1-yl)propyl]-5-methyl-2H-isoquinolin-1-one,
(27a) 3-[2-(3-hydroxypiperidin-1-yl)ethyl]-2H-isoquinolin-1-one,
(32a) 3-[2-(3-hydroxypiperidin-1-yl)ethyl]-5-methyl-2H-isoquinolin-1-one,
(34a) (S)-3-[2-(3-hydroxypyrrolidin-1-yl)ethyl]-5-methyl-2H-isoquinolin-1-one, and
(35a) (R)-3-[2-(3-hydroxypiperidin-1-yl)ethyl]-5-methyl-2H-isoquinolin-1-one,
an optically active form thereof, a pharmaceutically acceptable salt thereof, a water adduct thereof, a hydrate thereof or a solvate thereof.

14. The isoquinoline compound of claim 1, which is selected from
(10b) 3-{2-[(2R,4S)-4-hydroxy-2-hydroxymethylpyrrolidin-1-yl]ethyl}-5-methyl-2H-isoquinolin-1-one,
(11b) 3-{2-[(2R,4R)-4-hydroxy-2-hydroxymethylpyrrolidin-1-yl]ethyl}-5-methyl-2H-2H-isoquinolin-1-one,
(16b) (R)-5-fluoro-3-[2-(2-hydroxymethylpyrrolidin-1-yl)ethyl]-2H-isoquinolin-1-one,
(17b) (R)-5-chloro-3-[2-(2-hydroxymethylpyrrolidin-1-yl)ethyl]-2H-isoquinolin-1-one,
(18b) (R)-5-fluoro-3-[2-(3-hydroxypyrrolidin-1-yl)ethyl]-2H-isoquinolin-1-one,
(19b) (R)-5-chloro-3-[2-(3-hydroxypyrrolidin-1-yl)ethyl]-2H-isoquinolin-1-one,
(20b) (R)-5-methyl-3-[2-(2-methoxymethylpyrrolidin-1-yl)ethyl]-2H-isoquinolin-1-one hydrochloride,
(21b) (R)-5-chloro-3-[2-(2-methoxymethylpyrrolidin-1-yl)ethyl]-2H-isoquinolin-1-one hydrochloride,
(22b) (R)-5-fluoro-3-[2-(2-methoxymethylpyrrolidin-1-yl)ethyl]-2H-isoquinolin-1-one hydrochloride,
(23b) (R)-3-[2-(2-ethoxymethylpyrrolidin-1-yl)ethyl]-5-methyl-2H-isoquinolin-1-one hydrochloride,
(24b) (R)-5-chloro-3-[2-(2-ethoxymethylpyrrolidin-1-yl)ethyl]-2H-isoquinolin-1-one hydrochloride, and
(25b) (R)-3-[2-(2-ethoxymethylpyrrolidin-1-yl)ethyl]-5-fluoro-2H-isoquinolin-1-one hydrochloride, an optically active form thereof, a pharmaceutically acceptable salt thereof, a water adduct thereof, a hydrate thereof or a solvate thereof.

15. The isoquinoline compound of claim 1, which is represented by the formula (I), wherein
$R^1$ is a hydrogen atom or methyl;
Y is absent or ethylene;
R is represented by the formula (II),
wherein, in the formula (II),
when Y is present in the formula (I), X is a nitrogen atom; when Y is absent in the formula (I), X is CH;
W is CH or a nitrogen atom, provided that when X is CH, then W should be a nitrogen atom;
s is an integer of 1 or 2;
t is an integer of 1 to 3;
when $R^3$ is a hydrogen atom, $R^2$ a hydrogen atom, a hydroxyl group or hydroxymethyl and R is a hydroxyl group, hydroxymethyl, methoxymethyl, ethoxymethyl, propoxymethyl or isopropoxymethyl; and
when $R^3$ is hydroxyethyl, $R^2$ and $R^{2'}$ are each a hydrogen atom, a hydroxyl group or hydroxymethyl,
an optically active form thereof, a pharmaceutically acceptable salt thereof, a water adduct thereof, a hydrate thereof or a solvate thereof.

16. The isoquinoline compound of claim 1, which is represented by the formula (I), wherein
$R^1$ is a hydrogen atom or methyl;
Y is absent or ethylene;
R is represented by the formula (II),
wherein, in the formula (II),
when Y is present in the formula (I), X is a nitrogen atom; when Y is absent in the formula (I), X is CH;
W is CH or a nitrogen atom, provided that when X is CH, then W should be a nitrogen atom;
s is an integer of 1 or 2;
t is an integer of 1 to 3;
when $R^3$ is a hydrogen atom, $R^2$ and $R^{2'}$ are each a hydroxyl group or hydroxymethyl; and
when $R^3$ is hydroxyethyl, $R^2$ and $R^{2'}$ are each a hydrogen atom, a hydroxyl group or hydroxymethyl,
an optically active form thereof, a pharmaceutically acceptable salt thereof, a water adduct thereof, a hydrate thereof or a solvate thereof.

17. The isoquinoline compound of claim 1, which is selected from
(1a) (R)-3-[2-(3-hydroxypyrrolidin-1-yl)ethyl]-5-methyl-2H-isoquinolin-1-one,
(2a) 3-[1-(2-hydroxyethyl)piperidin-4-yl]-5-methyl-2H-isoquinolin-1-one,
(5a) 3-[2-(3-hydroxypyrrolidin-1-yl)ethyl]-5-methyl-2H-isoquinolin-1-one,
(28a) 3-[1-(2-hydroxyethyl)pyrrolidin-3-yl]-5-methyl-2H-isoquinolin-1-one,
(34a) (S)-3-[2-(3-hydroxypyrrolidin-1-yl)ethyl]-5-methyl-2H-isoquinolin-1-one,
(37a) (−)-3-[1-(2-hydroxyethyl)pyrrolidin-3-yl]-5-methyl-2H-isoquinolin-1-one, and
(38a) (+)-3-[1-(2-hydroxyethyl)pyrrolidin-3-yl]-5-methyl-2H-isoquinolin-1-one,
an optically active form thereof, a pharmaceutically acceptable salt thereof, a water adduct thereof, a hydrate thereof or a solvate thereof.

18. The isoquinoline compound of claim 1, which is represented by the formula (I), wherein,
$R^1$ is methyl;
Y is absent; and
R is represented by the formula (II), wherein
X is CH;
W is a nitrogen atom;
s is 1 or 2;
t is an integer of 2;
$R^2$ and $R^{2'}$ are the same or different and each is a hydrogen atom, a hydroxyl group or hydroxyalkyl; and
$R^3$ is hydroxyethyl,
an optically active form thereof, a pharmaceutically acceptable salt thereof, a water adduct thereof, a hydrate thereof or a solvate thereof.

19. The isoquinoline compound of claim 1, which is
(2a) 3-[1-(2-Hydroxyethyl)piperidin-4-yl]-5-methyl-2H-isoquinolin-1-one, an optically active form thereof, a pharmaceutically acceptable salt thereof, a water adduct thereof, a hydrate thereof or a solvate thereof.

20. The isoquinoline compound of claim 1, which is
(28a) 3-[1-(2-Hydroxyethyl)pyrrolidin-3-yl]-5-methyl-2H-isoquinolin-1-one, an optically active form thereof, a pharmaceutically acceptable salt thereof, a water adduct thereof, a hydrate thereof or a solvate thereof.

21. The isoquinoline compound of claim 1, which is
(37a) (+)-3-[1-(2-Hydroxyethyl)pyrrolidin-3-yl]-5-methyl-2H-isoquinolin-1-one, a pharmaceutically acceptable salt thereof, a water adduct thereof, a hydrate thereof or a solvate thereof.

22. The isoquinoline compound of claim 1, which is
(38a) (−)-3-[1-(2-Hydroxyethyl)pyrrolidin-3-yl]-5-methyl-2H-isoquinolin-1-one, a pharmaceutically acceptable salt thereof, a water adduct thereof, a hydrate thereof or a solvate thereof.

23. The isoquinoline compound of claim 1, which is represented by the formula (I), wherein
$R^1$ is methyl;
Y is ethylene;
R is represented by the formula (II),
wherein, in the formula (II),
X is a nitrogen atom;
W is CH;
t is an integer of 2 or 3;
$R^2$ is a hydrogen atom, a hydroxyl group or hydroxymethyl and $R^{2'}$ is a hydroxyl group, hydroxymethyl, methoxymethyl, ethoxymethyl, propoxymethyl or isopropoxymethyl; and
$R^3$ is a hydrogen atom,
an optically active form thereof, a pharmaceutically acceptable salt thereof, a water adduct thereof, a hydrate thereof or a solvate thereof.

24. An isoquinoline compound represented by the formula (I'):

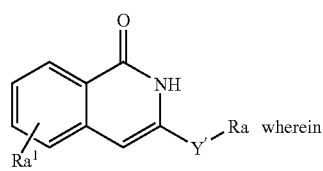

(I')

$Ra^1$ is a hydrogen atom or methyl;
Y' is ethylene, propylene or 2-hydroxypropylene; and
Ra is represented by the formula (II'):

(II')

wherein, in the formula (II'),
X' is a nitrogen atom;
W' is CH;
s' is an integer of 1 to 3;
t' is an integer of 1 to 4;
$Ra^2$ and $Ra^{2'}$ are the same or different and each is a hydrogen atom, a hydroxyl group, alkyl or hydroxymethyl; and
$Ra^3$ a hydrogen atom,
provided that when $Ra^2$ is a hydrogen atom or alkyl, $Ra^{2'}$ is a hydroxyl group or hydroxymethyl,
an optically active form thereof, a pharmaceutically acceptable salt thereof, a water adduct thereof, a hydrate thereof or a solvate thereof.

25. The isoquinoline compound of claim 24, which is represented by the formula (I'), wherein
$Ra^1$ is methyl;
Y' is ethylene;
Ra is represented by the formula (II'),
wherein, in the formula (II'),
X' is a nitrogen atom;
W' is CH;
s' is 1;
t' is an integer of 2 or 3;
$Ra^2$ and $Ra^{2'}$ are the same or different and each is a hydrogen atom, a hydroxyl group or hydroxymethyl; and
$Ra^3$ a hydrogen atom,
provided that when $Ra^2$ is a hydrogen atom, then $Ra^{2'}$ should be a hydroxyl group or hydroxymethyl,
an optically active form thereof, a pharmaceutically acceptable salt thereof, a water adduct thereof, a hydrate thereof or a solvate thereof.

26. The isoquinoline compound of claim 1, which is
(1a) (R)-3-[2-(3-Hydroxypyrrolidin-1-yl)ethyl]-5-methyl-2H-isoquinolin-1-one, a pharmaceutically acceptable salt thereof, a water adduct thereof, a hydrate thereof or a solvate thereof.

27. The isoquinoline compound of claim 1, which is
(5a) 3-[2-(3-Hydroxypyrrolidin-1-yl)ethyl]-5-methyl-2H-isoquinolin-1-one, a pharmaceutically acceptable salt thereof, a water adduct thereof, a hydrate thereof or a solvate thereof.

28. The isoquinoline compound of claim 1, which is
(34a) (S)-3-[2-(3-Hydroxypyrrolidin-1-yl)ethyl]-5-methyl-2H-isoquinolin-1-one, a pharmaceutically acceptable salt thereof, a water adduct thereof, a hydrate thereof or a solvate thereof.

29. An isoquinoline compound, which is selected from
(12a) 3-[2-hydroxy-3-(pyrrolidin-1-yl)propyl]-2H-isoquinolin-1-one, and
(13a) 3-[2-hydroxy-3-(pyrrolidin-1-yl)propyl]-5-methyl-2H-isoquinolin-1-one,
an optically active form thereof, a pharmaceutically acceptable salt thereof, a hydrate thereof or a water adduct thereof.

30. A pharmaceutical composition comprising (i) the isoquinoline compound of claim 1, an optically active form thereof, a pharmaceutically acceptable salt thereof, a water adduct thereof, a hydrate thereof or a solvate thereof and (ii) a pharmaceutically acceptable carrier.

31. A method for producing a compound of the following formula (I):

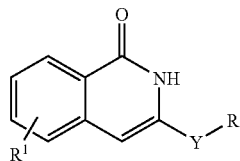

wherein
R¹ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;
Y is absent or an alkylene chain having 1 to 8 carbon atoms wherein an optional carbon atom may have a hydroxyl group; and
R is represented by the following formula (II):

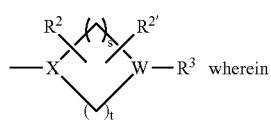 wherein wherein
X is CH or a nitrogen atom, provided that when Y is absent in the formula (I), then X should be CH;
W is CH or a nitrogen atom, provided that when X is CH, then W should be a nitrogen atom;
s is an integer of 1 to 5;
t is an integer of 1 to 5;
when R³ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, R² is a hydrogen atom, alkyl, a hydroxyl group or hydroxyalkyl and R²' is a hydroxyl group, hydroxyalkyl or alkoxyalkyl; and
when R³ is hydroxyalkyl, R² and R²' are the same or different and each is a hydrogen atom, a hydroxyl group, alkyl, hydroxyalkyl, alkoxycarbonyl, dialkylaminoalkyl or dialkylcarbamoyl, or R² and R²' are taken together to form ketone,
which comprises using a compound of the following formula (16):

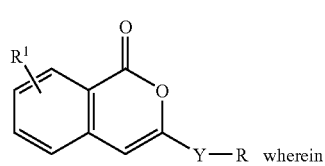

R¹ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;
Y is absent or an alkylene chain having 1 to 8 carbon atoms wherein an optional carbon atom may have a hydroxyl group; and
R is represented by the following formula (II):

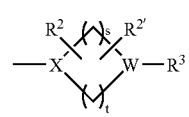

wherein
X is CH or a nitrogen atom, provided that when Y is absent in the formula (I), then X should be CH;
W is CH or a nitrogen atom, provided that when X is CH, then W should be a nitrogen atom;
s is an integer of 1 to 5;
t is an integer of 1 to 5;
when R³ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, R² is a hydrogen atom, alkyl, a hydroxyl group or hydroxyalkyl and R²' is a hydroxyl group, hydroxyalkyl or alkoxyalkyl; and
when R² is hydroxyalkyl, R² and R²' are the same or different and each is a hydrogen atom, a hydroxyl group, alkyl, hydroxyalkyl, alkoxycarbonyl, dialkylaminoalkyl or dialkylcarbamoyl, or R² and R²' are taken together to form ketone.

32. The method of claim 31, wherein R² and R²' are the same or different and each is a hydroxyl group or hydroxyalkyl, when R³ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino.

33. A method for producing the isoquinoline compound represented by the following formula (I):

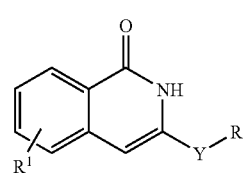

wherein
R¹ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl. N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;
Y is absent or an alkylene chain having 1 to 8 carbon atoms wherein an optional carbon atom may have a hydroxyl group; and R is represented by the following formula (II):

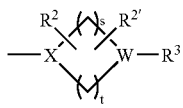

wherein
X is CH or a nitrogen atom, provided that when Y is absent in the formula (I) then X should be CH;
W is CH or a nitrogen atom, provided that when X is CH, then W should be a nitrogen atom;
s is an integer of 1 to 5;
t is an integer of 1 to 5;
when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, $R^2$ is a hydrogen atom, alkyl, a hydroxyl group or hydroxyalkyl and $R^{2'}$ is a hydroxyl group, hydroxyalkyl or alkoxyalkyl and
when $R^3$ is hydroxyalkyl, $R^2$ and $R^{2'}$ are the same or different and each is a hydrogen atom, a hydroxyl group, alkyl, hydroxyalkyl, alkoxycarbonyl, dialkylaminoalkyl or dialkylcarbamoyl, or $R^2$ and $R^{2'}$ are taken together to form ketone,
an optically active form thereof, a pharmaceutically acceptable salt thereof, a water adduct thereof, a hydrate thereof or a solvate thereof, which comprises the steps of any of the following (a), (b), or (c):
(a) reacting a compound of the following formula (11'):

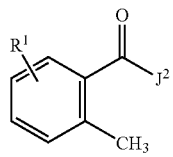

wherein $R^1$ is as defined above and $J^2$ is dialkylamino, with a compound of the following formula (14):

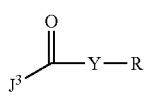

wherein Y and R are as defined above and $J^3$ is N-alkyl-N-alkoxyamino, to produce a compound of the following formula (15):

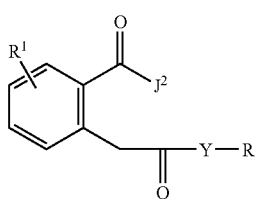

wherein each symbol is as defined above;

(b) using a compound of the following formula (15):

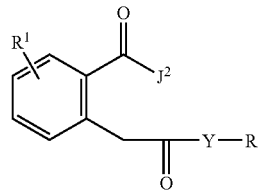

wherein each symbol is as defined above, to produce a compound of the following formula (16):

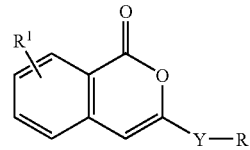

wherein each symbol is as defined above; and
(c) using a compound of the following formula (16):

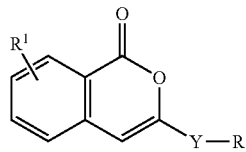

wherein each symbol is as defined above, to produce a compound of the following formula (I):

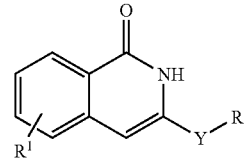

wherein each symbol is as defined above.

34. The method of claim 33, wherein $R^2$ and $R^{2'}$ are the same or different and each is a hydroxyl group or hydroxyalkyl, when $R^3$ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino.

35. A method for producing the isoquinoline compound represented by the following formula (I):

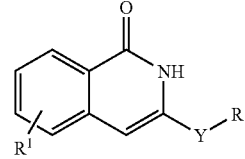

wherein

R¹ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;

Y is absent or an alkylene chain having 1 to 8 carbon atoms wherein an optional carbon atom may have a hydroxyl group; and R is represented by the following formula (II):

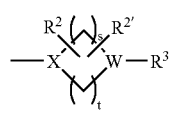

(II)

wherein

X is CH or a nitrogen atom, provided that when Y is absent in the formula (I), then X should be CH;

W is CH or a nitrogen atom, provided that when X is CH, then W should be a nitrogen atom;

s is an integer of 1 to 5;

t is an integer of 1 to 5;

when R³ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino, R² is a hydrogen atom, alkyl, a hydroxyl group or hydroxyalkyl and R²' is a hydroxyl group, hydroxyalkyl or alkoxyalkyl; and when R³ is hydroxyalkyl, R² and R²' are the same or different and each is a hydrogen atom, a hydroxyl group, alkyl, hydroxyalkyl, alkoxycarbonyl, dialkylaminoalkyl or dialkylcarbamoyl, or R² and R²' are taken together to form ketone, an optically active form thereof, a pharmaceutically acceptable salt thereof, a water adduct thereof, a hydrate thereof or a solvate thereof, which comprises the steps (a), (b), and (c):

(a) reacting a compound of the following formula (11'):

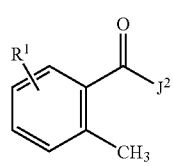

(11')

wherein R¹ is as defined above and J² is dialkylamino, with a compound of the following formula (14):

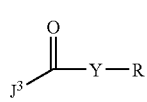

(14)

wherein Y and R are as defined above and J³ is N-alkyl-N-alkoxyamino, to produce a compound of the following formula (15):

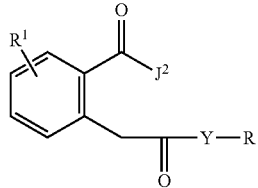

(15)

wherein each symbol is as defined above;

(b) using a compound of the following formula (15):

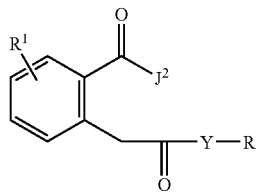

(15)

wherein each symbol is as defined above, to produce a compound of the following formula (16):

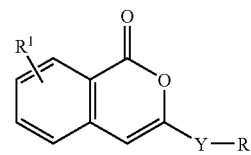

(16)

wherein each symbol is as defined above; and (c) using a compound of the following formula (16):

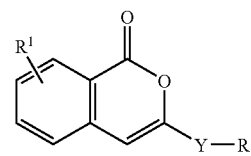

(16)

wherein each symbol is as defined above, to produce a compound of the following formula (I):

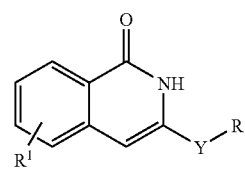

(I)

wherein each symbol is as defined above.

36. The method claim 35, wherein R² and R²' are the same or different and each is a hydroxyl group or hydroxyalkyl, when R³ is a hydrogen atom, alkyl, amino, monoalkylamino, dialkylamino, alkoxycarbonyl, alkylsulfonyl, acyl, acylamino optionally having a substituent, benzoylamino optionally having a substituent, arylalkyl, sulfamoyl or alkylsulfonylamino.

* * * * *

UNITED STATES PATENT AND TRADEMARK OFFICE
CERTIFICATE OF CORRECTION

PATENT NO. : 7,459,465 B2  Page 1 of 1
APPLICATION NO. : 11/688103
DATED : December 2, 2008
INVENTOR(S) : Fujio et al.

It is certified that error appears in the above-identified patent and that said Letters Patent is hereby corrected as shown below:

TITLE PAGE OF THE PATENT

The heading "( * ) Notice:" should read -- Subject to any disclaimer, the term of this patent is extended or adjusted under 35 U.S.C 154(b) by 0 days. This patent is subject to a terminal disclaimer. --

IN THE CLAIMS

Claim 2, column 60, line 55, "thereof" should read -- thereof, --

Claim 24, column 68, line 14, "t" should read -- t' --

Claim 25, column 68, line 36, "$Ra^3$ a hydrogen atom," should read -- $Ra^3$ is a hydrogen atom, --

Claim 31, column 69, line 46, "R is a hydrogen atom," should read -- $R^2$ is a hydrogen atom, --

Claim 33, column 70, line 60, "carbamoyl." should read -- carbamoyl, --

Signed and Sealed this

Twenty-eighth Day of April, 2009

JOHN DOLL
*Acting Director of the United States Patent and Trademark Office*